United States Patent
An et al.

(10) Patent No.: US 12,285,437 B2
(45) Date of Patent: Apr. 29, 2025

(54) REVERSING THE UNDESIRABLE PH-PROFILE OF DOXORUBICIN VIA ACTIVATION OF A DISUBSTITUTED MALEAMIC ACID PRODRUG AT TUMOR ACIDITY

(71) Applicant: The Research Foundation for The State University of new York, Binghamton, NY (US)

(72) Inventors: Ming An, Vestal, NY (US); Lan Yao, Vestal, NY (US); Anqi Zhang, Vestal, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 479 days.

(21) Appl. No.: 17/086,312

(22) Filed: Oct. 30, 2020

(65) Prior Publication Data

US 2021/0128592 A1 May 6, 2021

Related U.S. Application Data

(60) Provisional application No. 62/928,143, filed on Oct. 30, 2019.

(51) Int. Cl.
| | | |
|---|---|---|
| *A61K 31/704* | (2006.01) | |
| *A61K 9/08* | (2006.01) | |
| *A61K 47/54* | (2017.01) | |
| *A61K 47/64* | (2017.01) | |

(52) U.S. Cl.
CPC .............. *A61K 31/704* (2013.01); *A61K 9/08* (2013.01); *A61K 47/545* (2017.08); *A61K 47/64* (2017.08)

(58) Field of Classification Search
CPC ................................ A61K 31/704; A61K 47/64
See application file for complete search history.

(56) References Cited

U.S. PATENT DOCUMENTS

| | | | |
|---|---|---|---|
| 1,007,978 A | 11/1911 | Sauveur | |
| 1,513,924 A | 11/1924 | Murdock | |
| 1,655,370 A | 1/1928 | Hill | |
| D320,325 S | 10/1991 | Barfield | |
| 5,140,013 A * | 8/1992 | Gaudreault | C07H 15/252 514/1.2 |
| 5,143,830 A | 9/1992 | Holland et al. | |
| 5,278,049 A | 1/1994 | Baker et al. | |
| 5,354,675 A | 10/1994 | Iida et al. | |
| 5,399,490 A | 3/1995 | Balganesh et al. | |
| 5,466,463 A | 11/1995 | Ford | |
| 5,466,672 A | 11/1995 | Kushnaryov et al. | |
| 5,495,001 A | 2/1996 | McGrogan et al. | |
| 5,569,597 A | 10/1996 | Grimsley et al. | |
| 5,635,484 A | 6/1997 | Ayres et al. | |
| 5,712,369 A | 1/1998 | Old et al. | |
| 6,030,780 A | 2/2000 | Vinkemeier et al. | |
| 6,037,526 A | 3/2000 | Grimsley et al. | |
| 6,080,849 A | 6/2000 | Bermudes et al. | |
| 6,190,657 B1 | 2/2001 | Pawelek et al. | |
| 6,207,156 B1 | 3/2001 | Kuchroo et al. | |
| 6,232,110 B1 | 5/2001 | Pallas et al. | |
| 6,329,002 B1 | 12/2001 | Kim et al. | |
| 6,355,790 B1 | 3/2002 | Rosenblatt et al. | |
| 6,376,234 B1 | 4/2002 | Grimsley et al. | |
| 6,447,784 B1 | 9/2002 | Bermudes et al. | |
| 6,475,482 B1 | 11/2002 | Bermudes et al. | |
| 6,548,287 B1 | 4/2003 | Powell et al. | |
| 6,605,697 B1 | 8/2003 | Kwon et al. | |
| 6,638,912 B2 | 10/2003 | Bhatnagar et al. | |
| 6,685,935 B1 | 2/2004 | Pawelek et al. | |
| 6,743,893 B2 | 6/2004 | Engler et al. | |
| 6,841,535 B2 | 1/2005 | Divita et al. | |
| 6,863,894 B2 | 3/2005 | Bermudes et al. | |
| 6,923,972 B2 | 8/2005 | Bermudes et al. | |
| 6,962,696 B1 | 11/2005 | Bermudes et al. | |
| 7,354,592 B2 | 4/2008 | Bermudes et al. | |
| 7,358,084 B2 | 4/2008 | Kolkman | |
| 7,390,646 B2 | 6/2008 | Andino-Pavlovsky et al. | |

(Continued)

OTHER PUBLICATIONS

Zhang, A. et al."Reversing the undesirable pH-profile of doxorubicin . . . " ChemComm, vol. 53, No. 95, pp. 12826-12829. (Year: 2017).*
Supporting Information for: Zhang, A. et al."Reversing the undesirable pH-profile of doxorubicin . . . " ChemComm, vol. 53, No. 95, pp. 12826-12829. (Year: 2017).*
Jayaprakash, S. et al "Design and synthesis of a PSMA inhibitor-doxorubicin conjugate . . . " ChemMedChem, vol. 1, pp. 299-302. ( Year: 2006).*
Ivanenkov, Y. et al."Synthesis and biological evaluation of doxorubicin-containing conjugate . . . " Bioorg. Med. Chem. Let., vol. 29, pp. 1246-1255. (Year: 2019).*
"PKa and Electrical Properties of Amino Acids" https://orgosolver.com/chapters/chapter-15/pka-and-electrical-properties-of-amino-acids Retrieved from the internet Nov. 21, 2023. (Year: 2023).*

(Continued)

*Primary Examiner* — Layla D Berry
(74) *Attorney, Agent, or Firm* — Hoffberg & Associates; Steven M. Hoffberg

(57) ABSTRACT

A pre-prodrug, comprising a drug, e.g., doxorubicin, which has off-target toxicity (e.g., cardiotoxicity) with respect to its antineoplastic activity, and an amine functionality of the drug incorporated into a disubstituted maleimide (DMI). The pre-prodrug may be linked to a targeting or de-targeting agent or a polar modulator, e.g., charged ligand, amino acid, peptide, etc., to increase therapeutic index. The pre-prodrug is hydrolyzed to the prodrug, having a disubstituted maleamic acid (DMA). A polar modulator such as glutamic acid prevents cellular uptake of the prodrug, but not the doxorubicin drug released from the prodrug after dissociation. The prodrug is pH sensitive, and below pH 7.0, tends to cleave to form free drug and cyclized maleic anhydride. Tumor environments tend to be more acidic, e.g., pH 6.8, than cardiac tissue, e.g., pH 7.4, and therefore the heart is spared while the drug is selectively released within a tumor.

21 Claims, 32 Drawing Sheets

(56) References Cited

U.S. PATENT DOCUMENTS

| | | |
|---|---|---|
| 7,452,531 B2 | 11/2008 | Bermudes et al. |
| 7,514,089 B2 | 4/2009 | Bermudes et al. |
| 7,635,682 B2 | 12/2009 | Denmeade et al. |
| 7,666,627 B2 | 2/2010 | Gal et al. |
| 7,700,349 B2 | 4/2010 | Romaine et al. |
| 7,700,830 B2 | 4/2010 | Corbin et al. |
| 7,705,195 B2 | 4/2010 | French et al. |
| 7,803,918 B2 | 9/2010 | van der Hoek |
| 7,888,321 B2 | 2/2011 | Cooper et al. |
| 7,892,803 B2 | 2/2011 | Tanner et al. |
| 7,892,825 B2 | 2/2011 | Barr et al. |
| 7,947,822 B2 | 5/2011 | Nabel et al. |
| 7,964,362 B2 | 6/2011 | Lee et al. |
| 7,989,202 B1 | 8/2011 | Mach et al. |
| 8,030,542 B2 | 10/2011 | Corbin et al. |
| 8,062,885 B2 | 11/2011 | Mach et al. |
| 8,101,349 B2 | 1/2012 | Garcia et al. |
| 8,101,826 B2 | 1/2012 | Romano |
| 8,119,354 B2 | 2/2012 | Katanaev |
| 8,173,397 B2 | 5/2012 | Gal et al. |
| 8,206,700 B2 | 6/2012 | Horwitz et al. |
| 8,236,315 B2 | 8/2012 | Lazarides et al. |
| 8,241,623 B1 | 8/2012 | Bermudes |
| 8,244,484 B2 | 8/2012 | Lee et al. |
| 8,323,961 B2 | 12/2012 | Nabel et al. |
| 8,440,207 B2 | 5/2013 | Bermudes |
| 8,445,650 B2 | 5/2013 | Simpson et al. |
| 8,524,220 B1 | 9/2013 | Bermudes |
| 8,603,824 B2 | 12/2013 | Ramseier et al. |
| 8,623,350 B1 | 1/2014 | Bermudes |
| 8,628,782 B2 | 1/2014 | Berkower |
| 8,647,642 B2 | 2/2014 | Bermudes |
| 8,686,218 B2 | 4/2014 | Romaine et al. |
| 8,741,313 B2 | 6/2014 | Sable et al. |
| 8,748,373 B2 | 6/2014 | Chai et al. |
| 8,759,086 B2 | 6/2014 | Mach et al. |
| 8,771,669 B1 | 7/2014 | Bermudes |
| 8,771,671 B2 | 7/2014 | Spencer et al. |
| 8,791,237 B2 | 7/2014 | Paterson et al. |
| 8,821,893 B2 | 9/2014 | Dattwyler et al. |
| 8,835,107 B2 | 9/2014 | Van Der Hoek |
| 8,853,362 B2 | 10/2014 | Tissot et al. |
| 8,906,662 B2 | 12/2014 | Nataro et al. |
| 8,920,809 B2 | 12/2014 | Dirienzo |
| 8,926,993 B2 | 1/2015 | Dubensky, Jr. et al. |
| 8,956,859 B1 | 2/2015 | Bermudes |
| 8,962,816 B2 | 2/2015 | Ertl et al. |
| 8,969,542 B2 | 3/2015 | Buyse et al. |
| 8,999,949 B2 | 4/2015 | Spencer et al. |
| 9,068,187 B1 | 6/2015 | Bermudes |
| 9,109,229 B2 | 8/2015 | Ramseier et al. |
| 9,161,974 B2 | 10/2015 | Dubensky et al. |
| 9,187,762 B2 | 11/2015 | Albert et al. |
| 9,198,960 B2 | 12/2015 | Dubensky, Jr. et al. |
| 9,200,251 B1 | 12/2015 | Bermudes |
| 9,200,289 B1 | 12/2015 | Bermudes |
| 9,206,456 B2 | 12/2015 | Lenormand |
| 9,737,592 B1 | 8/2017 | Bermudes et al. |
| 2001/0029024 A1 | 10/2001 | Kodadek |
| 2002/0016982 A1 | 2/2002 | Romaine et al. |
| 2002/0026655 A1 | 2/2002 | Bermudes et al. |
| 2002/0106380 A1 | 8/2002 | Hung et al. |
| 2002/0107374 A1 | 8/2002 | Pallas et al. |
| 2002/0123053 A1 | 9/2002 | Luo et al. |
| 2003/0059400 A1 | 3/2003 | Szalay |
| 2003/0092066 A1 | 5/2003 | Vinkemeier et al. |
| 2003/0106096 A1 | 6/2003 | Barry |
| 2003/0109026 A1 | 6/2003 | Bermudes et al. |
| 2003/0113293 A1 | 6/2003 | Bermudes et al. |
| 2003/0114372 A1 | 6/2003 | White et al. |
| 2003/0115630 A1 | 6/2003 | Romano |
| 2003/0124561 A1 | 7/2003 | Mach et al. |
| 2003/0131372 A1 | 7/2003 | Copenhaver et al. |
| 2003/0131376 A1 | 7/2003 | Okubara et al. |
| 2003/0144490 A1 | 7/2003 | Edwards et al. |
| 2003/0166140 A1 | 9/2003 | Chen et al. |
| 2003/0170276 A1 | 9/2003 | Bermudes et al. |
| 2003/0186416 A1 | 10/2003 | Pallas et al. |
| 2003/0188336 A1 | 10/2003 | Corbin et al. |
| 2003/0203377 A1 | 10/2003 | Milne Edwards et al. |
| 2003/0211476 A1 | 11/2003 | OMahony et al. |
| 2004/0013658 A1 | 1/2004 | Fulton et al. |
| 2004/0023282 A1 | 2/2004 | Luo et al. |
| 2004/0038307 A1 | 2/2004 | Lee et al. |
| 2004/0096426 A1 | 5/2004 | Chen et al. |
| 2004/0101531 A1 | 5/2004 | Curtiss et al. |
| 2004/0110939 A1 | 6/2004 | Dumas Milne Edwards et al. |
| 2004/0115788 A1 | 6/2004 | Zheng et al. |
| 2004/0133930 A1 | 7/2004 | Cooper et al. |
| 2004/0180380 A1 | 9/2004 | Lee et al. |
| 2004/0191787 A1 | 9/2004 | Tanner et al. |
| 2004/0219169 A1 | 11/2004 | Bermudes et al. |
| 2004/0229338 A1 | 11/2004 | King |
| 2004/0234956 A1 | 11/2004 | Kabat et al. |
| 2004/0266674 A1 | 12/2004 | Mills et al. |
| 2005/0032157 A1 | 2/2005 | Gal et al. |
| 2005/0036987 A1 | 2/2005 | Pawelek et al. |
| 2005/0055746 A1 | 3/2005 | Michaud et al. |
| 2005/0069911 A1 | 3/2005 | Lee et al. |
| 2005/0070007 A1 | 3/2005 | Romaine et al. |
| 2005/0074463 A1 | 4/2005 | Autran et al. |
| 2005/0084972 A1 | 4/2005 | Barr et al. |
| 2005/0112139 A1 | 5/2005 | Karp |
| 2005/0158295 A1 | 7/2005 | Swiercz et al. |
| 2005/0166274 A1 | 7/2005 | French et al. |
| 2005/0180963 A1 | 8/2005 | Adams et al. |
| 2005/0202535 A1 | 9/2005 | Collier et al. |
| 2005/0227917 A1 | 10/2005 | Williams et al. |
| 2005/0241015 A1 | 10/2005 | Mach et al. |
| 2005/0241016 A1 | 10/2005 | Mach et al. |
| 2005/0249706 A1 | 11/2005 | Bermudes et al. |
| 2005/0251885 A1 | 11/2005 | Michaud et al. |
| 2005/0255088 A1 | 11/2005 | Bermudes et al. |
| 2005/0257282 A1 | 11/2005 | Mach et al. |
| 2005/0266560 A1 | 12/2005 | Preuss et al. |
| 2005/0268359 A1 | 12/2005 | Mach et al. |
| 2005/0273882 A1 | 12/2005 | Romano |
| 2005/0281828 A1 | 12/2005 | Bowdish et al. |
| 2006/0009633 A9 | 1/2006 | Dumas Milne Edwards et al. |
| 2006/0014212 A1 | 1/2006 | Benkovic et al. |
| 2006/0024668 A1 | 2/2006 | Hoek |
| 2006/0035270 A1 | 2/2006 | Lee et al. |
| 2006/0035320 A1 | 2/2006 | Tissot et al. |
| 2006/0035371 A1 | 2/2006 | Zheng et al. |
| 2006/0110747 A1 | 5/2006 | Ramseier et al. |
| 2006/0156440 A1 | 7/2006 | Michaud et al. |
| 2006/0160152 A1 | 7/2006 | Vinkemeier et al. |
| 2006/0174357 A1 | 8/2006 | Velander et al. |
| 2006/0182762 A1 | 8/2006 | Irene Martina Maas et al. |
| 2006/0223142 A1 | 10/2006 | Dumas Milne Edwards et al. |
| 2006/0269561 A1 | 11/2006 | Paterson et al. |
| 2006/0275823 A1 | 12/2006 | Kodadek |
| 2006/0275897 A1 | 12/2006 | Nabel et al. |
| 2006/0286639 A1 | 12/2006 | Dumas Milne Edwards et al. |
| 2007/0009489 A1 | 1/2007 | Bermudes et al. |
| 2007/0020327 A1 | 1/2007 | Fikes et al. |
| 2007/0028324 A1 | 2/2007 | Corbin et al. |
| 2007/0059799 A1 | 3/2007 | Sette et al. |
| 2007/0143871 A1 | 6/2007 | French et al. |
| 2007/0298012 A1 | 12/2007 | King et al. |
| 2008/0019994 A1 | 1/2008 | Brunham et al. |
| 2008/0038296 A1 | 2/2008 | Brahmbhatt et al. |
| 2008/0070255 A1 | 3/2008 | Tanner et al. |
| 2008/0085854 A1 | 4/2008 | Barr et al. |
| 2008/0090770 A1 | 4/2008 | Belmares et al. |
| 2008/0124355 A1 | 5/2008 | Bermudes |
| 2008/0269070 A1 | 10/2008 | Ramseier et al. |
| 2008/0286306 A1 | 11/2008 | Nabel et al. |
| 2008/0288264 A1 | 11/2008 | Mach et al. |
| 2008/0311081 A1 | 12/2008 | Fruehauf et al. |
| 2009/0019609 A1 | 1/2009 | Romano |
| 2009/0023157 A1 | 1/2009 | Lee et al. |
| 2009/0029369 A1 | 1/2009 | Cottier et al. |
| 2009/0042248 A1 | 2/2009 | Gal et al. |

(56) References Cited

U.S. PATENT DOCUMENTS

| | | |
|---|---|---|
| 2009/0042278 A1 | 2/2009 | Barr et al. |
| 2009/0123426 A1 | 5/2009 | Li et al. |
| 2009/0169517 A1 | 7/2009 | Bermudes et al. |
| 2009/0169566 A1 | 7/2009 | Rawlin et al. |
| 2009/0209749 A1 | 8/2009 | Mach et al. |
| 2009/0217396 A1 | 8/2009 | Kyrkanides et al. |
| 2009/0232804 A1 | 9/2009 | Lazarides et al. |
| 2009/0239797 A1 | 9/2009 | Cooper et al. |
| 2009/0240073 A1 | 9/2009 | Barry |
| 2009/0246211 A1* | 10/2009 | Henri ............ A61K 47/64 530/370 |
| 2009/0246220 A1 | 10/2009 | Ertl et al. |
| 2009/0258935 A1 | 10/2009 | Zheng et al. |
| 2009/0294288 A1 | 12/2009 | May et al. |
| 2009/0297560 A1 | 12/2009 | Dattwyler et al. |
| 2009/0317418 A1 | 12/2009 | Catanzaro et al. |
| 2010/0086546 A1 | 4/2010 | Lee et al. |
| 2010/0111998 A1 | 5/2010 | Nabel et al. |
| 2010/0135961 A1 | 6/2010 | Bermudes |
| 2010/0136048 A1 | 6/2010 | Bermudes |
| 2010/0137162 A1 | 6/2010 | Retallack et al. |
| 2010/0169988 A1 | 7/2010 | Kohli et al. |
| 2010/0184613 A1 | 7/2010 | Lee et al. |
| 2010/0189774 A1 | 7/2010 | Lenormand |
| 2010/0215679 A1 | 8/2010 | Horwitz et al. |
| 2010/0215682 A1 | 8/2010 | Berkower |
| 2010/0239546 A1 | 9/2010 | Fruehauf et al. |
| 2010/0247560 A1 | 9/2010 | Simpson et al. |
| 2010/0261201 A1 | 10/2010 | Katanaev |
| 2010/0272750 A1 | 10/2010 | Buyse et al. |
| 2010/0319087 A1 | 12/2010 | Corbin et al. |
| 2010/0333235 A1 | 12/2010 | Mach et al. |
| 2011/0014701 A1 | 1/2011 | Ghosh |
| 2011/0027349 A1 | 2/2011 | Sable et al. |
| 2011/0065091 A1 | 3/2011 | Van Der Hoek |
| 2011/0189774 A1 | 8/2011 | Mach et al. |
| 2011/0201109 A1 | 8/2011 | Zwaka et al. |
| 2011/0223241 A1 | 9/2011 | Tardi et al. |
| 2011/0257080 A1 | 10/2011 | Chai et al. |
| 2011/0262474 A1 | 10/2011 | Du et al. |
| 2011/0274721 A1 | 11/2011 | Nabel et al. |
| 2011/0275585 A1 | 11/2011 | Brahmbhatt et al. |
| 2011/0277180 A1 | 11/2011 | Romano |
| 2011/0293608 A1 | 12/2011 | Jaffee et al. |
| 2011/0305724 A1 | 12/2011 | Paterson et al. |
| 2012/0027785 A1 | 2/2012 | Dirienzo |
| 2012/0042413 A1 | 2/2012 | Albert et al. |
| 2012/0088314 A1 | 4/2012 | Katanaev |
| 2012/0093773 A1 | 4/2012 | Li et al. |
| 2012/0142080 A1 | 6/2012 | Bermudes |
| 2012/0164687 A1 | 6/2012 | Bereta et al. |
| 2012/0195859 A1 | 8/2012 | Vergnolle et al. |
| 2012/0219545 A1 | 8/2012 | Ayuso et al. |
| 2012/0271036 A1 | 10/2012 | Smith et al. |
| 2012/0276132 A1 | 11/2012 | Feng et al. |
| 2012/0308575 A1 | 12/2012 | Guo et al. |
| 2013/0017173 A1 | 1/2013 | Nataro et al. |
| 2013/0028924 A1 | 1/2013 | Ertl et al. |
| 2013/0122043 A1 | 5/2013 | Guimaraes et al. |
| 2013/0129713 A1 | 5/2013 | Rescigno et al. |
| 2013/0202557 A1 | 8/2013 | Li et al. |
| 2013/0209405 A1 | 8/2013 | Roy et al. |
| 2013/0269057 A1 | 10/2013 | Fosu-Nyarko et al. |
| 2013/0276168 A1 | 10/2013 | Romaine et al. |
| 2013/0344033 A1 | 12/2013 | Vergnolle et al. |
| 2014/0057940 A1 | 2/2014 | Mankowski et al. |
| 2014/0093528 A1 | 4/2014 | Berkower |
| 2014/0155343 A1 | 6/2014 | Brahmbhatt et al. |
| 2014/0162279 A1 | 6/2014 | Ramseier et al. |
| 2014/0162952 A1 | 6/2014 | Katagiri et al. |
| 2014/0173774 A1 | 6/2014 | Pareddy et al. |
| 2014/0173780 A1 | 6/2014 | Pareddy et al. |
| 2014/0220661 A1 | 8/2014 | Bermudes |
| 2014/0227286 A1 | 8/2014 | Jaffee et al. |
| 2014/0287419 A1 | 9/2014 | Althoff et al. |
| 2014/0289906 A1 | 9/2014 | Althoff et al. |
| 2015/0017138 A1 | 1/2015 | Fruehauf et al. |
| 2015/0017204 A1 | 1/2015 | Bermudes |
| 2015/0030573 A1 | 1/2015 | Fruehauf et al. |
| 2015/0044256 A1 | 2/2015 | Dattwyler et al. |
| 2015/0050308 A1 | 2/2015 | van der Hoek |
| 2015/0057191 A1 | 2/2015 | Tissot et al. |
| 2015/0125849 A1 | 5/2015 | Yeh et al. |
| 2015/0132330 A1 | 5/2015 | Garcia-Sastre et al. |
| 2015/0153358 A1 | 6/2015 | Ayuso et al. |
| 2015/0197748 A1 | 7/2015 | Liu et al. |
| 2015/0216965 A1 | 8/2015 | Diamond et al. |
| 2015/0225692 A1 | 8/2015 | Bhatia et al. |
| 2015/0231207 A1 | 8/2015 | Kaspar |
| 2015/0246137 A1 | 9/2015 | Guo et al. |
| 2015/0291667 A1 | 10/2015 | Dirienzo |
| 2015/0337321 A1 | 11/2015 | Mach et al. |
| 2015/0351390 A1 | 12/2015 | Castle et al. |
| 2015/0355172 A1 | 12/2015 | Kraus et al. |

OTHER PUBLICATIONS

Hong, L. "Cancer-targeting antibody-drug conjugates . . . " Aust. J. Chem., vol. 64, pp. 779-789. (Year: 2011).*

Langer, M. et al. "Novel peptide conjugates . . . " J. Med. Chem., vol. 44, pp. 1341-1348. (Year: 2001).*

Szij, P. et al "Minireview: addressing the retro-Michael instability . . . " Drug Disc. Today: Technol., vol. 30, pp. 27-34. (Year: 2018).*

* cited by examiner

Potential mechanisms of pH-dependent drug release

Synthesis of the DMA prodrug via the DMI precursor

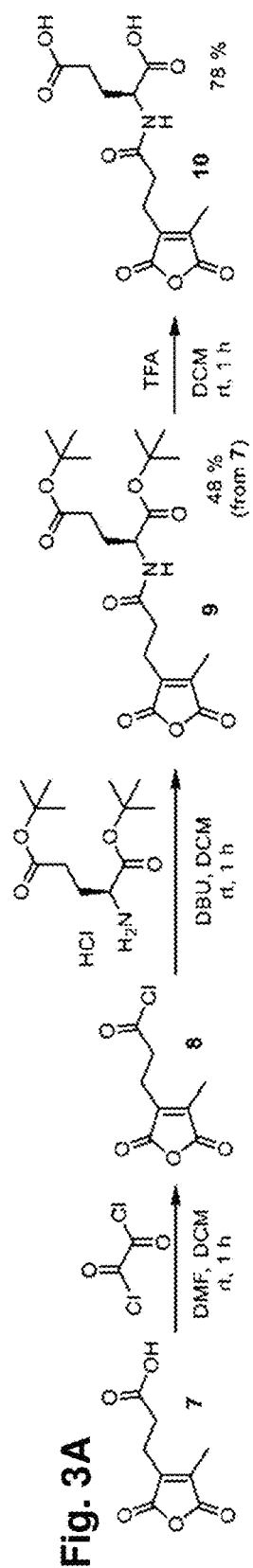
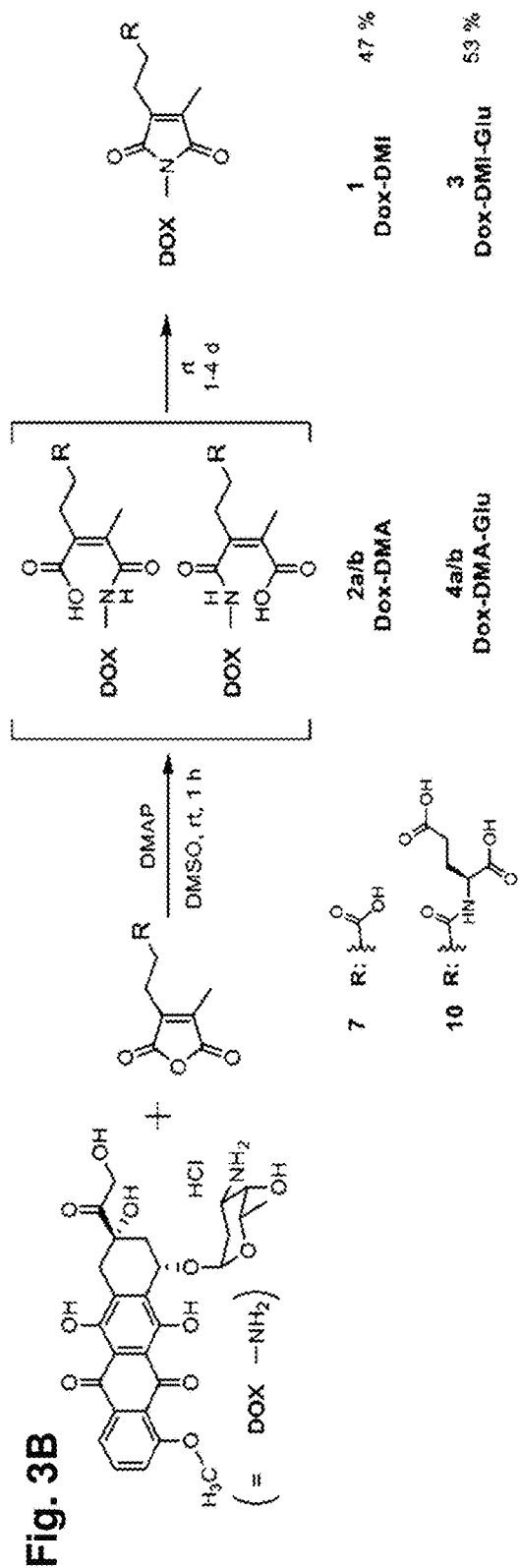
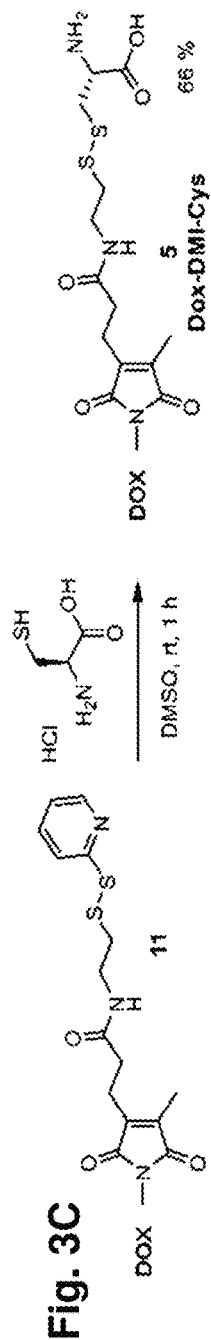
Fig. 3A / Fig. 3B / Fig. 3C Synthesis of DMI pre-prodrugs of Dox

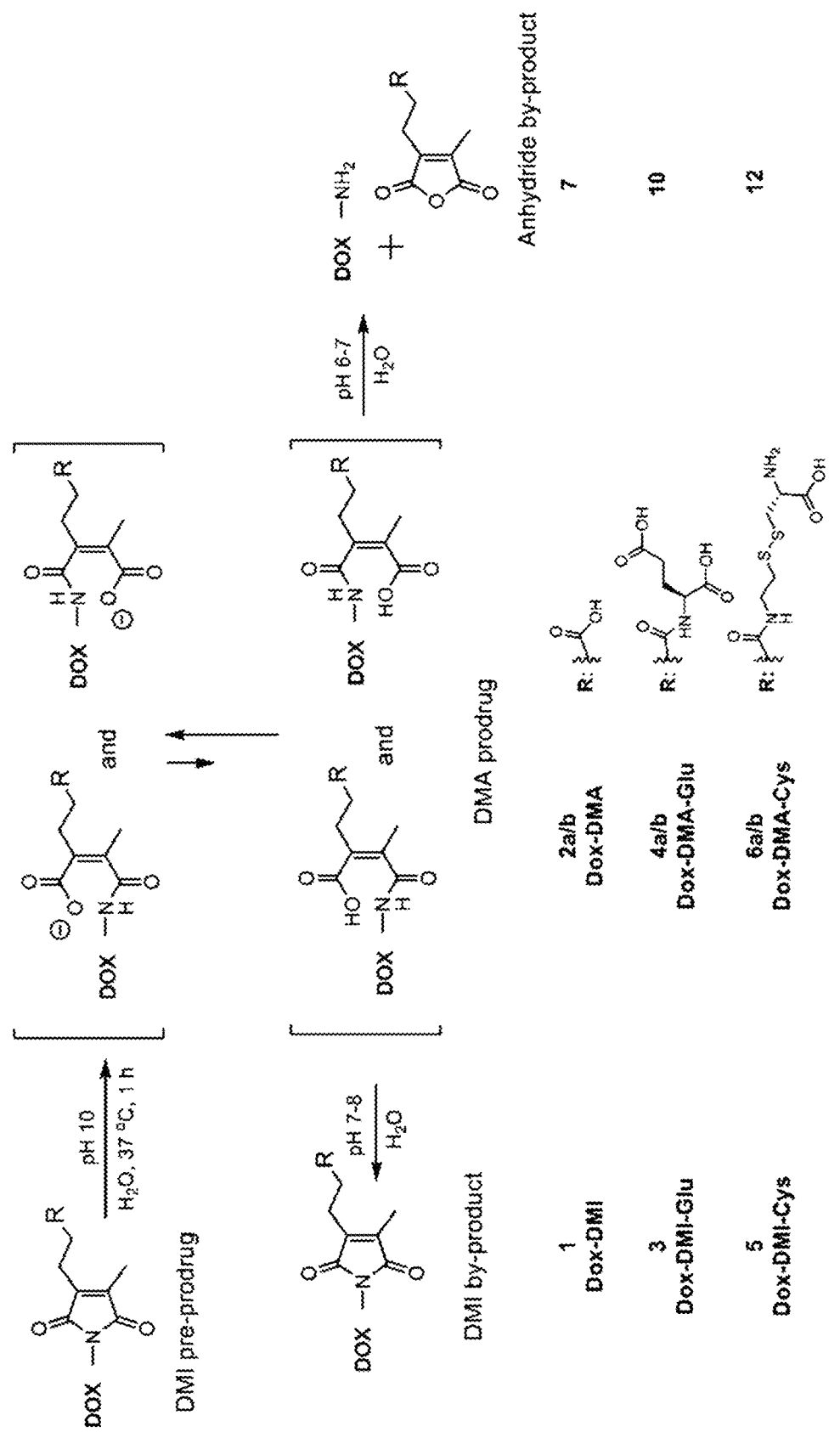
Fig. 4 Preparation of DMA prodrugs and drug release reactions

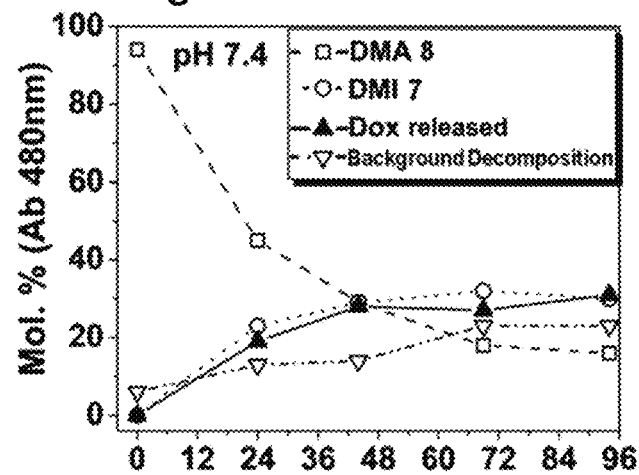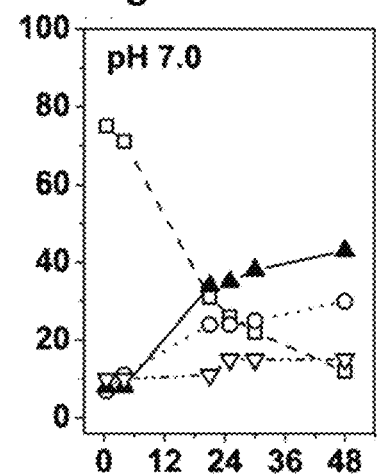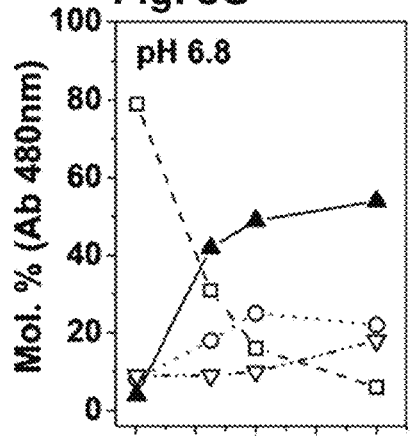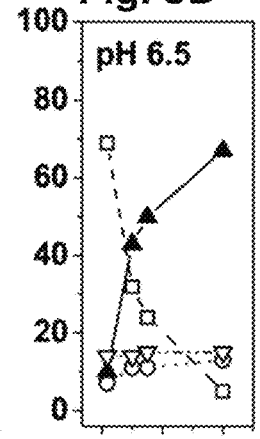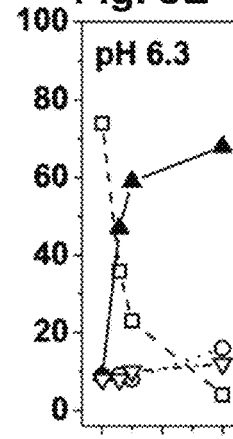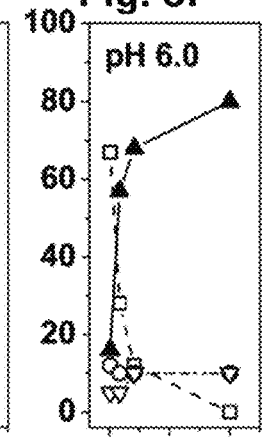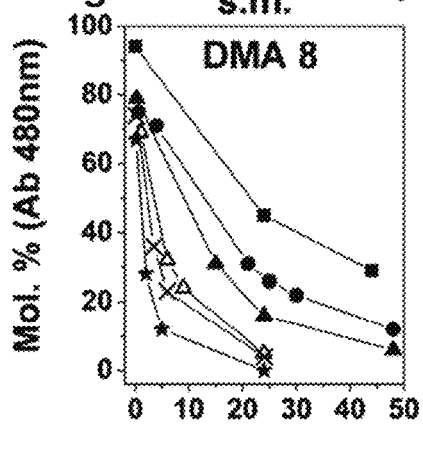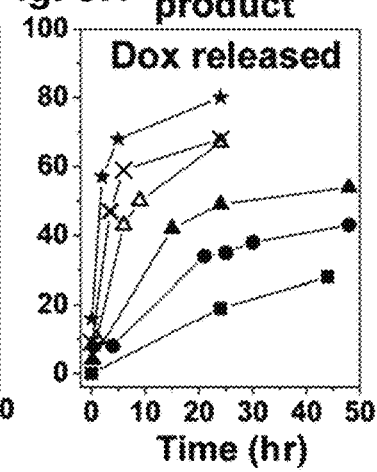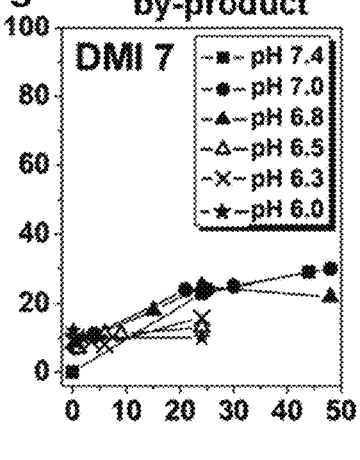
Dox release from DMA prodrug 8 in pH 6.0–7.4 aq. buffer at RT

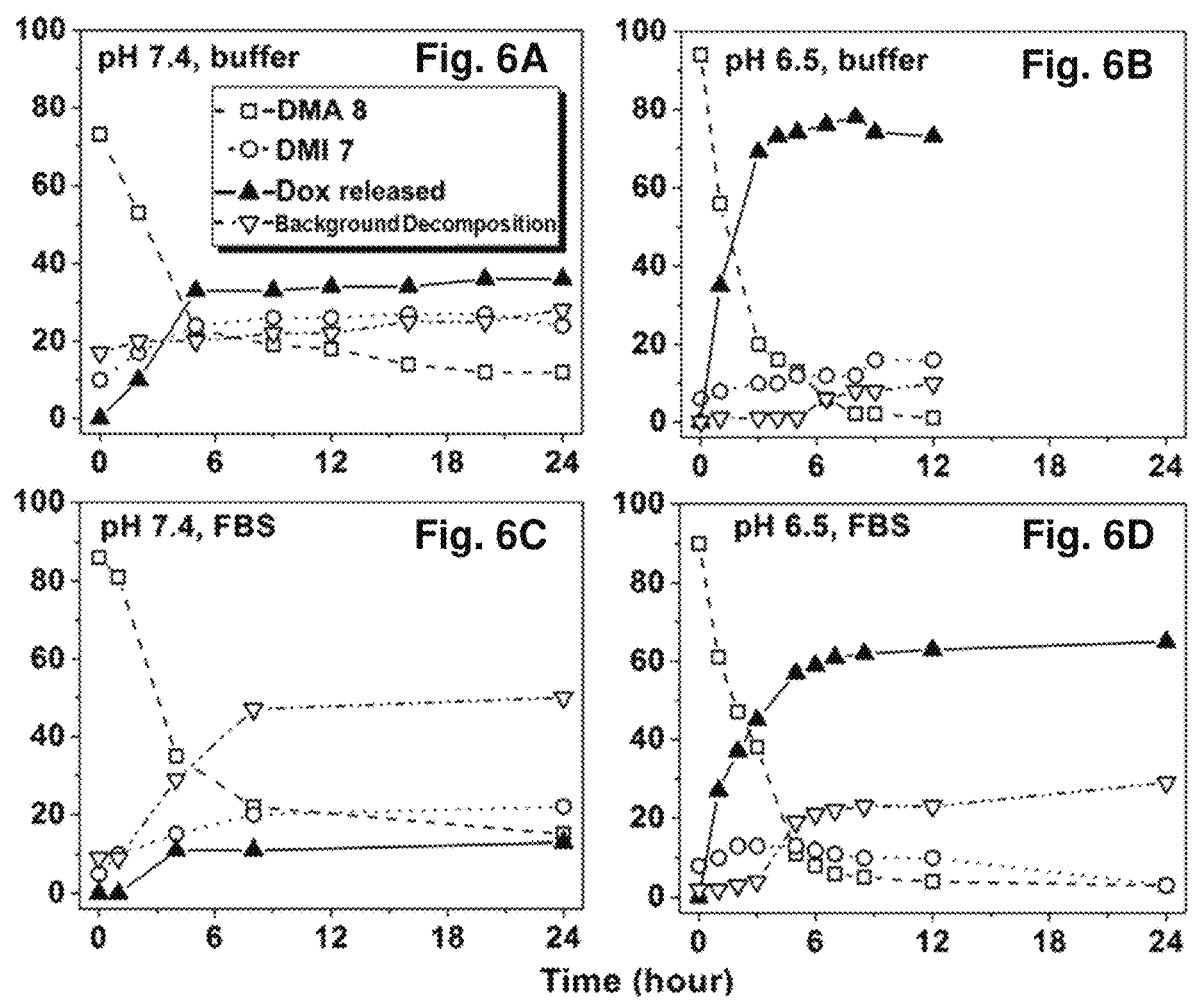
Dox release from DMA 8 at 37.1C with or without serum

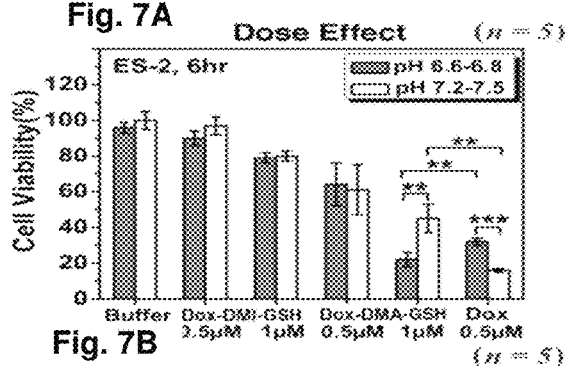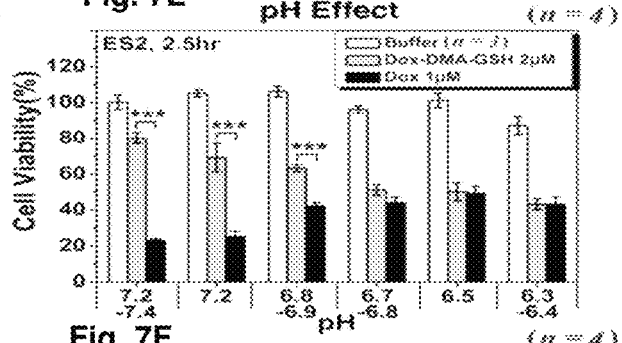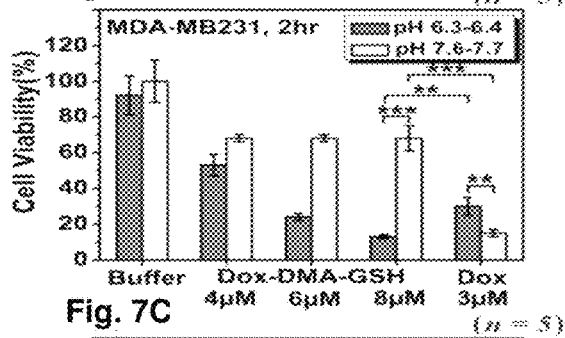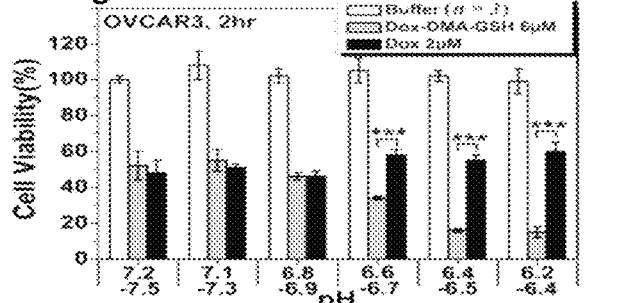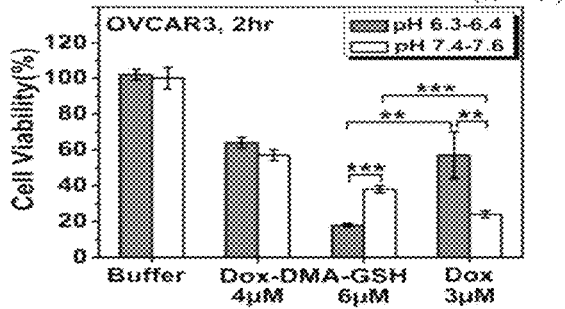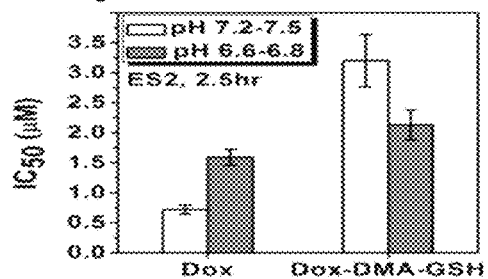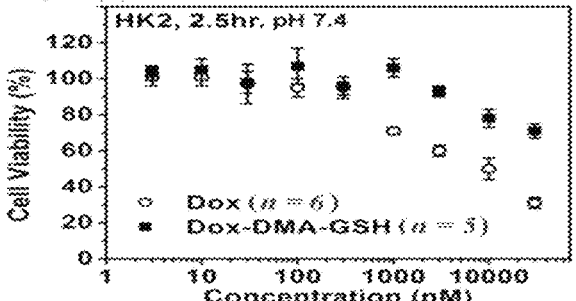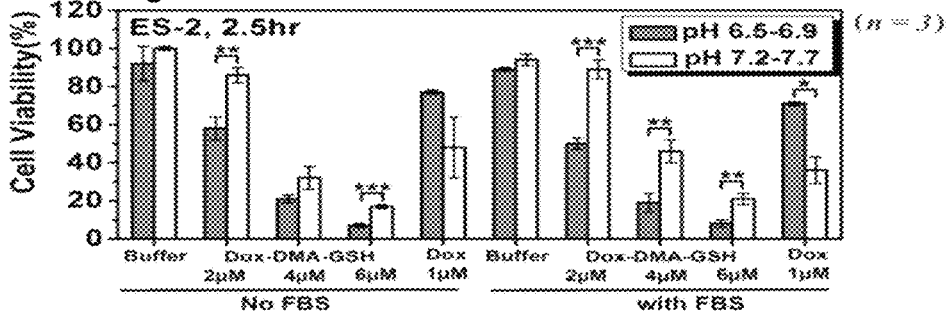
Prodrug8 can reverse the unfavorable pH-profile of Dox.

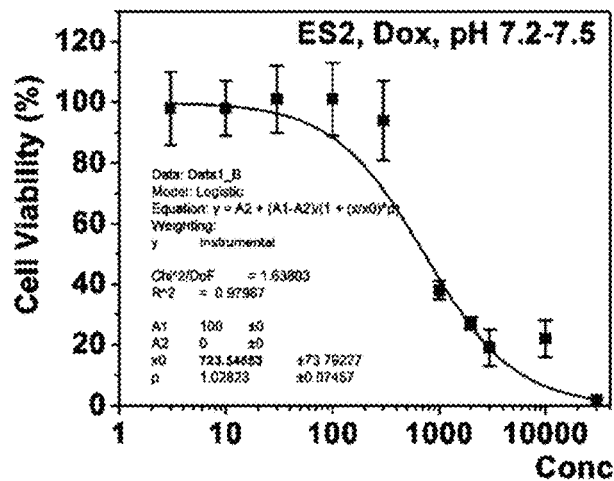 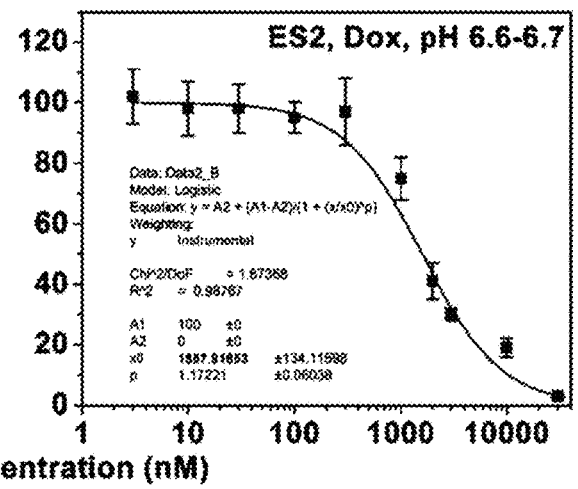
Fig. 11A  Fig. 11B
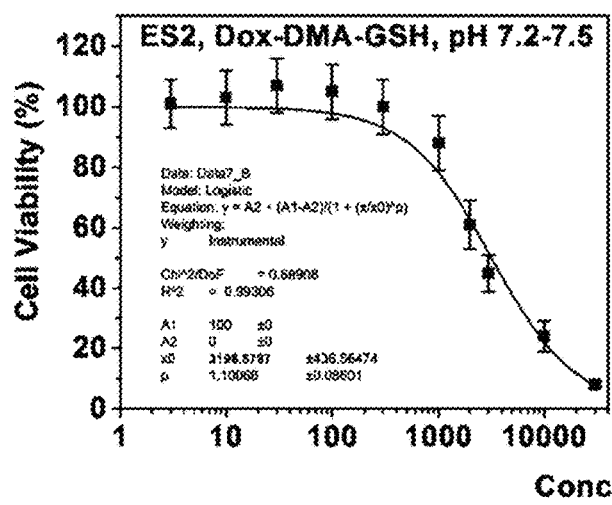 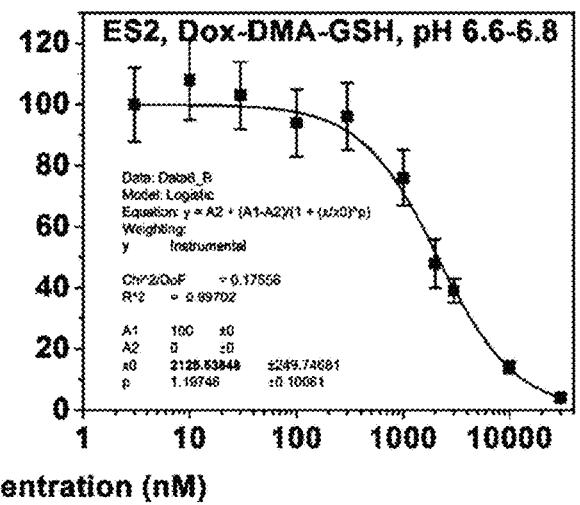
Fig. 11C  Fig. 11D

- Dox-DMA-GSH
- Dox-DMA
- Dox-DMA-Glu
- Dox-DMA-Cys

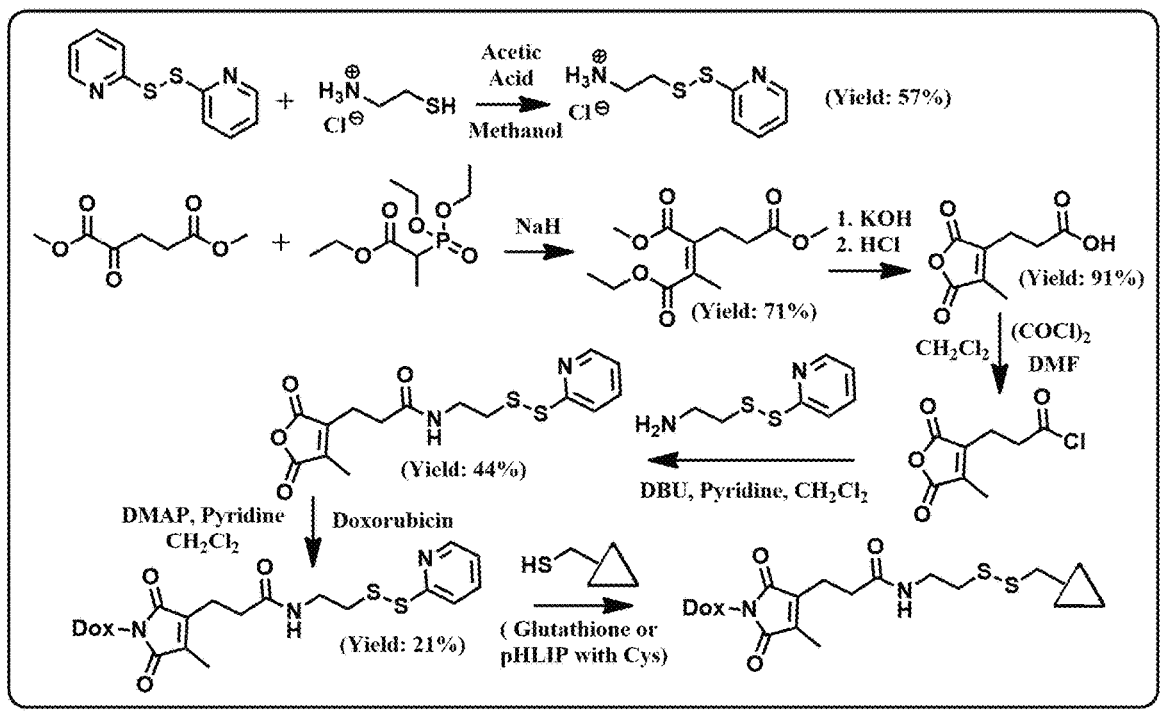
Fig. 17
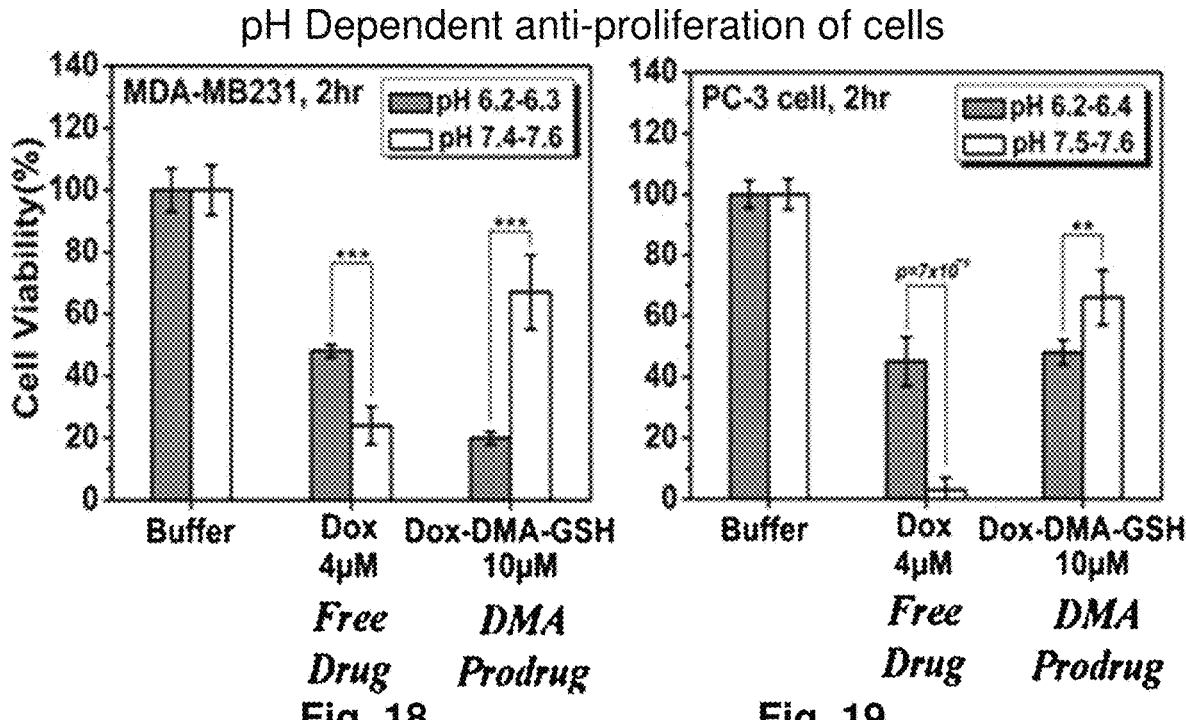
Fig. 18                      Fig. 19

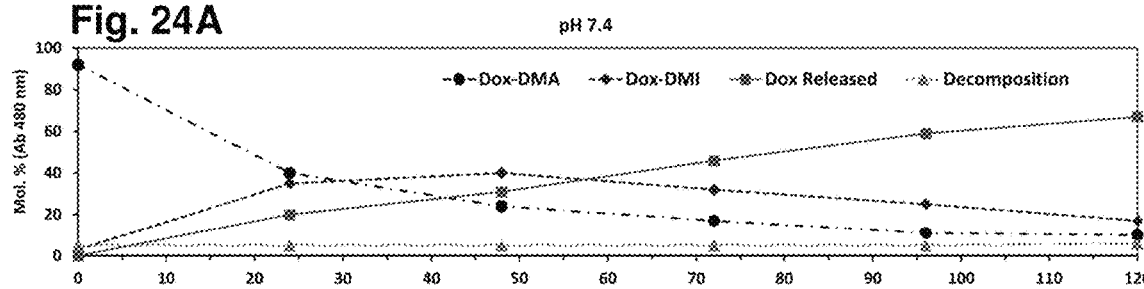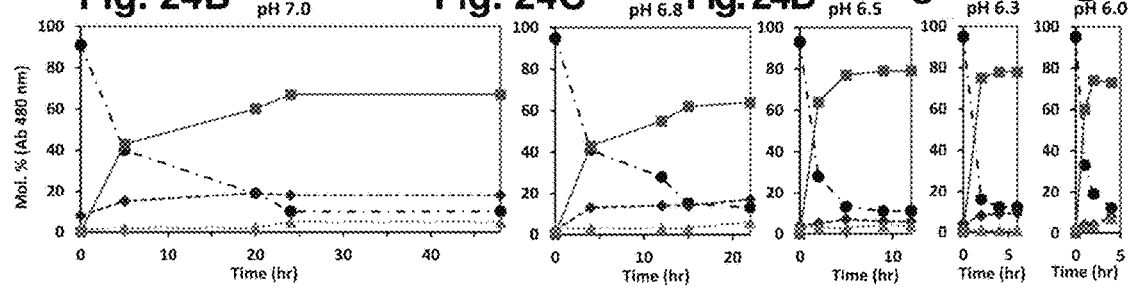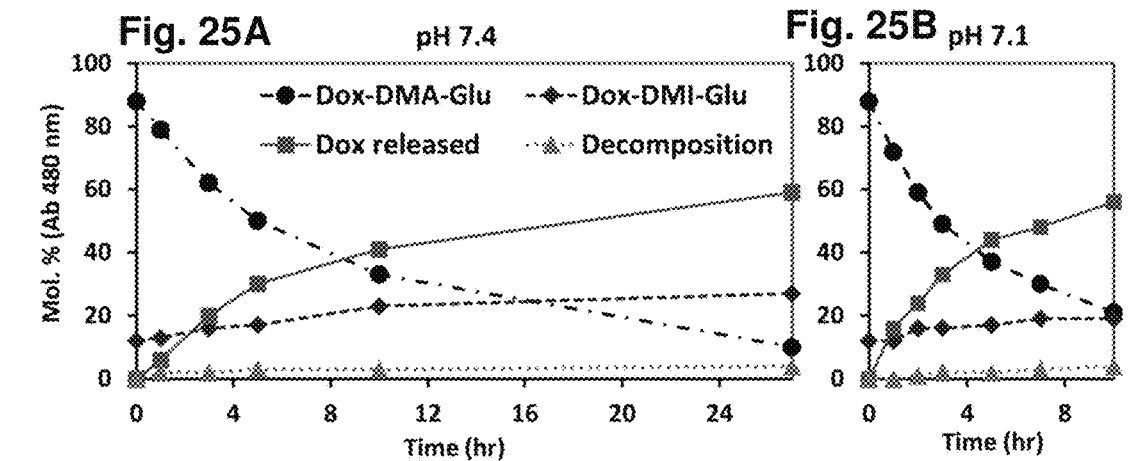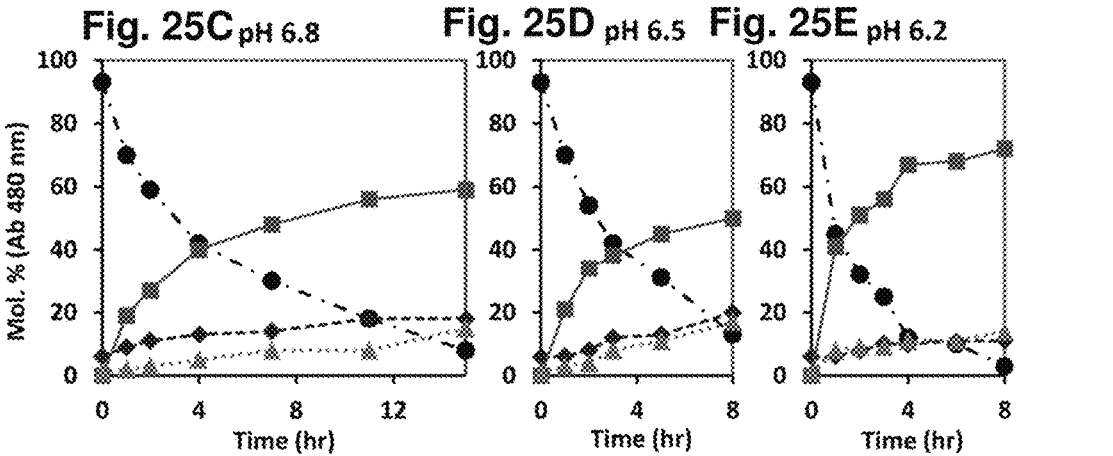

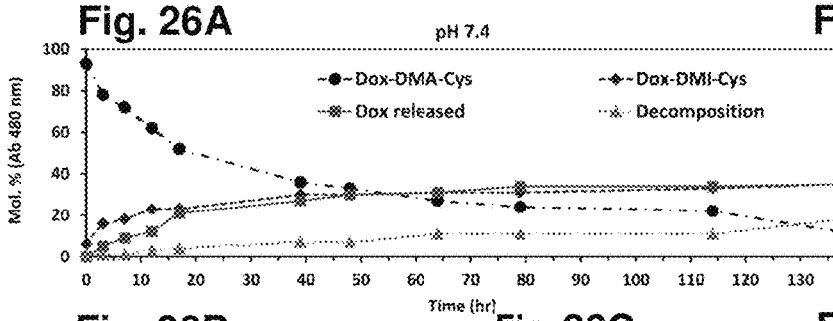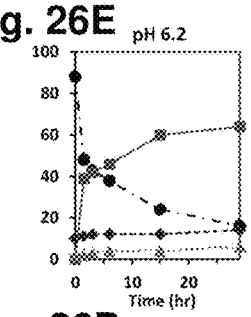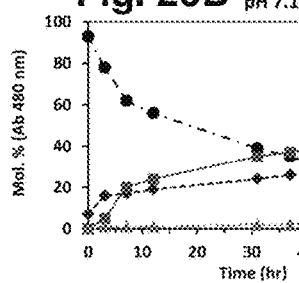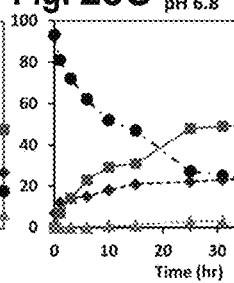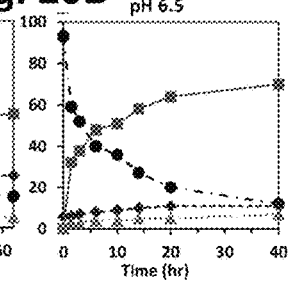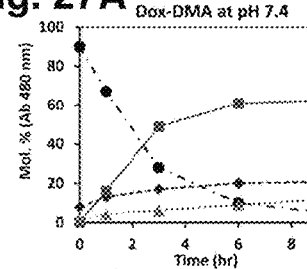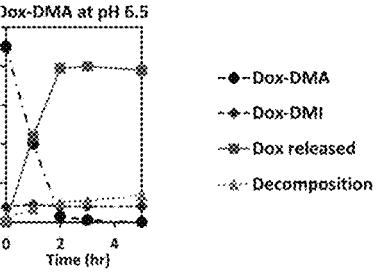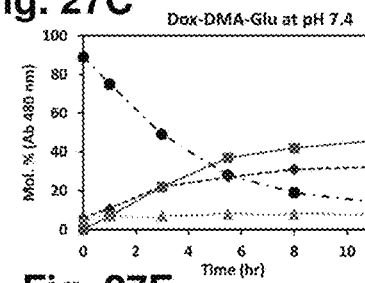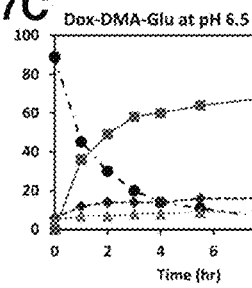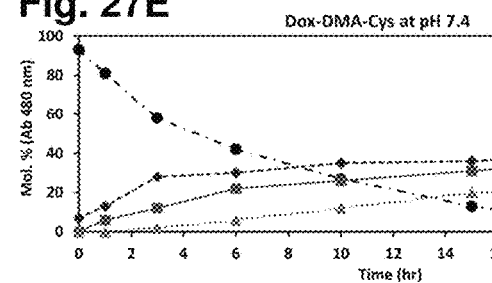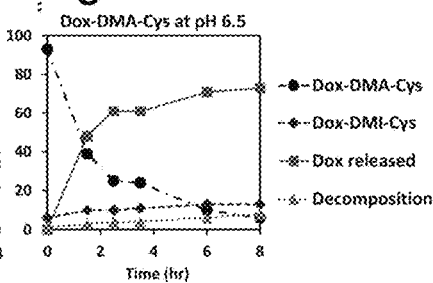

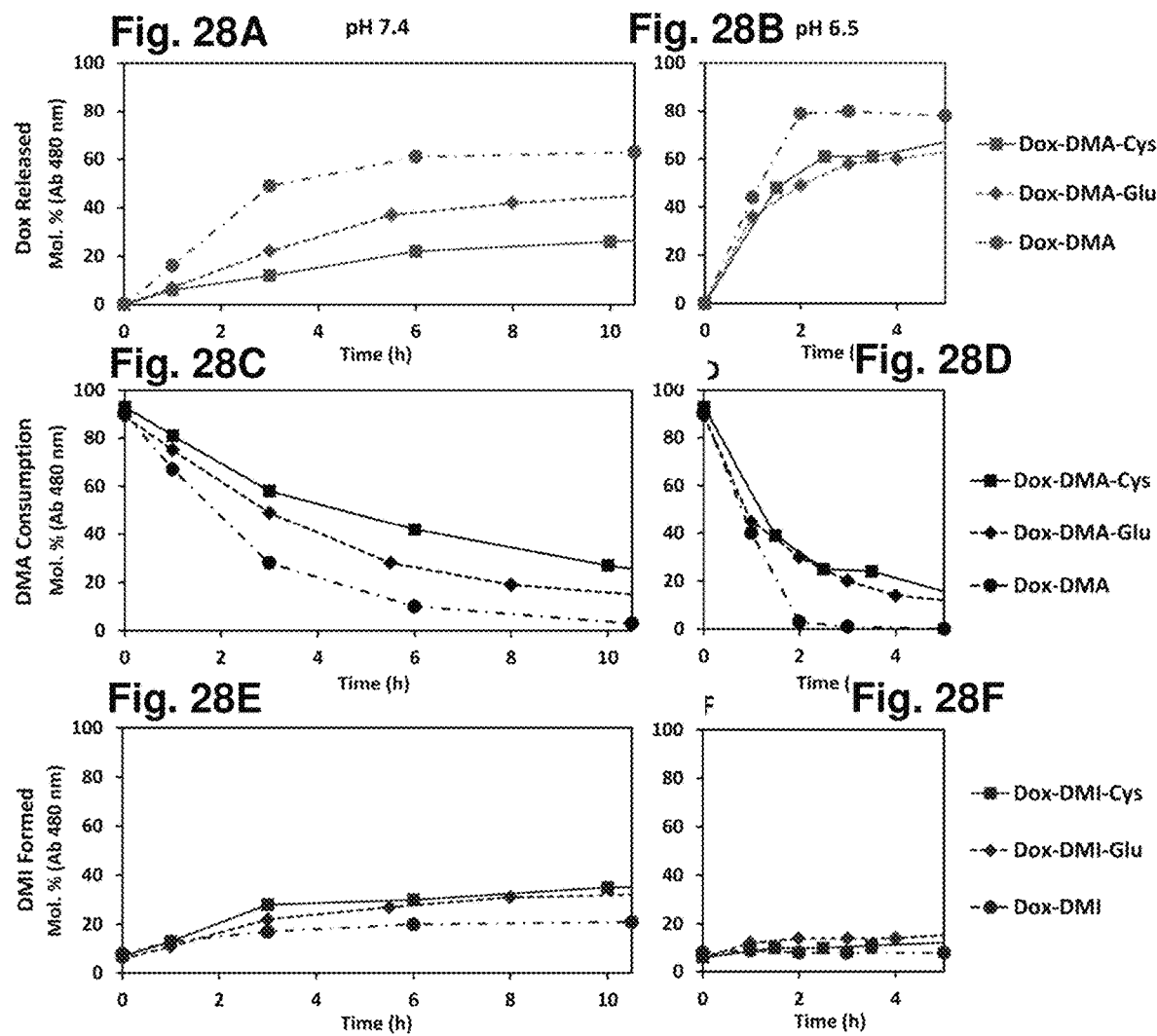

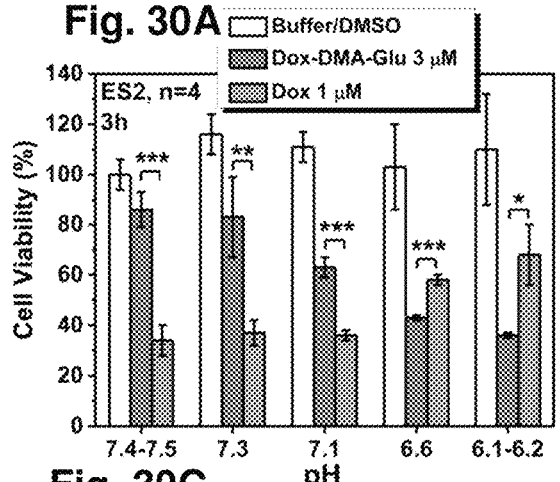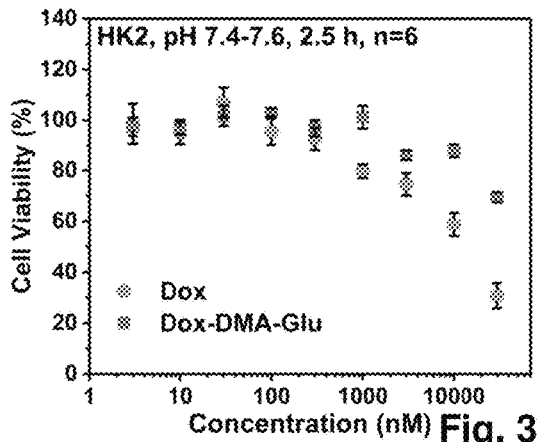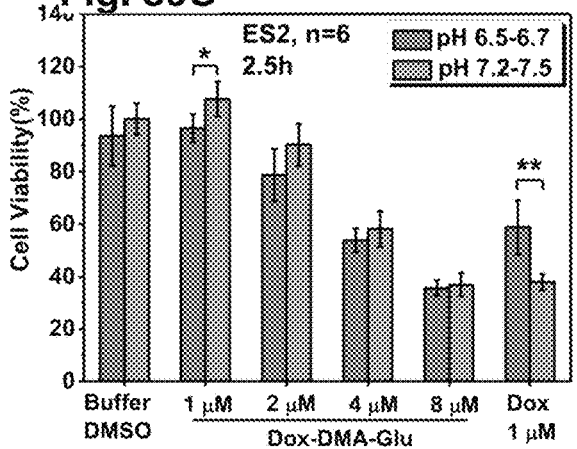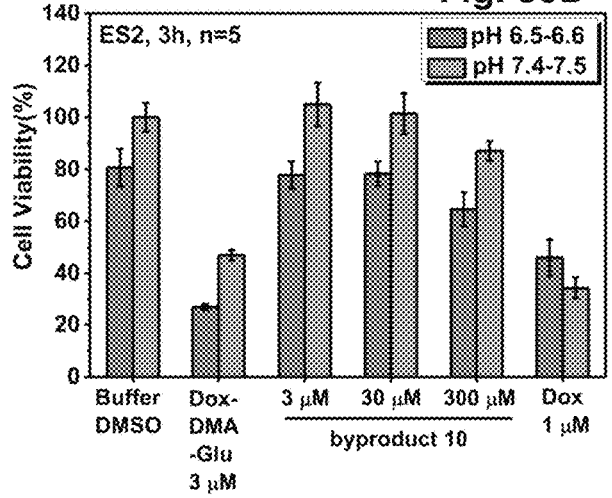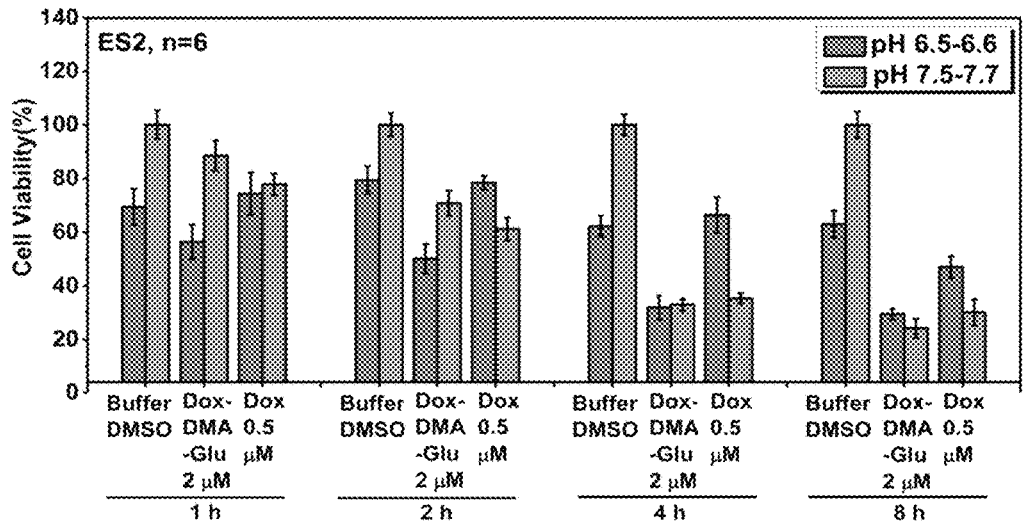

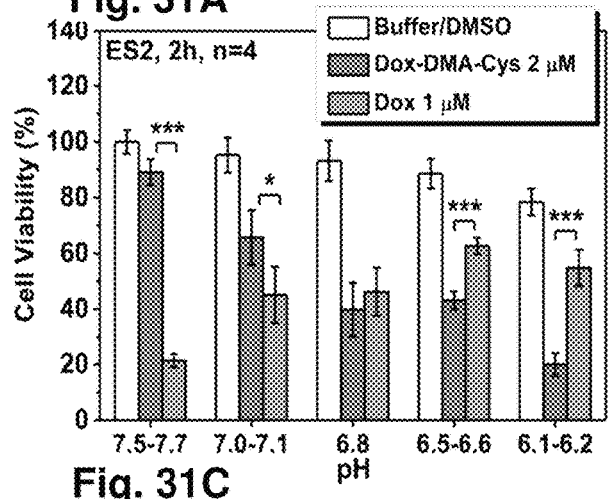
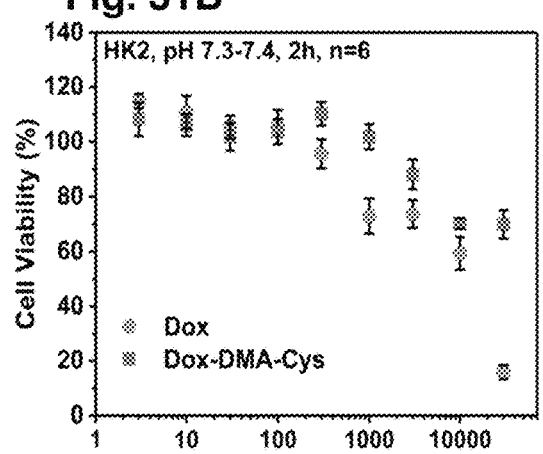
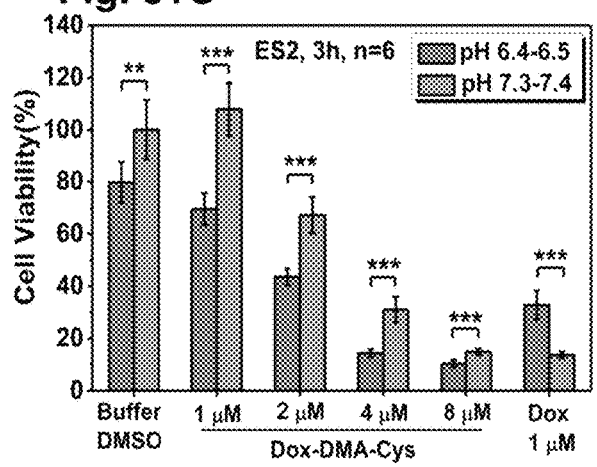
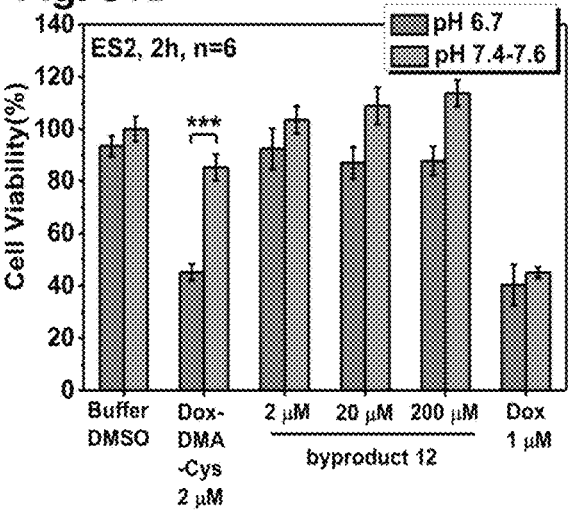
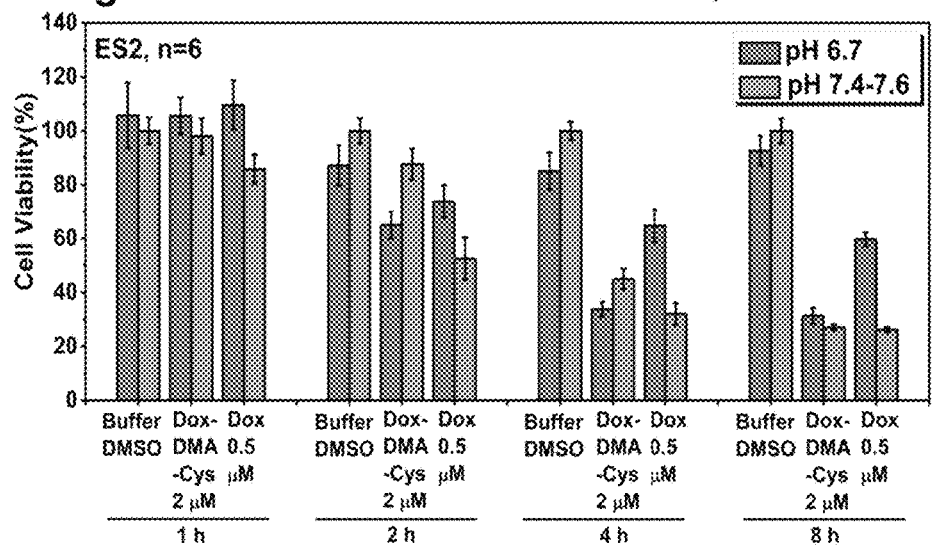

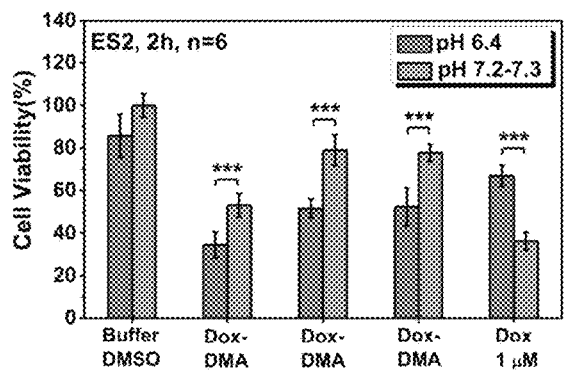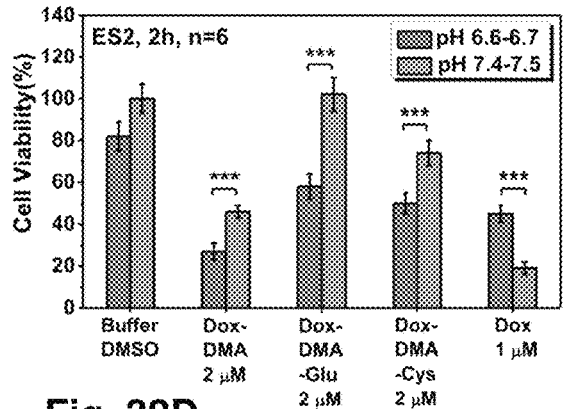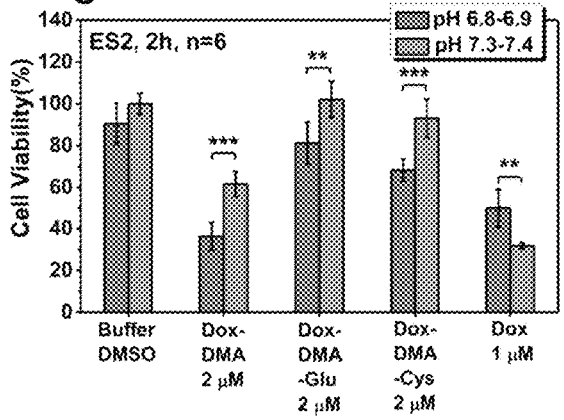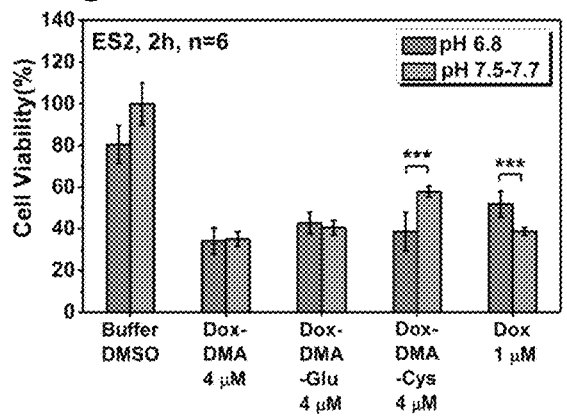
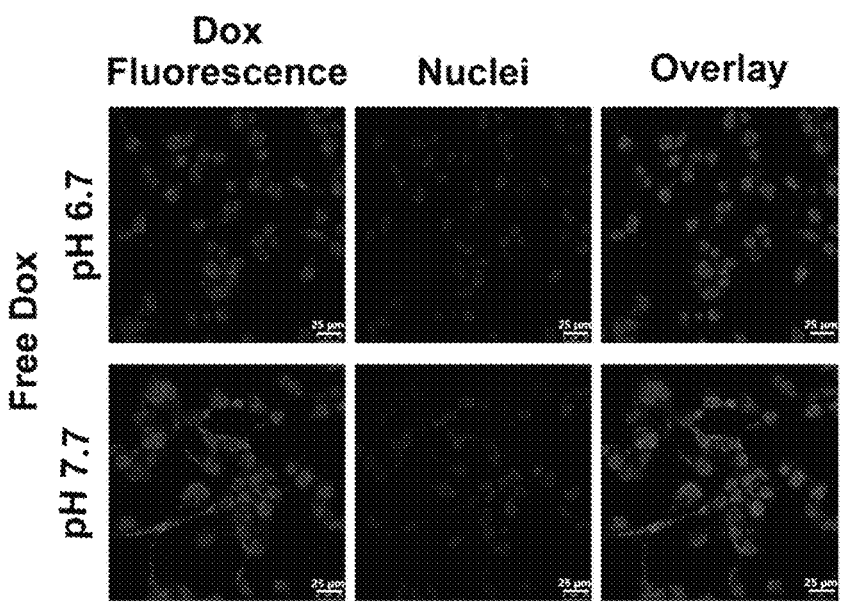
Fig. 33

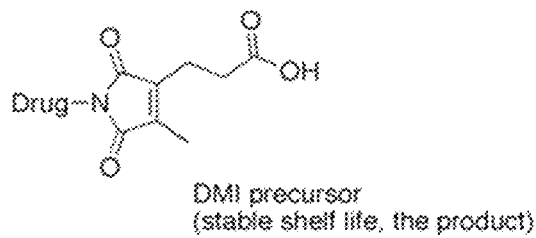
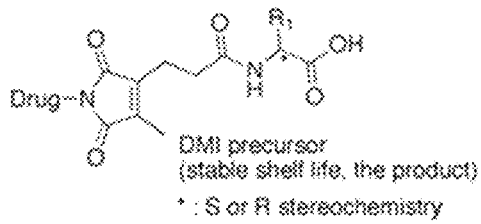
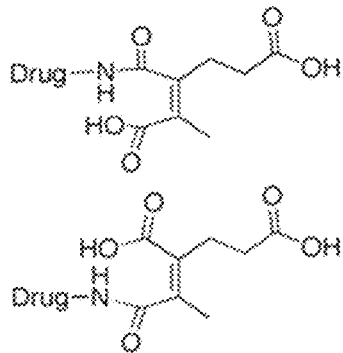
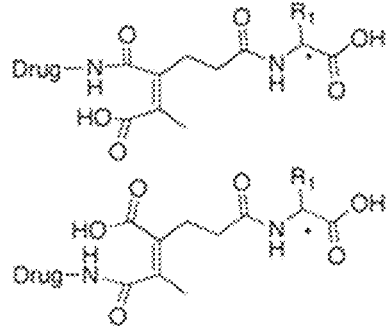
Fig. 37
Fig. 38
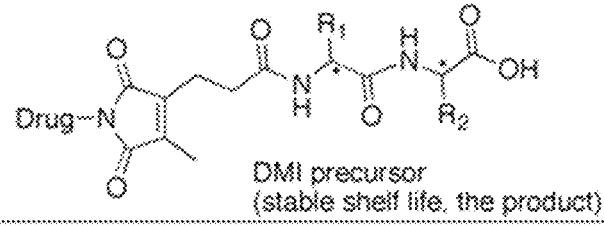
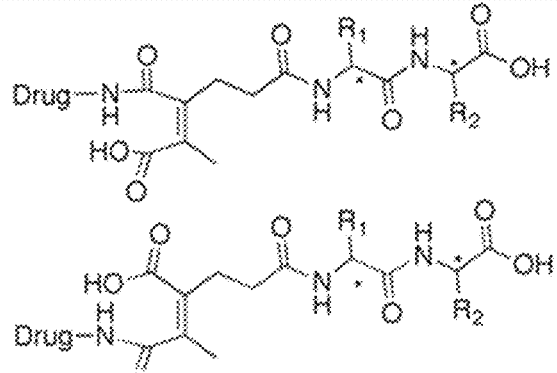
Fig. 39

DMA prodrugs of Dox and corresponding DMI pre-prodrugs

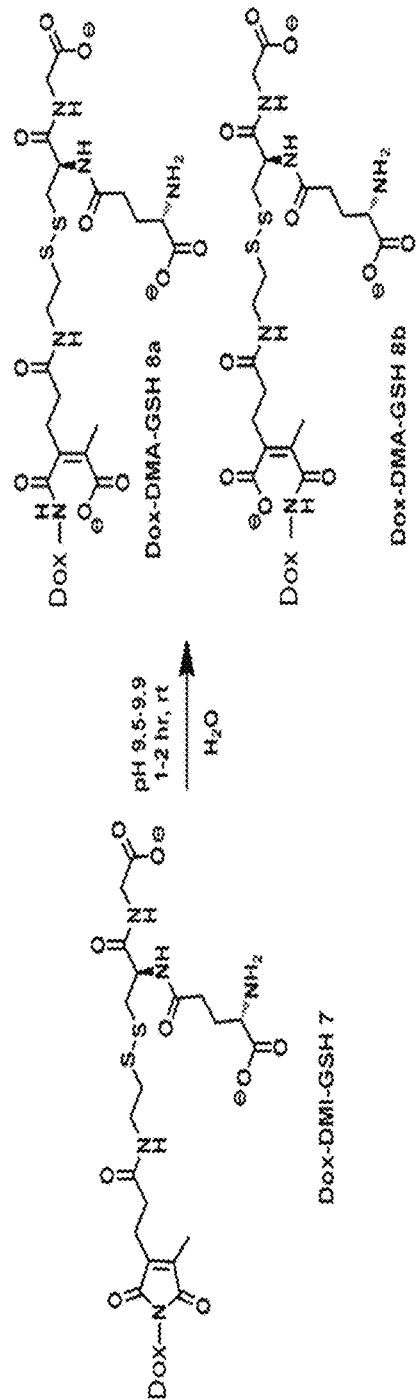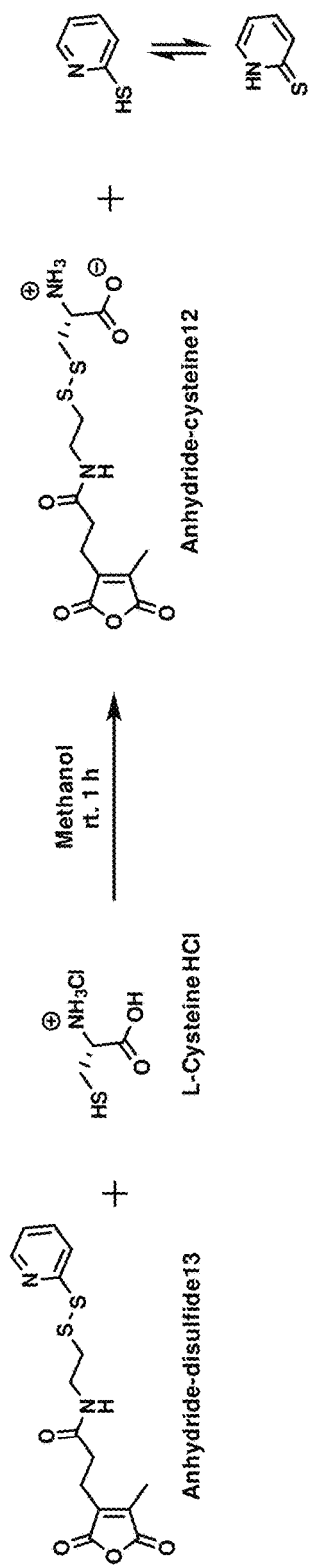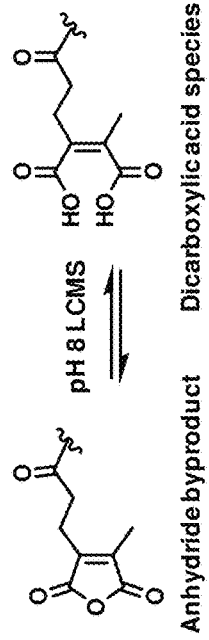
Fig. 45
Fig. 46
Fig. 47

REVERSING THE UNDESIRABLE PH-PROFILE OF DOXORUBICIN VIA ACTIVATION OF A DISUBSTITUTED MALEAMIC ACID PRODRUG AT TUMOR ACIDITY

CROSS REFERENCE TO RELATED APPLICATIONS

The present application is a non-provisional of, and claims priority under 35 U.S.C. § 119(e) from, U.S. Provisional Patent Application No. 62/928,143, filed Oct. 30, 2019, the entirety of which is expressly incorporated herein by reference.

FIELD OF THE INVENTION

The present invention relates to the field of protected prodrugs, and more particularly to pH responsive soluble drug delivery systems.

BACKGROUND OF THE INVENTION

Each reference cited herein is expressly incorporated herein by reference in its entirety.

The acid-labile behavior of disubstituted maleamic acid (DMA) and its equilibrium with di-substituted maleimide (DMI) are exploited to build an ultra acid-sensitive, small molecule prodrug that can be activated by tumor extracellular pH (pHe) in the range of 6.5-6.9. Such a DMA prodrug reversed the unfavorable pH-profile of doxorubicin (Dox), which may improve its therapeutic window.

Compared to a pHe of 7.2-7.6 in healthy tissues, many cancerous tumors are acidic with pHe values in the range of 6.5-6.9. [Tannock 1989, Gerweck 1996, Zhang 2010] Previous efforts in targeting tumor acidosis for drug delivery have focused on complex polymer nanoparticles. [Lee 2008, Lee 2005, Du 2011, Sun 2016] In contrast pH-sensitive small molecule prodrugs are now developed, which may have the following advantages: (a) their simple, chemically defined structures can more easily meet Good Manufacturing Practice standards, which is a significant difficulty [Farokhzad 2006] in nano-medicine; (b) their extracellular drug release mechanism is straightforward, while the endosomal trapping of the drug payload is a major concern for nanoparticle drug carriers; [Farokhzad 2006] (c) the pH-response may be more easily tuned via structure-activity relationship studies in small prodrugs.

Conventional chemotherapy treatments expose the whole body to cytotoxic, cancer-fighting drugs, causing fatal damage to healthy tissues. Due to increased metabolism, poor drainage, and the preference to use glycolysis for energy production (the Warburg effect), most solid tumors have a slightly acidic microenvironment with interstitial pHe in the range of 6.5-6.9, compared to pHe of 7.2-7.4 for healthy tissues. This acidotic pHe of tumors can be used for controlled release of chemotherapy drugs (chemo-drugs) via site-specific activation of prodrugs.

Nanomedicines such as the liposomal formulation of Dox (e.g. Doxil) and albumin-bound paclitaxel (Abraxane) can target tumors by the Enhanced Permeation and Retention (EPR) effect. Such nanoformulations of chemo-drugs have shown clinical benefits in reducing side-effects, illustrating the need to improve chemo-drugs for more targeted therapy. Small molecule prodrugs that attach chemo-drugs to pH-responsive moieties can be an alternative approach. Advantages of small molecule prodrugs are their small size which enables fast penetration into solid tumors, its non-immunogenic nature, and easy synthesis. Many pH-sensitive linkers have been used for the selective release of therapeutics at lysosomal pH (4-6); however, they are not sensitive enough to respond to tumor pHe.

Dox is a prominent and representative anthracycline chemo-drug widely used in the treatments of various malignancies. The acid-labile DMA linker can be used for fast, pH-selective release of Dox at tumor pHe, and its equilibrium with the ring-closed DMI form offers a way to overcome DMA instability during prodrug synthesis and storage.

Dox is an effective cancer chemotherapy drug with severe myocardial side effects. [Minotti 2004, LeFrak 1973] Dox intercalates into DNA and inhibits topoisomerase II. [Minotti 2004, Tewey 1984] To kill cancer cells Dox molecules must cross the plasma membrane and accumulate in the nucleus. The amino group of Dox is protonated with a pKa value of 8.2. [Skovsgaard 1977] Low tumor pHe values can impede the cellular uptake of Dox by increasing the proportion of the drug in the protonated ammonium form, which is positively charged and membrane impermeable. [Born 1981, Gerweck 1999, Gerweck 2006] Thus, Dox is more cytotoxic at a pHe of 7.4 than at 6.5, which may reduce drug efficacy and exacerbate side effects. Other amine chemotherapy drugs (e.g., other anthracyclines, topotecan, Vinca alkaloids) also show a similarly poor pH-profile. [Tannock 1989, Gerweck 1996, Born 1981, Vukovic 1997, Reichert 2002, Wojtkowiak 2011] The DMA prodrug approach aims to offset the undesirable pH-profile by selective drug release in response to acidic tumor pHe. A polar modulator (e.g., glutathione in this study) is attached to Dox through an acid-labile DMA linker to make the prodrug membrane impermeable, and thus, inactive. The DMA linker can be cleaved by slight acidity at pH 6.5, [Rozema 2007, Maier 2012, Rozema 2003, Meyer 2008] and has been used in the context of polymers and proteins for pH-triggered charge reversal. [Du 2011, Sun 2016, Rozema 2007, Maier 2012, Rozema 2003, Meyer 2008] Due to the macromolecular context, chemical details of DMA formation, conjugate stability and pH-dependent cleavage are limited. Other acid-labile linkers, such as ketal, acetal, hemi-acetal, imine, hydrazone, mono-substituted maleamic acid (e.g., cis-aconityl) and spiro-diorthoester may respond to a lysosomal acidity of pH 4.5-6.0, but they are not sensitive enough to be triggered at tumor pHe. [Jacques 2016, Cao 2014, Leriche 2015] For amine drugs such as Dox, since DMA is an amide, it constitutes a natural traceless linker with a one-step conjugation chemistry.

The general scheme for the transformations between drug, prodrug and pre-prodrug are shown in FIG. 1. The synthesis of DMA prodrug 8 is outlined in more detail in FIG. 2. Acid 1 and acyl chloride 2 were prepared following the methods of Isobe. [Naganawa 1994] Acyl chloride 2 reacted with S-(2-pyridylthio)-cysteamine 3 to give crosslinker 4 in 50% yield from acid 1. This new compound 4 has general utility for crosslinking an amine with a thiol through DMA. Combining 4 with Dox quickly led to the formation of DMA regioisomers 5a/b in minutes, which slowly converted to the ring-closed DMI 6 over a period of days. Initial efforts were focused on using DMA 5a/b for further conjugation to the polar modulator glutathione (GSH). However, DMA 5a/b was difficult to handle or store due to its instability. If the DMA prodrug is similarly unstable, its direct practical use is in doubt. To circumvent this difficulty, Dox-DMI-GSH 7 is synthesized, and then convert it to DMA prodrug 8 immediately prior to use. Therefore, the reaction between Dox and anhydride 4 was allowed to proceed all the way to Dox- DMI-disulfide 6 with an isolated yield of 74%. Disulfide exchange between 6 and GSH (acid form) proceeded smoothly under acidic conditions to give Dox-DMI-GSH 7 in 70% yield. Side products arising from thiol attacking the maleimide via Michael addition or ring opening were not observed (FIG. S21 in ESI of Zhang, Anqi, Lan Yao, and Ming An. "Reversing the undesirable pH-profile of doxorubicin via activation of a di-substituted maleamic acid prodrug at tumor acidity." Chemical Communications 53, no. 95 (2017): 12826-12829, expressly incorporated herein by reference in its entirety, hereinafter Zhang et al. or "ESI". Electronic supplementary information (ESI) available: Tables S1-S4, FIGS. S1-S22, experimental details of DMA pro-drug synthesis, pH-dependent HPLC cleavage tests, and cell growth inhibition assays. See DOI: 10.1039/c7cc06843c). On the day DMA prodrug 8 was used in cleavage tests or cell assays, DMI 7 was treated with a pH 10 aq. buffer for 1 h at rt to provide the conjugate base of Dox-DMA-GSH 8a/b in a near quantitative fashion.

Subsequently, the pH of the prodrug 8 solution was adjusted to a desired value between 6.0 and 7.4 to evaluate how quickly Dox is released in response to slight acidity at rt (about 25° C.). DMA 8 consumption, Dox release, reversion to DMI 7, and background decomposition were followed over time using HPLC at pH 8 (FIG. S1 in ESI). At each time point, areas under the peaks were integrated to give the percentages reported in Table 1 in the ESI which are plotted in FIGS. S1A-F. After 24 h at pH 7.4, 19% of prodrug 8 released Dox while 23% ring-closed to DMI 7 (FIG. S1A).

At pH 6.5, the drug release was much faster with 43% of Dox appearing after only 6 h and 67% after 24 h (FIG. S1D). The overall data of Dox release and DMI 7 formation at different pH values are summarized in FIGS. S1G-S1I. Dox release showed clear pH dependence throughout the pH range whereas reversion to DMI 7 did not. When the drug release is slow at pH 7.4, the ring closure to DMI 7 is competitive, which can serve to 'switch off' the prodrug over time and reduce background drug release under physiological pHe conditions. The largest pH 6/7 cleavage ratio (at 25 1 C in aq. buffer) known previously is B4:1, achieved using a spiro diorthoester linker; [Jacques 2016] in comparison, DMA 8 improved this ratio to B7:1 (e.g., at 5 h, B70% of Dox is released at pH 6 vs. B10% at pH 7).

To better simulate drug release under in vivo conditions, HPLC cleavage tests were carried out at 37 1 C with or without fetal bovine serum (FBS). As shown in FIGS. S2A and S2B (also see FIG. S2 and Table 2 in the ESI), in aq. buffer, increasing the temperature to 37 1 C led to faster Dox release at both pH 6.5 (e.g., B70% at 3 h) and 7.4 (B20% at 3 h), yet the pH 6.5/7.4 ratio remained B3-4 fold. When DMA 8 was exposed to 45% FBS in DMEM-F12 cell medium at 37 1 C, after 6 h, B60% of Dox was released at pH 6.5 compared to only B10% at pH 7.4 (FIGS. S2C and S2D, also see FIG. S3 and Table 3 in the ESI). This 6:1 ratio largely reflects the suppression of Dox release at pH 7.4 (i.e., B30% without FBS vs. B10% with FBS, FIG. S2A vs. FIG. S2C) by serum-induced decomposition of DMA 8 (B25% without FBS vs. B45% with FBS). At pH 7.4, DMA 8 mostly decomposed without releasing Dox, while at pH 6.5, it mostly cleaved to release Dox. Thus, the large difference in drug release within the narrow pH range is accomplished through the combination of 'switch-on' (i.e., DMA cleavage) and 'switch-off' (i.e., DMI formation and other degradation) mechanisms.

Possible equilibriums that govern pH-dependent drug release are depicted in FIG. 1. The acid form of DMA 8 which is more viable at lower pH, has at least three modes of reactivity leading to drug release. In Mode A, as proposed by Kirby and Lancaster, [Kirby 1972] intramolecular proton transfer from carboxylic acid to amide followed by ring closure leads to the tetrahedral intermediate (TI) 10. Breakdown of TI 10 into amine (Dox) and anhydride 9 completes drug release (this is likely the main mechanism). The rate of amide hydrolysis is B700-fold faster when there are two instead of one alkyl substituent on the maleamic acid double bond, [Kirby 1972] as the steric congestion of the two alkyl groups forces the reacting carboxyl and amide partners into a perfect near attack conformation. Protonation of TI 10 is needed for breakdown, which may further contribute to the pH-dependence of drug release. Alternatively, ring-closure from the DMA conjugate base to 12 may also lead to Dox release via TI 10 upon protonation. As shown in this study, considerable amounts of DMI 7 were formed from DMA 8. Thus, attack on the carboxyl by the amide N atom must also be possible due to their close proximity (Mode C). If so, then similar attack by the amide O atom may also be possible (Mode B), which can lead to isomaleimide 13. The DMI 7 isolated is not isomaleimide 13 because it is stable under acidic aqueous conditions (pH 2-3). However, acid-catalyzed hydrolysis of isomaleimide 13 may also contribute to Dox release via TI 10.

In cancer patients, following intravenous administration of a dose of Dox over 5-40 min, the initial plasma concentration is in the range of 1-10 mM. [Lee 1980, Bruijn 1999] The Dox half-life in plasma is only 5-10 min as the drug is rapidly distributed into tissues. [Lee 1980, Bruijn 1999] Two hours afterwards the intratumoral concentration of Dox is mostly in the range of 0.5-5 mM. [Lee 1980] Pharmacokinetics (PK) studies suggest that (a) for Dox en route to reaching its DNA target, the slowest step is crossing the plasma membrane, which is pHe-dependent, (b) peak intracellular Dox concentration is achieved over a few hours and this parameter is most critical for antitumor efficacy, and (c) the infusion duration should be 1-3 h to maximize drug concentration in cancer cells. [El-Kareh 2000] Cell experiments were carried out under conditions that reflect these Dox PK parameters. To confirm the free drug pH-profile, Dox was tested in a variety of cancer cells (i.e., ovarian cancer: ES-2, OVCAR3, SKOV3; breast cancer: MDA-MB231; prostate cancer: PC-3). Indeed, Dox was universally more cytotoxic at pHe 7.2-7.6 than at 6.5-7.0 over a wide range of PK-relevant concentrations (0.1-4 mM) and time frames (2-24 h), and often by as much as 2-3 fold (FIG. S3, also see the ESI, FIGS. S4-S7).

To test the prodrug, ES-2 cells were treated for 6 h with DMA 8 at pHe 6.7 or 7.4 (FIG. 7A). Compared to 0.5 mM of free Dox, 1 mM of prodrug was more potent at pHe 6.7 but about 3-fold less cytotoxic at pHe 7.4. In terms of the pH-profile, the prodrug was B2-fold more potent at pHe 6.7 while the free drug was the opposite, i.e., B2-fold more potent at pHe 7.4. This effect of pH-profile reversal diminished when treatments lasted longer than 6 h (ESI, FIG. S6). Compared to DMA 8, DMI 7 showed much less toxicity (FIG. 7A, also see the ESI, FIG. S5) while byproduct 9 was completely nontoxic even at a concentration of 200 mM (FIG. S8 in ESI). Next the pH-profile of prodrug 8 was tested in shorter 2-3 h experiments, a time frame more relevant to Dox PK. [El-Kareh 2000] To inhibit the growth of MDA-MB231 and OVCAR3 cancer cells, 3 µM of free Dox was needed; accordingly, 6-8 µM of prodrug 8 showed 2-3× higher potency than the free drug at pHe 6.3-6.4 while being 2-4× less cytotoxic at pHe 7.5-7.6 (FIGS. 7B and 7C). Similar results were also obtained with PC-3 and SKOV3 cells (ESI, FIG. S5). To characterize the pH-profile reversal in a more systematic fashion, ES-2 cells were treated with Dox or DMA 8 at pHe 6.7 or 7.4 for 2.5 h at concentrations ranging from 3 nM to 30 µM. The dose response curves are shown in FIG. S7 in the ESI, which gave prodrug $IC_{50}$ values of 2.1±0.3 mM at pHe 6.7 and 3.2±0.4 mM at pHe 7.4, compared with free Dox $IC_{50}$ values of 1.6±0.1 mM at pHe 6.7 and 0.7±0.1 mM at pHe 7.4 (FIG. 7D).

To further gauge the benefit of prodrug 8 at tumor acidity, pHe titration experiments were performed. For the ES-2 cells, the maximum effect was reached at pHe 6.8 (FIG. 7E), which matches the average tumor acidity in patients. In MDA-MB231 and OVCAR3 cells, maximum effects were seen at pHe 6.5 (FIGS. 7F and 7G). Importantly, the presence of 50% serum can indeed enhance the pH-profile reversal effect of prodrug 8 (FIG. 7I), consistent with the cleavage data shown in FIG. S2. Finally, to simulate the effect of the drug vs. prodrug in off-target healthy tissues, noncancerous kidney epithelial HK2 cells were treated with Dox or DMA 8 at pHe 7.4 (FIG. 7H), which demonstrates that prodrug 8 is also much less toxic than free Dox towards non-cancerous cells (by 30-fold in concentration).

The DMA prodrug approach was made possible by the equilibrium between DMA and its ring-closed DMI form: (a) the DMI can serve as a convenient synthetic precursor for the unstable DMA prodrug; and (b) conversely, DMI formation from DMA limits the background drug release at pH 7.4 by 'switching off' the prodrug. In cleavage tests at 37° C. with 45% serum, prodrug 8 released 6-fold more Dox at pH 6.5 than at 7.4, which demonstrates that DMA is likely the most acid-labile linker suitable for use in biological settings. In cell culture experiments, prodrug 8 dramatically reversed the undesirable pH-profile of free Dox. Thus, the DMA prodrug approach holds promise for improving Dox chemotherapy.

The published work employs a linker having a disulfide linkage, which is labile, redox-responsive, and subject to exchange reactions. In particular, anthracycline antibiotics tend to be free radical inducers, which would be expected to react with the sulfur. Further, synthesis yield was low, e.g., ~25%, and the hydrolysis rate (drug delivery) is temperature sensitive.

Further, the glutathione moiety has a specific physiology, which can interact with the prodrug, and lead to off-target toxicity.

The tumor microenvironment (TME) is the cellular environment in which the tumor exists, including surrounding blood vessels, immune cells, fibroblasts, bone marrow-derived inflammatory cells, lymphocytes, signaling molecules and the extracellular matrix (ECM). [Tannock 1989, Gerweck 1996, Zhang 2010] The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells. [Lee 2008]

The tumor microenvironment contributes to tumor heterogeneity. en.wikipedia.org/wiki/Tumor_microenvironment.

The tumor microenvironment is often hypoxic. As the tumor mass increases, the interior of the tumor grows farther away from existing blood supply. While angiogenesis can reduce this effect, the partial pressure of oxygen is below 5 mm Hg (venous blood has a partial pressure of oxygen at 40 mm Hg) in more than 50% of locally advanced solid tumors. The hypoxic environment leads to genetic instability, which is associated with cancer progression, via downregulating DNA repair mechanisms such as nucleotide excision repair (NER) and mismatch repair (MMR) pathways. Hypoxia also causes the upregulation of hypoxia-inducible factor 1 alpha (HIF1-α), which induces angiogenesis and is associated with poorer prognosis and the activation of genes associated with metastasis, leading, for instance, to increased cell migration and also ECM remodeling.

While a lack of oxygen can cause glycolytic behavior in cells, tumor cells also undergo aerobic glycolysis, in which they preferentially produce lactate from glucose even given abundant oxygen, called the Warburg effect. No matter the cause, this leaves the extracellular microenvironment acidic (pH 6.5-6.9), while the cancer cells themselves are able to remain neutral (pH 7.2-7.4). It has been shown that this induces greater cell migration in vivo and in vitro, possibly by promoting degradation of the ECM.

The Warburg effect refers to the observation that cancer cells tend to favor metabolism via anaerobic glycolysis rather than the much more efficient oxidative phosphorylation pathway, which is the preference of most other cells of the body. Normal cells primarily produce energy through mitochondrial oxidative phosphorylation. However, most cancer cells predominantly produce their energy through a high rate of glycolysis followed by lactic acid fermentation even in the presence of abundant oxygen. Aerobic glycolysis is less efficient than oxidative phosphorylation in terms of adenosine triphosphate production, but leads to the increased generation of additional metabolites that may particularly benefit proliferating cells.

Tumor M2-PK, a form of the pyruvate kinase enzyme, gives rise to the Warburg effect. Tumor M2-PK is produced in all rapidly dividing cells, and is responsible for enabling cancer cells to consume glucose at an accelerated rate; on forcing the cells to switch to pyruvate kinase's alternative form by inhibiting the production of tumor M2-PK, their growth was curbed. High glucose levels have been shown to accelerate cancer cell proliferation in vitro, while glucose deprivation has led to apoptosis. These findings have initiated further study of the effects of carbohydrate restriction on tumor growth. Clinical evidence shows that lower blood glucose levels in late-stage cancer patients have been correlated with better outcomes.

Allen, Theresa M. "Ligand-targeted therapeutics in anticancer therapy." Nature Reviews Cancer 2, no. 10 (2002): 750.

Bacalocostantis, Irene, Viraj P. Mane, Michael S. Kang, Addison S. Goodley, Silvia Muro, and Peter Kofinas. "Effect of thiol pendant conjugates on plasmid DNA binding, release, and stability of polymeric delivery vectors." Biomacromolecules 13, no. 5 (2012): 1331-1339.

Bae, Younsoo, Nobuhiro Nishiyama, and Kazunori Kataoka. "In vivo antitumor activity of the folate-conjugated pH-sensitive polymeric micelle selectively releasing adriamycin in the intracellular acidic compartments." Bioconjugate chemistry 18, no. 4 (2007): 1131-1139.

Batra, Surabhi, Kehinde U. A. Adekola, Steven T. Rosen, and Mala Shanmugam. "Cancer Metabolism as a Therapeutic Target." Oncology (Williston Park, N.Y.) 27, no. 5 (May 2013): 460-67.

Bertram J S (December 2000). "The molecular biology of cancer". Molecular Aspects of Medicine. 21 (6): 167-223. doi:10.1016/0098-2997(00)00007-8. PMID 11173079.

Bindra, Ranjit S.; Glazer, Peter M. (Jan. 6, 2005). "Genetic instability and the tumor microenvironment: towards the concept of microenvironment-induced mutagenesis". Mutation Research/Fundamental and Molecular Mechanisms of Mutagenesis. 569 (1-2): 75-85. doi:10.1016/j.mrfmmm.2004.03.013. PMID 15603753.

Blagosklonny, Mikhail V. (January 2004). "Antiangiogenic therapy and tumor progression". Cancer Cell. 5 (1): 13-17. doi:10.1016/S1535-6108(03)00336-2. Retrieved June 2015.

Blattler, Walter A., John M. Lambert, and Peter D. Senter. "Acid-cleavable compound, use in protein conjugates and drug delivery systems." U.S. Pat. No. 4,569,789, issued Feb. 11, 1986.

Bonnet S, Archer S L, Allalunis-Turner J, Haromy A, Beaulieu C, Thompson R, Lee C T, Lopaschuk G D, Puttagunta L, Bonnet S, Harry G, Hashimoto K, Porter C J, Andrade M A, Thebaud B, Michelakis E D (January 2007). "A mitochondria-K+ channel axis is suppressed in cancer and its normalization promotes apoptosis and inhibits cancer growth". Cancer Cell. 11 (1): 37-51. doi:10.1016/j.ccr.2006.10.020. PMID 17222789.

Born R., and H. Eichholtz-Wirth, Br. J. Cancer, 1981, 44, 241.

Bustamante E, Pedersen P L (September 1977). "High aerobic glycolysis of rat hepatoma cells in culture: role of mitochondrial hexokinase". Proceedings of the National Academy of Sciences of the United States of America. 74 (9): 3735-9. Bibcode:1977PNAS . . . 74.3735B. doi:10.1073/pnas.74.9.3735. PMC 431708. PMID 198801.

Cajot, Sébastien. "Tailor-made degradable copolymers for the design of advanced drug delivery systems." PhD diss., University of Liege (ULg), Belgium, 2012.

Cao, Y., and J. Yang, Bioconjugate Chem., 2014, 25, 873.

Christofk H R, Vander Heiden M G, Harris M H, Ramanathan A, Gerszten R E, Wei R, Fleming M D, Schreiber S L, Cantley L C (March 2008). "The M2 splice isoform of pyruvate kinase is important for cancer metabolism and tumour growth". Nature. 452 (7184): 230-3. Bibcode:2008Natur. 452 . . . 230C. doi:10.1038/nature06734. PMID 18337823.

Clinical trial number NCT00633087 for "A Phase I/II Trial of 2-Deoxyglucose (2DG) for the Treatment of Advanced Cancer and Hormone Refractory Prostate Cancer (2-Deoxyglucose)" at ClinicalTrials.gov Colen C B (2005). Gene therapy and radiation of malignant glioma by targeting glioma specific lactate transporter (Ph.D.). Wayne State University.

Colen C B, Seraji-Bozorgzad N, Marples B, Galloway M P, Sloan A E, Mathupala S P (December 2006). "Metabolic remodeling of malignant gliomas for enhanced sensitization during radiotherapy: an in vitro study". Neurosurgery. 59 (6): 1313-23, discussion 1323-4. doi:10.1227/01.NEU.0000249218.65332.BF. PMC 3385862. PMID 17277695.

Colen C B, Shen Y, Ghoddoussi F, Yu P, Francis T B, Koch B J, Monterey M D, Galloway M P, Sloan A E, Mathupala S P (July 2011). "Metabolic targeting of lactate efflux by malignant glioma inhibits invasiveness and induces necrosis: an in vivo study". Neoplasia. 13 (7): 620-32. doi:10.1593/neo.11134. PMC 3132848. PMID 21750656.

Danhier, Fabienne; Feron, Olivier; Préat, Vdronique (Dec. 1, 2010). "To exploit the tumor microenvironment: Passive and active tumor targeting of nanocarriers for anti-cancer drug delivery". Journal of Controlled Release. 148 (2): 135-146. doi:10.1016/j.jconrel.2010.08.027. Retrieved June 2015.

de Bruijn, P., J. Verweij, W. J. Loos, H. J. Kolker, A. S. Planting, K. Nooter, G. Stoter and A. Sparreboom, Anal. Biochem., 1999, 266, 216.

Du, J. Z., X. J. Du, C. Q. Mao and J. Wang, J. Am. Chem. Soc., 2011, 133, 17560.

Duncan, Ruth. "The dawning era of polymer therapeutics." Nature reviews Drug discovery 2, no. 5 (2003): 347.

Ebright, Y. W., Y. Chen, P. S. Pendergrast and R. H. Ebright, Biochemistry, 1992, 31, 10664.

El-Kareh, A. W., and T. W. Secomb, Neoplasia, 2000, 2, 325.

Estrella, Veronica; Chen, Tingan; Lloyd, Mark; Wojtkowiak, Jonathan; Cornnell, Heather H.; Ibrahim-Hashim, Arig; Bailey, Kate; Balagurunathan, Yoganand; Rothberg, Jennifer M.; Sloane, Bonnie F.; Johnson, Joseph; Gatenby, Robert A.; Gillies, Robert J. (1 Mar. 2013). "Acidity Generated by the Tumor Microenvironment Drives Local Invasion". Cancer Research. 73 (5): 1524-1535. doi:10.1158/0008-5472.CAN-12-2796. PMC 3594450. PMID 23288510. Retrieved June 2015.

Farokhzad, Omid C., and Robert Langer. "Impact of nanotechnology on drug delivery." ACS nano 3, no. 1 (2009): 16-20.

Farokhzad, Omid C., Jianjun Cheng, Benjamin A. Teply, Ines Sherifi, Sangyong Jon, Philip W. Kantoff, Jerome P. Richie, and Robert Langer. "Targeted nanoparticle-aptamer bioconjugates for cancer chemotherapy in vivo." Proceedings of the National Academy of Sciences 103, no. 16 (2006): 6315-6320.

Gatenby, Robert A.; Gillies, Robert J. (November 2004). "Why do cancers have high aerobic glycolysis?". Nature Reviews Cancer. 4 (11): 891-899. doi:10.1038/nrc1478. PMID 15516961.

Gerweck, L. E., and K. Seetharaman, *Cancer Res.*, 1996, 56, 1194. 3

Gerweck, L. E., S. V. Kozin and S. J. Stocks, Br. J. Cancer, 1999, 79, 838.

Gerweck, L. E., S. Vijayappa and S. Kozin, Mol. Cancer Ther., 2006, 5, 1275.

Gogvadze, Vladimir, Boris Zhivotovsky, and Sten Orrenius. "The Warburg effect and mitochondrial stability in cancer cells." Molecular aspects of medicine 31, no. 1 (2010): 60-74. doi:10.1016/j.mam.2009.12.004. ISSN 0098-2997.

Grandér D (April 1998). "How do mutated oncogenes and tumor suppressor genes cause cancer?". Medical Oncology. 15 (1): 20-6. doi:10.1007/BF02787340. PMID 9643526.

Gupta V, Gopinath P, Iqbal M A, Mazurek S, Wellen K E, Bamezai R N (2013). "Interplay between epigenetics & cancer metabolism". Current Pharmaceutical Design. 20 (11): 1706-14. doi:10.2174/13816128113199990536. PMID 23888952.

Hamman, Josias H. "Chitosan based polyelectrolyte complexes as potential carrier materials in drug delivery systems." Marine drugs 8, no. 4 (2010): 1305-1322.

Harami-Papp H, Pongor L S, Munkácsy G, Horváth G, Nagy ÁM, Ambrus A, Hauser P, Szabó A, Tretter L, Győrffy B (October 2016). "TP53 mutation hits energy metabolism and increases glycolysis in breast cancer". Oncotarget. 7 (41): 67183-67195. doi:10.18632/oncotarget.11594. PMC 5341867. PMID 27582538.

He, Nan, Zhoujiang Chen, Jiang Yuan, Long Zhao, Maohua Chen, Tao Wang, and Xiaohong Li. "Tumor pH-Responsive Release of Drug-Conjugated Micelles from Fiber Fragments for Intratumoral Chemotherapy." ACS applied materials & interfaces 9, no. 38 (2017): 32534-32544.

He, Xi, Jianfeng Li, Sai An, and Chen Jiang. "pH-sensitive drug-delivery systems for tumor targeting." Therapeutic delivery 4, no. 12 (2013): 1499-1510.

Henry, Scott M., Mohamed E H El-Sayed, Christopher M. Pirie, Allan S. Hoffman, and Patrick S. Stayton. "pH-responsive poly (styrene-alt-maleic anhydride) alkylamide copolymers for intracellular drug delivery." Biomacromolecules 7, no. 8 (2006): 2407-2414.

Huh, Kang Moo, Han Chang Kang, Young Ju Lee, and You Han Bae. "pH-sensitive polymers for drug delivery." Macromolecular research 20, no. 3 (2012): 224-233.

Ibrahim, Khalid E., Amel O. Bakhiet, Ayaat Khan, and Haseeb A. Khan. "Recent Trends in Biomedical Applications of Nanomaterials." Biosciences Biotechnology Research Asia 15, no. 2 (2018).

Jacques, S. A., G. Leriche, M. Mosser, M. Nothisen, C. D. Muller, J. S. Remy and A. Wagner, Org. Biomol. Chem., 2016, 14, 4794. 24

Kamada, Haruhiko, Yasuo Tsutsumi, Yasuo Yoshioka, Yoko Yamamoto, Hiroshi Kodaira, Shin-ichi Tsunoda, Takayuki Okamoto et al. "Design of a pH-sensitive polymeric carrier for drug release and its application in cancer therapy." Clinical Cancer Research 10, no. 7 (2004): 2545-2550.

Kang, Sunyoung, Euddeum Park, Youngeun Kim, Seonju Lee, Jiwoong Kwon, Hyungdo Cho, and Yan Lee. "A medusa-like β-cyclodextrin with 1-methyl-2-(2'-carboxyethyl) maleic anhydrides, a potential carrier for pH-sensitive drug delivery." Journal of drug targeting 22, no. 7 (2014): 658-668.

Kang, Sunyoung, Youngeun Kim, Youngjun Song, Jin Uk Choi, Euddeum Park, Wonmin Choi, Jeongseon Park, and Yan Lee. "Comparison of pH-sensitive degradability of maleic acid amide derivatives." Bioorganic & medicinal chemistry letters 24, no. 10 (2014): 2364-2367.

Khatun, Zehedina, Md Nurunnabi, Md Nafiujjaman, Gerald R. Reeck, Haseeb A. Khan, Kwang Jae Cho, and Yong-kyu Lee. "A hyaluronic acid nanogel for photo-chemo theranostics of lung cancer with simultaneous light-responsive controlled release of doxorubicin." Nanoscale 7, no. 24(2015):10680-10689.

Kirby, A. J., and P. W. Lancaster, J. Chem. Soc., Perkin Trans. 2, 1972, 1206.

Klement R J, Kämmerer U (October 2011). "Is there a role for carbohydrate restriction in the treatment and prevention of cancer?". Nutrition & Metabolism. 8: 75. doi: 10.1186/1743-7075-8-75. PMC 3267662. PMID 22029671.

Langer, Robert, and Nicholas A. Peppas. "Advances in biomaterials, drug delivery, and bionanotechnology." AIChE Journal 49, no. 12 (2003): 2990-3006.

Langer, Robert. "Drug delivery and targeting." Nature-London (1998): 5-10.

Langer, Robert. "Drugs on target." Science 293, no. 5527 (2001): 58-59.

Langer, Robert. "New methods of drug delivery." Science 249, no. 4976 (1990): 1527-1533.

Lee M, Yoon J H (August 2015). "Metabolic interplay between glycolysis and mitochondrial oxidation: The reverse Warburg effect and its therapeutic implication". World Journal of Biological Chemistry (Review). 6 (3): 148-61. doi:10.4331/wjbc.v6.i3.148. PMC 4549759. PMID 26322173.

Lee, E. S., K. Na and Y. H. Bae, *Nano Lett.*, 2005, 5, 325.

Lee, E. S., Z. Gao and Y. H. Bae, *J. Controlled Release*, 2008, 132, 164.

Lee, Y. T., K. K. Chan, P. A. Harris and J. L. Cohen, Cancer, 1980, 45, 2231.

Lefrak, E. A., J. Pitha, S. Rosenheim and J. A. Gottlieb, Cancer, 1973, 32, 302.

Leriche, G., M. Nothisen, N. Baumlin, C. D. Muller, D. Bagnard, J. S. Remy, S. A. Jacques and A. Wagner, Bioconjugate Chem., 2015, 26, 1461.

Li, Hong-Jun, Jin-Zhi Du, Jing Liu, Xiao-Jiao Du, Song Shen, Yan-Hua Zhu, Xiaoyan Wang, Xiaodong Ye, Shuming Nie, and Jun Wang. "Smart superstructures with ultrahigh pH-sensitivity for targeting acidic tumor microenvironment: instantaneous size switching and improved tumor penetration." ACS nano 10, no. 7 (2016): 6753-6761.

Liberti M V, Locasale J W (March 2016). "The Warburg Effect: How Does it Benefit Cancer Cells?". Trends in Biochemical Sciences (Review). 41 (3): 211-218. doi: 10.1016/j.tibs.2015.12.001. PMC 4783224. PMID 26778478.

López-Lázaro M (April 2008). "The warburg effect: why and how do cancer cells activate glycolysis in the presence of oxygen?". Anti-Cancer Agents in Medicinal Chemistry. 8 (3): 305-12. doi:10.2174/187152008783961932. PMID 18393789.

Maier, K., and E. Wagner, J. Am. Chem. Soc., 2012, 134, 10169.

Mangin, F., E. Banaszak-Léonard, and C. Len. "One-step Barton decarboxylation by micellar catalysis-application to the synthesis of maleimide derivatives." Rsc Advances 5, no. 85 (2015):69616-69620.

Mathupala S P, Colen C B, Parajuli P, Sloan A E (February 2007). "Lactate and malignant tumors: a therapeutic target at the end stage of glycolysis". Journal of Bioenergetics and Biomembranes. 39 (1): 73-7. doi:10.1007/s10863-006-9062-x. PMC 3385854. PMID 17354062.

Meyer, M., A. Philipp, R. Oskuee, C. Schmidt and E. Wagner, J. Am. Chem. Soc., 2008, 130, 3272.

Michelakis E D, Webster L, Mackey J R (October 2008). "Dichloroacetate (DCA) as a potential metabolic-targeting therapy for cancer". British Journal of Cancer. 99 (7): 989-94. doi:10.1038/sj.bjc.6604554. PMC 2567082. PMID 18766181.

Minotti, G., P. Menna, E. Salvatorelli, G. Cairo and L. Gianni, Pharmacol. Rev., 2004, 56, 185.

Naganawa, A., Y. Ichikawa and M. Isobe, Tetrahedron, 1994, 50, 8969.

Oh, Kyung Taek, Dongin Kim, Hyeon Hee You, Yong Sik Ahn, and Eun Seong Lee. "pH-sensitive properties of surface charge-switched multifunctional polymeric micelle." International journal of pharmaceutics 376, no. 1-2 (2009): 134-140.

Pan J G, Mak T W (April 2007). "Metabolic targeting as an anticancer strategy: dawn of a new era?". Science's STKE. 2007 (381): pel4. doi:10.1126/stke.3812007pe14. PMID 17426345.

Park, Euddeum. "Development of a Novel Drug Carrier Using Cyclodextrins Containing Maleic Anhydride Moieties." PhD diss. (2015), Seoul National University.

Pavlides, Stephanos (Dec. 1, 2009). "The Reverse Warburg Effect".

Pedersen P L (June 2007). "Warburg, me and Hexokinase 2: Multiple discoveries of key molecular events underlying one of cancers' most common phenotypes, the "Warburg Effect", i.e., elevated glycolysis in the presence of oxygen". Journal of Bioenergetics and Biomembranes. 39 (3): 211-22. doi:10.1007/s10863-007-9094-x. PMID 17879147.

Pelicano H, Martin D S, Xu R H, Huang P (August 2006). "Glycolysis inhibition for anticancer treatment". Oncogene. 25 (34): 4633-46. doi:10.1038/sj.onc.1209597. PMID 16892078.

Reichert, M., J. P. Steinbach, P. Supra and M. Weller, Cancer, 2002, 95, 1113.

Rozema, D. B., D. L. Lewis, D. H. Wakefield, S. C. Wong, J. J. Klein, P. L. Roesch, S. L. Bertin, T. W. Reppen, Q. Chu, A. V. Blokhin, J. E. Hagstrom and J. A. Wolff, Proc. Natl. Acad. Sci. U.S.A, 2007, 104, 12982.

Rozema, D. B., K. Ekena, D. L. Lewis, A. G. Loomis and J. A. Wolff, Bioconjugate Chem., 2003, 14, 51.

Shen, Wei-Chiang, and Hugues J-P. Ryser. "cis-Aconityl spacer between daunomycin and macromolecular carriers: a model of pH-sensitive linkage releasing drug from a lysosomotropic conjugate." Biochemical and Biophysical Research Communications 102, no. 3 (1981): 1048-1054.

Shi, J., P. W. Kantoff, R. Wooster and O. C. Farokhzad, Nat. Rev. Cancer, 2017, 17, 20.

Skovsgaard, T., Biochem. Pharmacol., 1977, 26, 215.

Sluis, Robert van; Bhujwalla, Zaver M.; Raghunand, Natarajan; Ballesteros, Paloma; Alvarez, José; Cerdin, Sebastián; Galons, Jean-Philippe; Gillies, Robert J. (April 1999). <743::AID-MRM13>3.0.CO; 2-Z "In vivo imaging of extracellular pH using 1H MRSI". Magnetic Resonance in Medicine. 41 (4): 743-750. doi:10.1002/(SICI)1522-2594(199904)41:4<743::AID-MRM13>3.0.CO; 2-Z. Retrieved June 2015.

Sun, C. Y., Y. Liu, J. Z. Du, Z. T. Cao, C. F. Xu and J. Wang, Angew. Chem., Int. Ed., 2016, 55, 1010.

Tannock, I. F., and D. Rotin, *Cancer Res.*, 1989, 49, 4373.

Tewey, K. M., T. C. Rowe, L. Yang, B. D. Halligan and L. F. Liu, Science, 1984, 226, 466.

Tran Q, Lee H, Park J, Kim S H, Park J (July 2016). "Targeting Cancer Metabolism—Revisiting the Warburg Effects". Toxicological Research. 32 (3): 177-93. doi:10.5487/TR.2016.32.3.177. PMC 4946416. PMID 27437085.

Unwin R D, Craven R A, Harnden P, Hanrahan S, Totty N, Knowles M, Eardley I, Selby P J, Banks R E (August 2003). "Proteomic changes in renal cancer and co-ordinate demonstration of both the glycolytic and mitochondrial aspects of the Warburg effect". Proteomics. 3 (8): 1620-32. doi:10.1002/pmic.200300464. PMID 12923786.

Vander Heiden M G (September 2013). "Exploiting tumor metabolism: challenges for clinical translation". The Journal of Clinical Investigation. 123 (9): 3648-51. doi:10.1172/JCI72391. PMC 3754281. PMID 23999437.

Vander Heiden M G, Cantley L C, Thompson C B (May 2009). "Understanding the Warburg effect: the metabolic requirements of cell proliferation". Science. 324 (5930): 1029-33. Bibcode:2009Sci . . . 324.1029V. doi:10.1126/science.1160809. PMC 2849637. PMID 19460998.

Vukovic V., and I. F. Tannock, Br. J. Cancer, 1997, 75, 1167.

Warburg O (February 1956). "On the origin of cancer cells". Science. 123 (3191): 309-14. Bibcode:1956Sci . . . 123 . . . 309W. doi:10.1126/science.123.3191.309. PMID 13298683.

Weber, Cynthia E.; Kuo, Paul C. (September 2012). "The tumor microenvironment". Surgical Oncology. 21 (3): 172-177. doi:10.1016/j.suronc.2011.09.001. Retrieved June 2015.

Witz, Isaac P.; Levy-Nissenbaum, Orlev (Oct. 8, 2006). "The tumor microenvironment in the post-PAGET era". Cancer Letters. 242 (1): 1-10. doi:10.1016/j.canlet.2005.12.005. PMID 16413116. Retrieved June 2015.

Wojtkowiak, J. W., D. Verduzco, K. J. Schramm and R. J. Gillies, Mol. Pharmaceutics, 2011, 8, 2032.

Zeman, S. M., D. R. Phillips and D. M. Crothers, Proc. Natl. Acad. Sci. USA, 1998, 95, 11561.

Zhang, X., Y. Lin and R. J. Gillies, *J. Nucl. Med.*, 2010, 51, 1167.

U.S. Pat. Nos. 4,255,443; 4,383,994; 4,542,225; 4,569,789; 4,573,996; 4,618,492; 4,618,685; 4,666,441; 4,789,633; 4,886,761; 4,917,826; 4,925,931; 4,994,557; 5,066,490; 5,145,874; 5,187,299; 5,196,542; 5,223,440; 5,274,089; 5,274,119; 5,281,522; 5,283,122; 5,292,524; 5,306,809; 5,329,028; 5,334,712; 5,364,613; 5,373,095; 5,505,931; 5,527,528; 5,565,558; 5,599,831; 5,605,791; 5,616,606; 5,744,151; 5,856,551; 5,874,549; 5,889,155; 5,914,095; 5,929,211; 5,948,931; 6,004,583; 6,046,228; 6,054,595; 6,124,435; 6,248,916; 6,274,713; 6,274,742; 6,287,818; 6,297,337; 6,310,039; 6,326,353; 6,328,728; 6,414,013; 6,426,067; 6,582,928; 6,586,002; 6,602,498; 6,602,524; 6,630,351; 6,682,757; 6,696,082; 6,709,679; 6,919,091; 6,986,902; 7,001,616; 7,005,139; 7,019,113; 7,045,319; 7,067,272; 7,098,032; 7,108,863; 7,129,250; 7,138,382; 7,145,019; 7,153,977; 7,160,554; 7,166,575; 7,208,314; 7,226,738; 7,229,973; 7,297,494; 7,329,721; 7,432,330; 7,432,331; 7,442,764; 7,468,261; 7,470,511; 7,473,775; 7,524,875; 7,541,165; 7,595,198; 7,655,697; 7,659,314; 7,659,361; 7,670,627; 7,691,962; 7,734,422; 7,790,835; 7,812,051; 7,851,491; 7,863,245; 7,872,082; 7,883,720; 7,902,144; 7,951,846; 7,968,085; 7,985,406; 7,994,272; 8,003,117; 8,007,827; 8,008,355; 8,017,109; 8,034,981; 8,039,579; 8,058,385; 8,071,712; 8,097,277; 8,106,131; 8,137,695; 8,138,383; 8,158,590; 8,211,468; 8,211,857; 8,217,015; 8,227,555; 8,227,558; 8,258,324; 8,263,358; 8,263,664; 8,304,511; 8,309,614; 8,323,632; 8,324,333; 8,377,917; 8,399,403; 8,420,068; 8,454,946; 8,501,930; 8,512,757; 8,524,368; 8,541,548; 8,618,058; 8,629,151; 8,636,994; 8,653,286; 8,658,211; 8,663,599; 8,716,422; 8,758,778; 8,759,104; 8,765,111; 8,784,880; 8,795,648; 8,828,373; 8,835,556; 8,846,704; 8,895,759; 8,906,847; 8,945,927; 8,980,242; 8,986,609; 8,992,902; 9,005,670; 9,006,254; 9,034,829; 9,040,549; 9,056,126; 9,062,094; 9,066,867; 9,101,547; 9,101,670; 9,133,276; 9,138,462; 9,169,350; 9,180,195; 9,193,785; 9,216,209; 9,238,686; 9,249,179; 9,249,211; 9,255,929; 9,265,723; 9,272,048; 9,278,139; 9,289,397; 9,295,729; 9,303,077; 9,345,718; 9,345,775; 9,376,383; 9,403,901; 9,433,684; 9,457,066; 9,480,754; 9,493,609; 9,499,551; 9,504,756; 9,511,122; 9,526,796; 9,533,056; 9,561,285; 9,567,339; 9,572,813; 9,580,708; 9,636,374; 9,636,412; 9,682,131; 9,682,153; 9,687,553; 9,687,563; 9,732,340; 9,732,341; 9,737,484; 9,744,147; 9,745,359; 9,757,474; 9,790,494; 9,796,756; 9,828,465; 9,834,571; 9,849,087; 9,861,705; 9,872,864; 9,884,112; 9,910,040; 9,919,033; 9,925,269; 9,976,166; 9,999,599; 10,005,815; 10,010,623; 10,022,456; 10,029,001; 10,029,015; 10,035,856; 10,047,061; 10,058,587; 10,058,622; 10,064,964; 10,065,989; 10,072,075; 10,093,924; 10,098,930; 10,174,094; 10,232,042; 10,314,802; 10,370,436; 10,385,165; 10,399,962; 10,406,251; 10,428,111; 10,434,182; 10,435,471; 10,472,404; 10,519,226; 10,548,982; 10,631,781; 10,632,195; 10,660,969; 10,682,395; 10,704,046; 10,774,181; 20010034333; 20010043929; 20010051348; 20020009415; 20020019343; 20020146371; 20020146449; 20020192275; 20030026841; 20030059791; 20030099950; 20030109682; 20030148399; 20030157158; 20030185793; 20030198665; 20030199090; 20030202936; 20030203888; 20030220264; 20040028613; 20040037809; 20040054162; 20040058446; 20040077540; 20040081685; 20040102467; 20040109894;

20040115135; 20040132981; 20040137461; 20040157257; 20040162263; 20040167287; 20040175724; 20040204548; 20040220202; 20040223976; 20040224019; 20040234297; 20040234996; 20040258663; 20050014769; 20050026150; 20050031549; 20050054612; 20050058620; 20050064414; 20050070721; 20050085449; 20050085630; 20050123600; 20050130910; 20050137172; 20050176922; 20050186263; 20050208561; 20050250683; 20050276807; 20050287548; 20050288490; 20060002890; 20060009590; 20060024317; 20060034796; 20060057197; 20060069021; 20060073113; 20060115450; 20060122096; 20060177445; 20060204964; 20060211724; 20060216238; 20060240009; 20060269542; 20060270669; 20060270670; 20060286140; 20070027310; 20070049688; 20070077283; 20070104775; 20070141021; 20070185035; 20070232819; 20070264322; 20070275893; 20070275962; 20080032417; 20080113011; 20080146771; 20080152661; 20080161245; 20080241102; 20080269450; 20080279868; 20080281041; 20080281044; 20080281074; 20080287628; 20080287630; 20080311136; 20090012241; 20090023890; 20090048410; 20090074885; 20090118158; 20090142274; 20090192320; 20090226395; 20090258071; 20090274753; 20100009926; 20100021481; 20100022487; 20100022488; 20100022489; 20100022494; 20100022991; 20100023344; 20100029899; 20100041615; 20100061976; 20100068264; 20100092463; 20100092496; 20100113329; 20100159019; 20100239631; 20100247617; 20100249027; 20100260830; 20100261841; 20100291021; 20100329983; 20110020371; 20110020388; 20110020450; 20110027217; 20110046315; 20110053848; 20110071089; 20110076322; 20110082277; 20110112021; 20110166063; 20110171160; 20110171165; 20110190201; 20110223230; 20110237747; 20110246081; 20110262379; 20110269713; 20120003322; 20120004422; 20120022220; 20120035320; 20120064011; 20120070383; 20120090096; 20120123065; 20120156259; 20120157509; 20120208189; 20120226022; 20120230938; 20120253071; 20120271000; 20120302761; 20120316119; 20130022545; 20130030359; 20130035635; 20130052653; 20130053301; 20130065308; 20130084261; 20130096177; 20130142887; 20130150281; 20130165389; 20130281324; 20130309256; 20140030344; 20140045848; 20140051703; 20140080119; 20140113834; 20140127698; 20140128619; 20140142333; 20140187493; 20140193453; 20140206596; 20140227285; 20140242173; 20140303245; 20140303571; 20140309186; 20140323402; 20140328791; 20140328905; 20150005279; 20150010634; 20150037360; 20150057221; 20150079005; 20150087590; 20150094267; 20150098900; 20150148735; 20150182644; 20150183847; 20150196667; 20150202163; 20150202317; 20150210738; 20150231073; 20150238625; 20150247141; 20150273081; 20150297740; 20150299695; 20150315585; 20150315586; 20150315587; 20150315588; 20150320879; 20150328300; 20150359837; 20160022783; 20160022828; 20160030587; 20160058886; 20160089448; 20160102120; 20160136190; 20160136290; 20160199465; 20160206694; 20160206702; 20160213790; 20160228564; 20160256108; 20160263221; 20160297872; 20160347793; 20160354482; 20170008970; 20170016042; 20170035898; 20170056472; 20170096479; 20170100490; 20170112939; 20170114033; 20170152316; 20170165201; 20170174624; 20170183380; 20170196975; 20170211065; 20170233447; 20170258948; 20170296684; 20170312363; 20170326253; 20170333304; 20180030095; 20180030444; 20180044371; 20180085468; 20180098946; 20180104188; 20180104343; 20180140557; 20180154011; 20180193409; 20180214561; 20180215730; 20180221402; 20180221498; 20180235897; 20180256709; 20180258138; 20180271440; 20180311358; 20180327829; 20180333498; 20180346952; 20190008978; 20190031750; 20190060463; 20190062743; 20190070251; 20190100581; 20190127445; 20190151323; 20190153115; 20190184042; 20190192634; 20190209717; 20190284135; 20190290733; 20190322726; 20190343972; 20190350854; 20190365910; 20190375794; 20190388555; 20200002397; 20200046725; 20200069689; 20200078313; 20200093864; 20200190185; 20200222441; 20200254111; and 20200325274.

SUMMARY OF THE INVENTION

The present invention relates to a soluble prodrug delivery system which is charged, and therefore remains in an extracellular compartment, and which releases a drug, e.g., a cytotoxic agent, at low pH, for example in a tumor environment.

According to the present technology, the drug, a pre-prodrug, is manufactured in the cyclized disubstituted maleimide (DMI) structure form. The pre-prodrug has at least three portions: a drug, e.g., an antineoplastic therapy, which has a primary amino group or amine functionality, a maleimide which is formed through cyclization onto the amino group, a linker, and a targeting or membrane impermeable functionality, which is, e.g., a charged ligand, that typically blocks cellular entry in the prodrug state (wherein the disubstituted maleimide is converted to disubstituted maleamic acid (DMA) by ring opening).

The cyclized disubstituted maleimide form, i.e. the pre-prodrug, is stable and can have practical shelf life. Before administering to the patient, the disubstituted maleimide is converted to the corresponding disubstituted maleamic acid by ring opening, which occurs, for example, in pH 10 aqueous solution after one hour or three hours. The resulting disubstituted maleamic acid compound is the prodrug, which may be administered to a patient, for example i.v., intratumorally, intraperitoneally, etc. The DMA prodrug is generally stable at a pH at or above 7.4. Below pH 6.8, the amide bond in the maleamic acid moiety is cleaved to release the free drug for cellular uptake. The drug release byproduct from the linker, i.e., ring closed disubstituted maleic anhydride is generally not toxic to cells.

For example, the conjugate Dox-DMA-GSH provides 60-70% release of drug (doxorubicin) in 3 hrs at 37° C. at pH 6.5, but only 10-20% release of drug in 3 hr. at 37° C. at pH 7.4 (FIG. 6). The DMA linkage is ultra acid-labile.

The present technology provides a selective release of drug in acidic tissues, such as tumor microenvironments, sites of inflammation, ischemic tissue (e.g., heart attack, stroke), etc. Since the metabolic activity of the cancer cells is increased, cancerous solid tumors almost always have acidic extracellular microenvironments (usually pH 6.5-7.0). Furthermore, in a cancer patient, the tumor extracellular pH may be further acidified by 0.1-0.2 pH unit through prior administration of glucose to the patient, and therefore the targeted drug release effect may be enhanced.

In the case of doxorubicin, the drug passes through cell membranes and acts intracellularly. The DMA derivatization involving polar moieties (e.g., carboxyl or other ionized species at pH 6.0-7.4 in aqueous media) provides a way to reduce cellular uptake of the DMA prodrug and keep the antineoplastic agent in the extracellular compartment. Other charged ligands may be employed, such as L-amino acids or D-amino acids, dipeptides, polypeptides, organic acids, heterocyclic compounds, etc. However, in the tumor microenvironment, the pH may be 6.8 or below, leading to selective release of the antineoplastic agent. This extracellular pH-based targeting specificity may be on the order of 400%, leading to a significant increase in therapeutic index, and in the case of doxorubicin, a significant reduction in cumulative dose-limiting cardiotoxicity.

The technology may have particular application in the treatment of sarcoma. Soft tissue sarcomas represent a group of heterogeneous mesenchymal tumors that occur rarely in adults. While a variety of histological subtypes exist, some of the most common are leiomyosarcoma and liposarcoma. For eligible patients, standard first-line treatment of metastatic disease has typically comprised anthracycline-containing regimens. However, anthracyclines display significant dose dependent and cumulative cardiotoxicity. This toxicity limits therapy in many patients, and thus by increasing therapeutic index, significant benefits can accrue. Therefore, targeting improves the anthracycline drug.

In other cases, the drug need not be an antineoplastic drug, and a targeting agent as part of the DMA derivatization may selectively bind to cells and induce endocytosis, or bind to biomaterials, filters, or the like. In that case, the endosomes become progressively more acidic along the endosomal trafficking pathway (pH 7.0 to pH 6.0), and after fusing with lysosomes, the pH inside of the vesicles may be as low as ~5.0, which will release the drug almost instantly. Some drugs will then be free to diffuse out of the endosome, and therefore be active in the cytosol, while others may act within the endosome, such as a pore-forming peptide which release the endosome contents (or a portion thereof) into the cell.

It is noted that the technology need not be used exclusively in vivo, and therefore may be used in cell culture, and biotechnological apparatus where pH-responsive drug delivery is desired. The targeting agents may be peptides, antibodies or fragments thereof, receptor binding peptides or fragments, protease inhibitors, etc.

The prodrug may also target non-mammalian cells, such as bacteria and fungi, or parasites, in which case the drug may be an antibiotic or antifungal agent.

It is therefore an object to provide a method of treating a neoplastic disease, comprising: providing a pre-prodrug comprising an antineoplastic agent having an amine functionality, which forms a portion of a disubstituted maleimide linker having a membrane impermeable functionality, the linker lacking a disulfide bond linking the disubstituted maleimide and the membrane impermeable functionality; convert the disubstituted maleimide of the pre-prodrug to a prodrug comprising a disubstituted maleamic acid, through ring opening in vitro; the disubstituted maleamic acid being pH labile and being at least 66% bound to the antineoplastic agent at pH 7.4 and being less than 33% bound to the antineoplastic agent at pH 6.8 after, e.g., one to three hours; and administering the prodrug to a patient having the neoplastic disease characterized by a tumor, in a sufficient amount to treat the tumor, wherein the tumor has a tumor microenvironment having an extracellular pH less than 7.0, to thereby increase release of the antineoplastic agent to the tumor and reduce release of the antineoplastic agent to other tissues of the patient having an a pH greater than 7.0. The pre-prodrug may be treated with a pH 10 aqueous buffer for about 1 hour to convert the pre-prodrug to the prodrug.

It is another object to provide a pre-prodrug comprising: an antineoplastic agent having an amine functionality; and a linker having a disubstituted maleimide comprising the amine functionality, the linker being membrane impermeable functionality; the linker lacking a disulfide bond linking the disubstituted maleimide and the membrane impermeable functionality.

The antineoplastic agent may comprise an anthracycline; doxorubicin; daunorubicin; epirubicin; idarubicin; sabarubicin; amrubicin; berubicin; pirarubicin; zorubicin; camsirubicin (GPX-150); pixantrone; eribulin; and/or a topoisomerase inhibitor.

The linker and/or membrane impermeable functionality may comprise a D- or L-amino acid. a dipeptide, tripeptide, or polypeptide. The membrane impermeable functionality may be at least one of a carboxylic acid, a sulfonic acid, a sulfuric acid, a phosphonic acid, a phosphoric acid, a boronic acid, a polyprotic acid, a zwitterion, a nucleic acid, an RNA, a DNA, an antibody, an antibody fragment, a cell-surface receptor binding agent, an affibody, a lectin, an antigen, a dye, a fluorescent dye, a microcin, a bacteriocin, and/or a pore-forming peptide. The linker may be bound to a nanoparticle or a polymer.

The membrane impermeable functionality of the prodrug may comprise a charged ligand which has a charge in aqueous solution at a pH 6.8, or having a charge in aqueous solution over a range of pH 6.5 to pH 7.0.

It is also an object to provide a pre-prodrug comprising: an antineoplastic agent having an amine; and a linker having a disubstituted maleimide moiety comprising the amine, linked through an alkyl chain to a disulfide bond to cysteine.

It is a further object to provide a pre-prodrug comprising a physiologically active drug having an amine functionality, and a linker having a disubstituted maleimide comprising the amine functionality having a targeting moiety, the linker lacking a disulfide bond linking the disubstituted maleimide and the targeting moiety, the pre-prodrug being convertible upon ring opening to a disubstituted maleamic acid prodrug, the disubstituted maleamic acid prodrug being acid labile at a pH less than 6.8 to release at least 50% of the drug in three hours at 37° C. in aqueous medium, and being more stable at a pH greater than 7.4 to release no more than 20% of the drug in three hours at 37° C. in aqueous medium.

The physiologically active drug may be an antineoplastic agent, e.g., a topoisomerase inhibitor, e.g., an anthracycline, e.g., doxorubicin.

The targeting moiety may comprise an amino acid, e.g., a basic amino acid and/or an acidic amino acid.

The linker lacking the disulfide bond linking the disubstituted maleimide and the targeting moiety may comprise an alkyl chain having at least two carbons.

The disubstituted maleamic acid prodrug may be adapted to release drug in a tumor microenvironment and to maintain drug in unreleased form in a cardiac environment.

It is another object to provide a prodrug comprising a physiologically active drug having an amine functionality, and a linker having a disubstituted maleamic acid comprising the amine functionality having a targeting moiety, the linker lacking a disulfide bond linking the disubstituted maleamic acid and the targeting moiety, the prodrug being acid labile at a pH less than 6.8 to release at least 50% of the drug in three hours at 37° C. in aqueous medium, and being stable at a pH greater than 7.4 to release no more than 20% of the drug in three hour at 37° C. in aqueous medium.

It is another object to provide a pharmaceutically acceptable formulation of a pre-prodrug comprising a membrane permeable therapeutic or diagnostic compound having an amine functionality, condensed to form a cyclized disubstituted maleimide linked to a targeting or detargeting agent.

The membrane permeable therapeutic or diagnostic compound having the amine functionality, the disubstituted maleimide, and the targeting or detargeting agent, are selected such that upon decyclization in pH 10 aqueous solution for 1 hour, the product comprises at least 90% of the DMA prodrug comprising the membrane permeable therapeutic or diagnostic compound having the amine functionality condensed to form a disubstituted maleamic acid linked to the targeting or detargeting agent, with 5% or less of the starting DMI pre-prodrug, and no more than 5% of other unknown by-products/impurities. The product may comprise at least 95% of the pre-prodrug and a prodrug together.

The pharmaceutically acceptable formulation may be adapted to decyclize in pH 10 aqueous solution to form a substantially pure solution consisting essentially of the DMA prodrug (90%).

The membrane permeable therapeutic or diagnostic compound may be selected from the group consisting of doxorubicin, daunorubicin; epirubicin; idarubicin; sabarubicin; amrubicin; berubicin; pirarubicin; zorubicin; camsirubicin; pixantrone; and eribulin, and is preferably doxorubicin.

The targeting or detargeting agent may comprise a membrane impermeable charged ligand.

The disubstituted maleimide of the pre-prodrug is preferably hydrolysable to a disubstituted maleamic acid of a prodrug, which after two hour in aqueous medium at least 40% amine drug is released at pH 6.5 and at most 20% amine drug is released at pH above 7.4.

The disubstituted maleimide of the pro-prodrug may be hydrolysable to a disubstituted maleamic acid of a prodrug, which is after three hours in aqueous medium at least 66% hydrolyzed below pH 6.8 to the drug comprising the membrane permeable therapeutic or diagnostic compound having an amine functionality drug and at most 33% hydrolyzed above pH 7.4 to the drug.

The targeting or detargeting agent may be selected from the group consisting of a D-amino acid; an L-amino acid; a dipeptide; a tripeptide; a polypeptide; a carboxylic acid; a sulfonic acid; a sulfuric acid; a phosphonic acid; a phosphoric acid; a boronic acid; a polyprotic acid; a zwitterion; a nucleic acid; an RNA; a DNA; an antibody; an antibody fragment; a cell-surface receptor binding agent; an affibody; a lectin; an antigen; a dye; a fluorescent dye; a microcin; a bacteriocin; and a pore-forming peptide. The targeting or detargeting agent may comprise a charged ligand has a charge in aqueous solution at a pH 6.8.

The converting may produce the substantially pure pH labile prodrug comprising in aggregate at least 90% of the pre-prodrug and the pH labile prodrug, for administration to the subject. The substantially pure pH labile prodrug may comprise, for example, about 90% of the pH labile prodrug, about 5% of the pre-prodrug (including therapeutically active isomers), and less than 5% of other forms of the drug, including free drug. The percentages are referred to on a molar (yield) basis.

It is a still further object to provide a pre-prodrug pharmaceutically acceptable formulation comprising: an anthracycline drug having a primary amine; and a linker having a disubstituted maleimide moiety cyclized with the primary amine, linked to a ligand having a moiety charged in aqueous solution at pH 6.8, the ligand being non-reactive with the anthracycline drug and the disubstituted maleimide moiety such that after an hour in aqueous solution at pH 10, at least 95% of the anthracycline drug is one of free anthracycline drug (small trace amount), anthracycline drug cyclized with the disubstituted maleimide moiety linked to the ligand (5% or less), and anthracycline drug forming an amide with a disubstituted maleamic acid linked to the ligand (90%).

The pre-prodrug is preferably convertible upon ring opening to the anthracycline drug conjugated to the disubstituted maleamic acid, being acid labile in an aqueous medium at a pH less than 6.5 to release at least 50% of the anthracycline drug in three hours at 37° C. in aqueous medium, and being stable in an aqueous medium at a pH greater than 7.4 to release no more than 20% of the anthracycline drug in three hour at 37° C. The anthracycline drug is preferably doxorubicin.

The ligand having a moiety charged in aqueous solution at pH 6.8 may comprise an amino acid or dipeptide. The ligand having a moiety charged in aqueous solution at pH 6.8 may comprise cysteine linked to the disubstituted maleimide moiety through a disulfide bond. The ligand having a moiety charged in aqueous solution at pH 6.8 may be linked to the disubstituted maleimide moiety through a non-disulfide bond.

It is another object to provide a method of treating a disease, comprising: providing a pre-prodrug, comprising a drug having a free amine reacted to form a cyclized disubstituted maleimide compound, linked through a linker to a targeting or detargeting functionality; converting the agent to a substantially pure pH labile prodrug, comprising the drug having a free amine forming an amide with the disubstituted maleamic acid compound, linked through the linker to the targeting or detargeting functionality, through in vitro ring opening; and administering the substantially pure pH labile prodrug to a subject.

The converting may comprise treating the pre-prodrug with a pH 10 aqueous buffer for about 1-2 hours to convert the pre-prodrug to the substantially pure pH labile prodrug. The drug having the free amine may comprises an anthracycline.

The substantially pure pH labile prodrug agent may be, after one hour in aqueous medium at 37° C., at least 40% of payload is released at pH 6.5 to form the free amine drug and at most 20% payload is released at pH 7.4 to form the free amine drug.

The targeting or detargeting agent may be selected from the group consisting of a D-amino acid; an L-amino acid; a dipeptide; a tripeptide; a polypeptide; a carboxylic acid; a sulfonic acid; a sulfuric acid; a phosphonic acid; a phosphoric acid; a boronic acid; a polyprotic acid; a zwitterion; a nucleic acid; an RNA; a DNA; an antibody; an antibody fragment; a cell-surface receptor binding agent; an affibody; a lectin; an antigen; a dye; a fluorescent dye; a microcin; a bacteriocin; and a pore-forming peptide.

Other objects will become apparent from a review of the detailed specifications and drawings.

BRIEF DESCRIPTION OF THE DRAWINGS

FIGS. 3A-3C show synthesis of DMI pre-prodrugs of Dox.

FIG. 4 shows preparation of DMA prodrugs and drug release reactions.

FIGS. 5A-5I show Dox release from DMA prodrug 8 (Dox-DMA-GSH) in pH 6.0-7.4 aq. buffer at RT.

FIGS. 6A-6D show Dox release from DMA 8 (Dox-DMA-GSH) at 37° C. with or without serum.

FIGS. 7A-7I show Prodrug8 (Dox-DMA-GSH) can reverse the unfavorable pH-profile of Dox.

FIGS. 11A-11D show $IC_{50}$ plots of Dox and Dox-DMA-GSH 8 with ES2 cells at pH 7.4 vs. pH 6.7. ES2 cells in 96-well plates were treated with Dox or DMA prodrug 8 at the given concentrations and pH values for 2.5 hrs, then grown under normal conditions for 2-4 days before counted in MTS assays. Cell viability percentages shown are normalized to the buffer negative control at a particular pH. The pH values of treatment solutions were measured before and after each experiment to give the pH ranges reported. $IC_{50}$ plots are fitted with 0% and 100% inhibition at very low and very high concentrations (experimental data shown support such fitting, i.e., $IC_{50}$ is approximately the same as $EC_{50}$). Error bar is ±1 standard deviation (SD) (n=6). The $IC_{50}$ values extracted from the fittings are plotted in FIG. 7D.

FIG. 17 shows an overall Synthesis of disulfide-containing DMI-prodrug (convert to DMA just prior to use).

FIGS. 18, 19, 20, 21, and 22 show bar graphs of free drug vs. DMA prodrug at different pH, for MDA-MD231, PC-3 dells, U87GM, SKOV3, and OVCAR3 cells, respectively.

FIGS. 24A-24F show pH-dependent drug release of Dox-DMA 2a/b at rt in aq. phosphate buffer. The dynamic conversion processes from Dox-DMA 2a/b to Dox or Dox-DMI 1 were monitored at pH 7.4 (24A), 7.0 (24B), 6.8 (24C), 6.5 (24D), 6.3 (24E), or 6.0 (24F). Shown in black is the consumption of the Dox-DMA 2a/b prodrug. Shown in red is the amount of Dox released. Shown in blue is the formation of Dox-DMI 1. Shown in green is background decomposition related to Dox-containing compounds. The legend for various compounds is shown in pH 7.4 per FIG. 24A.

FIGS. 25A-25E show pH-dependent drug release from Dox-DMA-Glu 4a/b at rt in aq. phosphate buffer. Prodrug consumption (black), drug release (red), DMI formation (blue), and other decompositions (green) were followed by HPLC at pH 7.4 (25A), 7.1 (25B), 6.8 (25C), 6.5 (25D), or 6.2 (25E).

FIGS. 26A-26E show pH-dependent drug release from Dox-DMA-Cys 6a/b at rt in aq. phosphate buffer. Prodrug consumption (black), drug release (red), DMI formation (blue), and other decompositions (green) were tracked by HPLC at pH 7.4 (26A), 7.1 (26B), 6.8 (26C), 6.5 (26D), and 6.2 (26E).

FIGS. 27A-27F show pH-selective drug release from DMA prodrugs at 37° C. Prodrug consumption (black), drug release (red), DMI formation (blue), and other decompositions (green) were tracked by HPLC at pH 7.4 (27A, 27C, 27E) and 6.5 (27B, 27D, 27F). Data regarding Dox-DMA 2a/b are shown in FIGS. 27A-27B, Dox-DMA-Glu 4a/b in FIGS. 27C-27D, and Dox-DMA-Cys 6a/b in FIGS. 27E-27F.

FIGS. 28A-28F show drug release comparison of various DMA prodrugs at 37° C. The behavior of the three prodrugs are plotted side-by-side. Dox release at pH 7.4 (28A) and 6.5 (28B) are shown in red. DMA consumption at pH 7.4 (28C) and 6.5 (28D) are shown in black. DMI formation at pH 7.4 (28E) and 6.5 (28F) are shown in blue. Round dots with dash-dot lines are the data relating to Dox-DMA 2a/b. Rhombuses with dotted lines are the data of Dox-DMA-Glu 4a/b. Squares with solid lines are the data regarding Dox-DMA-Cys 6a/b.

FIGS. 30A-30E show effects of pH, dose and treatment time on the pH-sensitive cytotoxicity of Dox-DMA-Glu 4a/b. (30A) The effect of pH on the cytotoxicity of Dox-DMA-Glu 4a/b and free Dox. ES2 ovarian cancer cells were treated for 3 h with 3 $\mu$M of Dox-DMA-Glu 4a/b (blue bars), 1 $\mu$M of free Dox (orange bars), or vehicle (phosphate buffer with small amount of DMSO, white bars) at various pH values between pH 6.1 and 7.4. (30B) Cytotoxicity of Dox-DMA-Glu 4a/b and free Dox on noncancerous kidney epithelial HK2 cells at pH 7.4. HK2 cells were treated with Dox-DMA-Glu 4a/b (blue) or free Dox (orange) at concentrations ranging from 3 nM to 30 $\mu$M. (30C) The effect of dose on the pH-dependent cytotoxicity of prodrug 4a/b. ES2 cells were treated for 2.5 h with 1, 2, 4 or 8 $\mu$M of Dox-DMA-Glu 4a/b at pH 6.5-6.7 (blue) or pH 7.2-7.5 (orange). (30D) The anhydride byproduct 10 of drug release is not cytotoxic. ES2 cells were treated with 3, 30 or 300 $\mu$M of 10 at pH 6.5-6.6 (blue) or 7.4-7.5 (orange) for 3 h. (30E) The effect of treatment duration on the pH-dependent cytotoxicity of Dox-DMA-Glu 4a/b. ES2 cells were treated with Dox-DMA-Glu 4a/b (2 $\mu$M), free Dox (0.5 $\mu$M), or vehicle for 1, 2, 4 or 8 h at pH 6.5-6.6 (blue) or pH 7.5-7.7 (orange). All pH values reported were based on measurements done before and after each treatment. All experiments were carried out in 96-well plates. After treatment, cells were grown for a few days before the number of live cells per well was counted using the MTS assay. Data shown represent the average ±SD (n=6 except for FIG. 30A where n=4 and FIG. 30D where n=5). Statistical significances of the difference between the chosen data sets were evaluated using unpaired, two-tailed Student's test (*: P<0.05, : P<0.01, *: P<0.001).

FIGS. 31A-31E show effects of pH, dose and treatment time on the pH-sensitive cytotoxicity of Dox-DMA-Cys 6a/b. (31A) The effect of pH on the cytotoxicity of Dox-DMA-Cys 6a/b and free Dox. ES2 ovarian cancer cells were treated for 2 h with 2 $\mu$M of Dox-DMA-Cys 6a/b (blue bars), 1 $\mu$M of free Dox (orange bars), or vehicle (phosphate buffer with small amount of DMSO, white bars) at various pH values between pH 6.1 and 7.5. (31B) Cytotoxicity of Dox-DMA-Cys 6a/b and free Dox on noncancerous kidney epithelial HK2 cells at pH 7.4. HK2 cells were treated with Dox-DMA-Cys 6a/b (blue) or free Dox (orange) at concentrations ranging from 3 nM to 30 $\mu$M. (31C) The effect of dose on the pH-dependent cytotoxicity of prodrug 6a/b. ES2 cells were treated for 3 h with 1, 2, 4 or 8 $\mu$M of Dox-DMA-Cys 6a/b at pH 6.4-6.5 (blue) or pH 7.3-7.4 (orange). (31D) The anhydride byproduct 12 of drug release is not cytotoxic. ES2 cells were treated with 2, 20 or 200 $\mu$M of 12 at pH 6.7 (blue) or 7.4-7.5 (orange) for 2 h. (31E) The effect of treatment duration on the pH-dependent cytotoxicity of Dox-DMA-Cys 6a/b. ES2 cells were treated with Dox-DMA-Cys 6a/b (2 $\mu$M), free Dox (0.5 $\mu$M), or vehicle for 1, 2, 4 or 8 h at pH 6.7 (blue) or pH 7.4-7.6 (orange). All pH values reported were based on measurements done before and after each treatment. All experiments were carried out in 96-well plates. After treatment, cells were grown for a few days before the number of live cells per well was counted using the MTS assay. Error bars reflect ±SD (n=6 except for FIG. 31A where n=4). Statistical significances of the difference between the chosen data sets were evaluated using unpaired, two-tailed Student's test (*: P<0.05, : P<0.01, *: P<0.001).

FIGS. 32A-32D show side-by-side comparison of prodrugs 2a/b, 4a/b and 6a/b. In FIGS. 32A-32C, ES2 ovarian cancer cells were treated for 2 h with 2 μM of Dox-DMA 2a/b, Dox-DMA-Glu 4a/b and Dox-DMA-Cys 6a/b at pH 6.4 vs 7.2 (32A), pH 6.6 vs 7.4 (32B), or pH 6.8 vs 7.3 (32C). In FIG. 32D, ES2 cells were treated with 4 μM of prodrugs at pH 6.8 vs 7.5. The positive control was 1 μM of Dox and the negative control was the vehicle (buffer with a trace amount of DMSO). Cell proliferation was determined by MTS assay after 3 days of incubation. The pH ranges reported come from measurements made before and after the experiment. Error bars reflect ±SD. Statistical significances of the difference between the chosen data sets were evaluated using unpaired, two-tailed Student's test (*: P<0.05, : P<0.01, *: P<0.001).

FIG. 33 shows confocal microscopy images of free Dox at pH 6.7 and 7.7. ES2 cells were treated with 4 μM of Dox at pH 6.7 or 7.7 for 1 hour; the treatment solution was removed; then the nuclei of ES2 cells were labeled with Hoechst 33342 (blue) for 10 min; images were taken immediately afterwards with a Leica TCS SP5 Confocal Laser Scanning Microscope with a 63× oil lens. The scale bars represent 25 m. Red: fluorescence of Dox (or Dox-containing compounds), blue: nuclei.

FIG. 37 shows structures of Dox-DMA linker only prodrug and its precursor DMI preprodrug (stable shelf life, the product).

FIG. 38 shows Dox-DMA linker-amino acid prodrug and its precursor DMI.

FIG. 39 shows Dox-DMA linker-dipeptide prodrug and its precursor DMI.

FIG. 45 shows activation of pre-prodrug Dox-DMI-GSH 7 to prodrug Dox-DMA-GSH 8a/8b.

FIG. 46 exchanging cysteine in the anhydride-disulfide.

FIG. 47 shows an equilibrium between the anhydride and diacid form.

Figure 1:
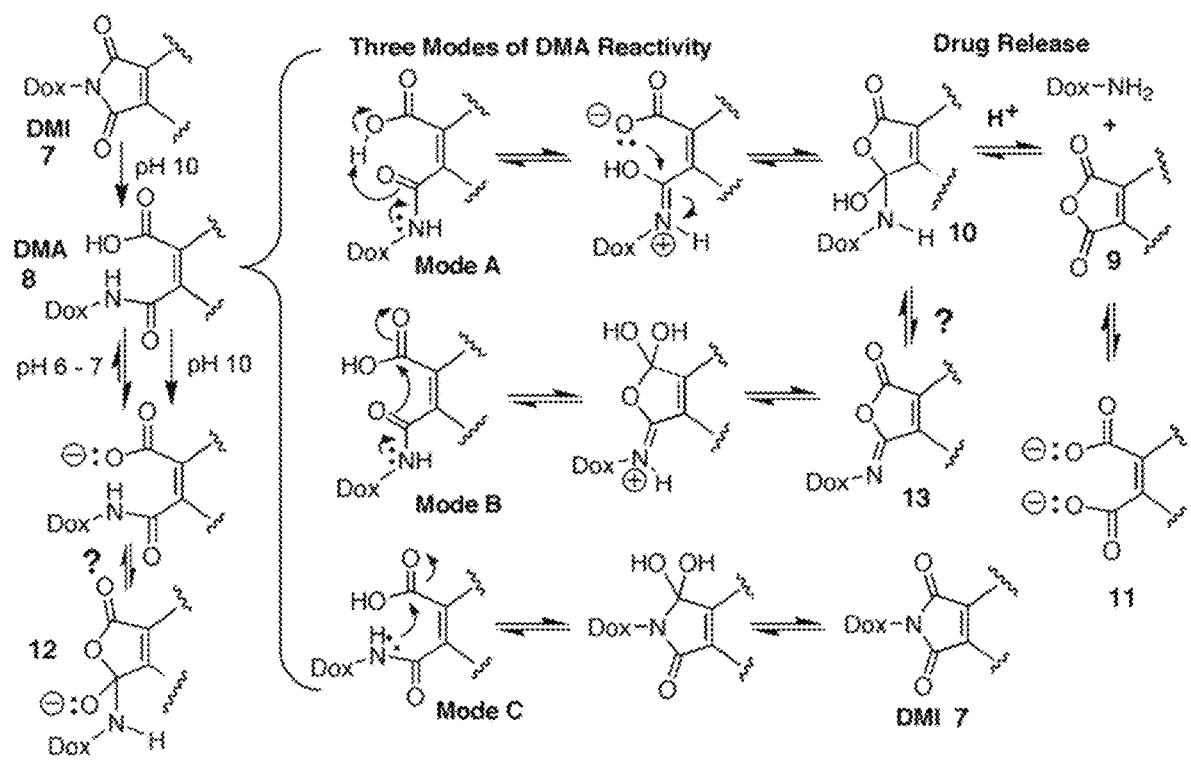
FIG. 1 shows potential mechanisms of pH-dependent drug release.
Figure 2:
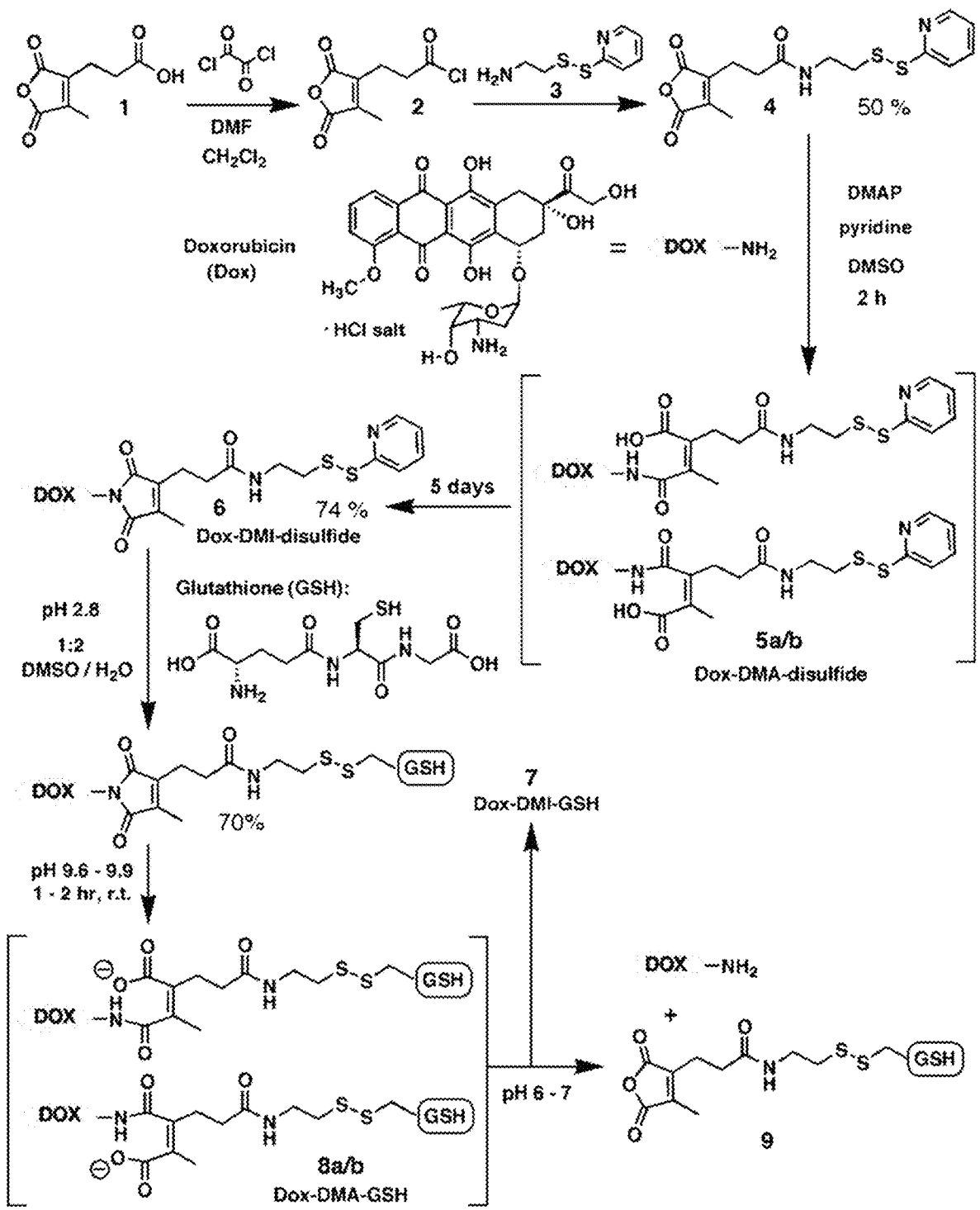
FIG. 2 shows synthesis of the DMA prodrug via the DMI precursor.

DETAILED DESCRIPTION OF THE PREFERRED EMBODIMENTS
METHODS/EXPERIMENTAL DETAILS

Chemicals for Synthesis (General Information). Dimethylformamide (DMF), triethylamine (TEA), trifluoroacetic acid (TFA), and 2-aminoethanethiol hydrochloride (98% pure) were purchased from Acros Organics; triethyl-2-phosphonopropionate (98% pure), sodium hydride (57-63% dispersion in mineral oil, moist powder), pyridyl disulfide (98% pure), dimethylsulfoxide (DMSO), anhydrous acetonitrile, 1,8-diazabicyclo[5,4,0]undec-7-ene (DBU, 99% pure), 4-dimethylaminopyridine (DMAP, 99% pure), and oxalyl chloride (98% pure) from Alfa Aesar; dimethyl-2-oxo-glutarate (95% pure) from TCI America; tetrahydrofuran (THF), ethyl ether, anhydrous magnesium sulfate, ethyl acetate, sodium hydroxide, methanol, pyridine from Fisher Scientific; chloroform-d, and dimethyl sulfoxide-d6 from Cambridge Isotope Laboratories (CIL); doxorubicin (Dox) hydrochloride salt from LC Laboratories; hexanes from BDH; ethanol from Pharmaco-APPER; dichloromethane from Macron Fine Chemicals/Avantor Performance Materials; glutathione (free acid form, reduced) from EMD Millipore—Calbiochem; acetic acid, sodium phosphate (dibasic and monobasic) from JT Baker; SiliaFlash P60 silica gel, 40-63 μm, 60 Å from SiliCycle; and acetonitrile (HPLC solvent) from Spectrum or JT Baker. Purity of each reagent and solvent is greater than 99% (unless noted otherwise) and used without further purification. Water was obtained from Millipore Milli-DI system connected to in-house deionized (DI) water source.

General Procedures for HPLC. High pressure/performance liquid chromatography (HPLC) is used to purify various compounds, monitor reaction progress, isolate desired products, and ascertain sample integrity over time. A Shimadzu HPLC system F (two LC-6AD pumps with a SPD-M20A Prominence 200-800 nm full-spectrum diode array detector) or a Shimadzu HPLC system P (one LC-20AT quaternary pump with a SPD-20A two-wavelengths UV-vis detector) connected to a semi-prep Agilent Zorbax 9.4 mm (width)×250 mm (length) SB-C18 reverse phase semi-prep column (column Z) or a Hamilton 4.1 mm (w)×150 mm (1) PRP-1 polystyrene-divinylbenzene (PS-DVB) polymer reverse phase analytical column (column H) is run with the following general method: flow rate, 3 mL/min for semiprep column Z, or 1 mL/min for analytical column H; solvent systems A/B will be defined in specific HPLC conditions below; 60-min method: at 99:1 A/B for 10 min, followed by 99:1 A/B to 1:99 A/B in 30 min (the gradient), then at 1:99 A/B for 5 min, 1:99 A/B to 99:1 A/B in 2 min, and then at 99:1 A/B for 13 min. Specific HPLC conditions that differ in column choice (Z or H), solvents A/B, mobile phase pH (pH 2-3 or pH 8-8.5) and specific HPLC set-up (system F or P) are described below:

HPLC condition A: C18 column Z; pH 8-8.5; HPLC system F; phase A is water (with 0.08% TEA and 0.04% TFA); phase B is acetonitrile (with 0.08% TEA and 0.04% TFA).

HPLC condition B: C18 column Z; pH 2-3; HPLC system P; phase A is water/acetonitrile 95:5 (with 0.01% TFA); phase B is acetonitrile (with 0.01% TFA).

HPLC condition C: C18 column Z; pH 2-3; HPLC system F; phase A is water/acetonitrile 95:5 (with 0.01% TFA); phase B is acetonitrile (with 0.01% TFA).

HPLC condition D: C18 column Z; pH 8-8.5; HPLC system P; phase A is water (with 0.08% TEA and 0.04% TFA); phase B is acetonitrile (with 0.08% TEA and 0.04% TFA).

HPLC condition E: PS-DVB column H; pH 8-8.5; HPLC system P; phase A is water/acetonitrile 95:5 (with 0.08% TEA and 0.04% Acetic Acid); phase B is acetonitrile (with 0.08% TEA and 0.04% Acetic Acid).

For purification runs, the collected eluents were concentrated under reduced pressure to remove acetonitrile after which the aqueous solution/suspension was lyophilized to dryness (solid or oily residue). The residue may contain small amounts of triethylammonium trifluoroacetate ionic liquid, depending on the specific solvent systems used. When doxorubicin-containing material was quantified using absorbance at 480 nm, the extinction coefficient of 11,500 $M^{-1} \cdot cm^{-1}$ was used. [Zeman 1998] Since all Dox conjugations described in this paper took place on the amino group of the pyranose sugar daunosamine, which is not conjugated to the chromophore, it was assumed that all Dox conjugates would also have the same extinction coefficient at 480 nm (11,500 $M^{-1} \cdot cm^{-1}$).

Mass Spectrometry. All mass measurements were obtained by the Mass Spectrometry Laboratory at the University of Illinois, Urbana-Champaign, HPLC Assay of pH-dependent DMA Cleavage (i.e., Doxorubicin Release from DMA 8). Release of doxorubicin from Dox-DMA-GSH 8a/b was studied at different pH, temperature (rt~25° C. or 37° C.) and environment (sodium phosphate buffer or 45% FBS in cell media) through monitoring by HPLC at pH~8. DMI 7 was converted to DMA 8a/b after 1-2 hr rt incubation at pH 9.6-9.9 in 25 mM aq. sodium phosphate buffer (see later synthesis sections for details). The pH of the DMA 8a/b solution was adjusted to 7.4, 7.0, 6.8, 6.5, 6.3, or 6.0. Then the solution was allowed to sit at rt (~25° C.) or placed in an incubator at 37° C. in the dark for up to a few days (the pH did not change during this time). Release of doxorubicin was monitored using HPLC (condition D or E, 480 nm, ~5 nmol per HPLC run).

Cell Cultures. Materials. The following media, buffers, and cell culture reagents were purchased from Life Technologies—Invitrogen: DMEM/F-12 Medium without phenol red (Gibco 21041), DMEM/F-12 Medium (Gibco 11320), Ham's F-12K Medium (Kaighn's modification, with L-glutamine, Gibco 21127), Fetal Bovine Serum (FBS) (Gibco 26140), Antibiotic-Antimycotic (Anti-Anti) 100× (Gibco 15240), Trypan blue stain 0.4% (for cell counting), and Trypsin-EDTA (for cell dissociation). Good's buffers ingredients 2-[4-(2-hydroxyethyl)-piperazin-1-yl]-ethanesulfonic acid (HEPES, pKa=7.5 at 25° C.) and 2-(N-morpholino)-ethane-sulfonic acid (MES, pKa=6.2 at 25° C.) were purchased from EMD Chemicals-Cal-Biochem. RPMI-1640 Medium (ATCC 30-2001) was purchased from American Type Culture Collection (ATCC). McCoy's 5A Medium (Lonza 12-688) was purchased from Lonza. Dulbecco's Modified Eagle's Medium (DMEM) was purchased from Sigma-Aldrich. MTS assay kit (CellTiter 96® AQueous One Solution Cell Proliferation Assay solution) was purchased from Promega Corp. AlamarBlue fluorescence dye cell viability assay reagent (10×) was purchased from Bio-Rad (BUF012B).

Sterile cell culture flasks (25 $cm^2$ and 75 $cm^2$) were obtained from Corning Inc. MTS experiments were carried out in 96-well plates purchased from Greiner Bio-one.

Cell lines. NIH:OVCAR3 human ovarian cancer cells (adenocarcinoma, ovary, epithelial), MDA-MB-231 human breast cancer cells (adenocarcinoma, mammary gland/breast, derived from metastatic site of pleural effusion, epithelial), PC-3 human prostate cancer cells (adenocarcinoma, prostate, derived from metastatic site of bone, epithelial), and HK2 human kidney cortex/proximal tubule cells (epithelial, non-cancerous, human papilloma-virus 16 transformed) were obtained from the American Type Culture Collection (ATCC). SKOV3 human ovarian cancer cells (adenocarcinoma, ovary: ascites, epithelial) and ES-2 human ovarian cancer cells (clear cell carcinoma, ovary, fibroblast) were gifts from Dr. Juntao Luo (Department of Pharmacology, SUNY Upstate Medical University). OVCAR3 cells were cultured in RPMI-1640 Medium (ATCC 30-2001) supplemented with 1× Penicillin (100 IU)/Streptomycin (100 µg/ml) (Corning 30-002-CI); SKOV3 and ES-2 cells were cultured in McCoy's 5A Medium (Lonza 12-688) supplemented with 1× Penicillin (100 IU)/Streptomycin (100 µg/ml) (Corning 30-002-CI); MDA-MB-231 cells were cultured in DMEM (Sigma-Aldrich D6429) supplemented with Antibiotic-Antimycotic (Anti-Anti) (1×) (Gibco 15240); PC-3 cells were cultured in Ham's F-12K (Kaighn's modification, with L-glutamine, Gibco 21127) Medium supplemented with Anti-Anti (1×); HK2 cells were cultured in DMEM/F12 Medium (Gibco 11320) supplemented with Anti-Anti (1×). All cells were grown with media supplemented with 10% FBS (Gibco 26140). Cells were grown in an incubator (Thermo Electron Corp., Napco series 8000 WJ, model 3578, Revco Elite II) under a humidified atmosphere of air and 5% $CO_2$ at 37° C.

FIGS. 18, 19, 20, 21, and 22 show bar graphs of free drug vs. DMA prodrug at different pH, for MDA-MD231, PC-3 dells, U87GM, SKOV3, and OVCAR3 cells, respectively.

Instruments. In the 96-well plate format, 490 nm absorbance readings for MTS cell viability assays were obtained using a BioTek ELx808 microplate reader. The pH values of treatment and incubation media were measured before and after the experiments using an Orion Ross Glass Combination Micro pH electrode connected to an Orion 3-Star Benchtop pH-meter with a BNC connector (both from Thermo Scientific).

pH-dependent anti-proliferation assays with cells. In 96-well plates, ~3,000 cells were seeded per well then grown for 24-48 hr until 30-40% confluency. After removing the growth media, cells were treated with DMA prodrug 8, DMI 7, byproduct 9, free drug Dox (positive control, with 1% DMSO), or buffer (negative vehicle control, 10 or 25 mM sodium phosphate aq. buffer 3-8% by volume; the amount of DMSO and extra phosphate in all wells were kept constant) at a given concentration and pH in modified DMEM/F-12 media (without phenol red, with 0% or 50% FBS (FIG. 5I only), supplemented with 60 mM (or 30 mM for FIG. 5I FBS experiments) of MES for pHe 6.0-6.8 or HEPES for pHe 7.2-7.8) for 1-24 hr at 37° C. in the incubator. After treatment solutions were removed, cells were incubated with normal growth media (pH 7.4, 10% FBS) and allowed to proliferate for additional 2-4 days until the buffer vehicle negative control wells have reached >80% confluency, then MTS cell viability assays (except data shown in FIG. 5I) were performed (i.e., growth media was replaced with 50 μL of pH 7.4 DMEM/F-12 media without phenol red, 10 μL of MTS reagent was added, absorbance at 490 nm was recorded 0.5-4 hr afterwards). For serum effect cell plate data shown in FIG. 5I, cell viability was measured using alamar Blue assay (i.e., growth media was replaced with 45 μL of pH 7.4 DMEM/F-12 media without phenol red, 5 μL of alamar Blue reagent (10×) was added; fluorescence at 590 nm was recorded after excitation at 560 nm at 1 hr afterwards). The pH values of treatment solutions were measured before and after each experiment to give the pH ranges reported. Results of these growth inhibition assays are shown in FIGS. 7A-7I, 8A, 8B, 9A, 9B, 10A, 10B, and 11A-11D. In all experiments, 1% of DMSO in Dox treatment solutions and mild acidic pHe in the range of 6.5-7.0 had no statistically significant effect on cell growth.

Statistical information for anti-proliferation data shown in FIG. S3 (and FIGS. S4-S7 of the ESI).

Error bars shown in FIGS. 7A-7I and 8A, 8B, 9A, 9B, 10A, 10B, and 11A-11D reflect ±1 standard deviation (SD). Statistical significance of the difference between the chosen data sets was evaluated using unpaired (unequal variance), two-tailed Student's t-test (*: P<0.05; : P<0.01; *: P<0.001). Exact numerical values of the mean±SD and the P values are reported in Table 4. Errors of the mean at 95% confidence level (CL) can be estimated using the two-tailed confidence coefficient $t_{CL,v}$ in the Student's t-test distribution with v degrees of freedom (v=n-1), according to the following equation:

$$\text{estimate of true value} \approx \overline{X}_n \pm t_{CL,v} \frac{S_n}{\sqrt{n}}$$

where $\overline{X}_n$ is the mean, $S_n$ is the sample standard deviation and n is the sample size. In previously reported results, n varied from 3 to 6. These n values reflect repeats on a single 96-well plate. The critical $t_{CL,v}$=4.303, 3.182, 2.776, and 2.571 when n=3, 4, 5 and 6, respectively. In other words, 95% confidence level standard error corresponds to 2.48, 1.59, 1.24 and 1.05 SD at n=3, 4, 5 and 6, respectively. All presented data were reproduced in at least one other plate. However, due to plate-to-plate and week-to-week cell variabilities, only data from one representative plate was plotted.

Anhydride-Activated Disulfide Bifunctional Cross-Linker 4.

Figure 44:
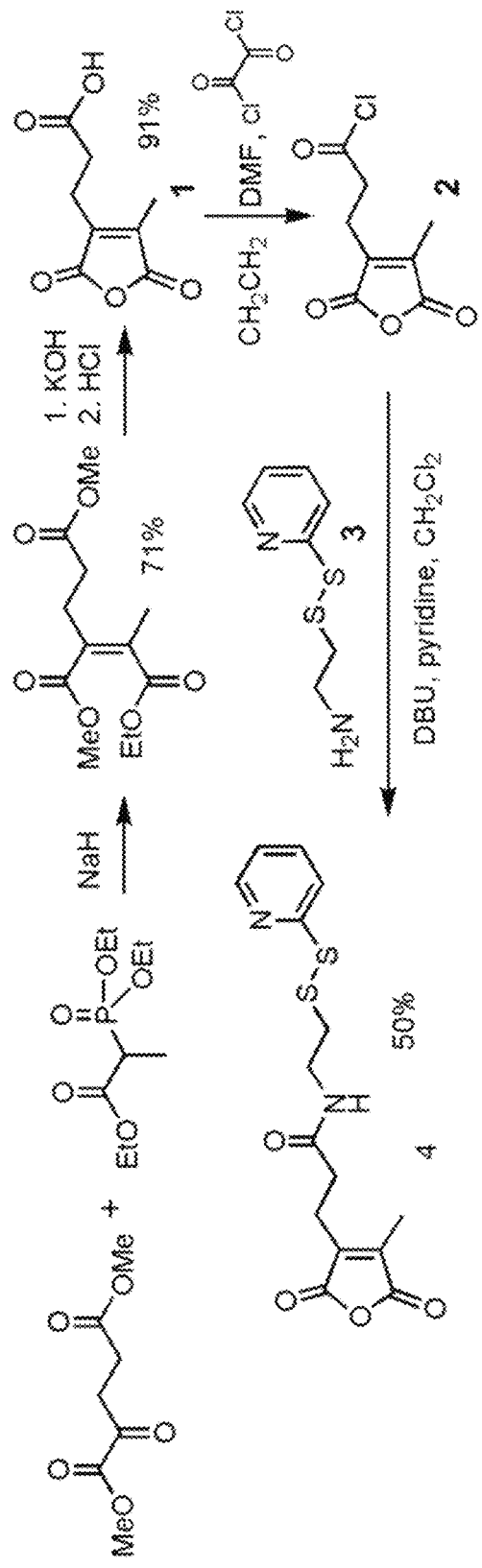
FIG. 44 shows chemical synthesis of anhydride-disulfide 4.

Chemical Synthesis of anhydride-disulfide 4 is shown in FIG. 44.

Disubstituted maleic anhydride-acyl chloride 2 was prepared in situ from 2-propionic-3-methylmaleic anhydride 1, which in turn was assembled via a Horner-Emmons reaction from dimethyl-2-oxo-glutarate and triethyl-2-phosphono-propionate, all following the procedures of Naganawa, Ichikawa, and Isobe. [Naganawa 1994] Acyl chloride 2: $^1$H NMR (600 MHz, CDCl$_3$): δ 3.31 (2H, t, $^3$J=6.9 Hz), 2.80 (2H, t, $^3$J=6.9 Hz), 2.13 (3H, s). $^{13}$C NMR (151 MHz, CDCl$_3$): δ 173.0, 165.5, 165.4, 143.3, 140.4, 43.6, 20.3, 9.9.

A solution of S-(2-pyridylthio)cysteamine HCl salt 3 (50 mg, 0.23 mmol, 1 eq., prepared following the method of Ebright et al. [Ebright 1992]), DBU (0.034 mL, 0.23 mmol, 1 eq.) and pyridine (0.027 mL, 0.34 mmol, 1.5 eq.) in 1 mL of dichloromethane was added to acyl chloride 2 (~45.6 mg, ~0.23 mmol, ~1 eq.). The resulting reaction mixture was kept at rt for 2 hr, and then directly loaded onto a silica gel column. The desired product disulfide 4 (40 mg) was isolated after chromatography (1:3 ethyl acetate/hexanes, followed by 1:1 diethyl ether/hexanes to elute the hydrolyzed carboxylic acid byproduct 1, and then 1:1 ethyl acetate/hexanes to 5:2 ethyl acetate/hexanes) as oil in 50% yield over two steps from 2-propionic-3-methylmaleic anhydride 1. Anhydride-disulfide 4: IR (KBr): 3413 (br), 3295 (br), 3065 (br), 2926, 1824, 1765, 1672, 1653, 1576, 1560, 1541, 1446, 1419, 1281, 1119, 908, 766, 733 cm$^1$. $^1$H NMR (600 MHz, CDCl$_3$) δ 8.50 (1H, d, J=4.6 Hz), 7.67-7.64 (1H, m), 7.57 (1H, br), 7.52 (1H, d, J=8.0 Hz), 7.20-7.18 (1H, m), 3.53-3.50 (2H, m), 2.90 (2H, t, J=5.8 Hz), 2.78 (2H, t, J=7.1 Hz), 2.58 (2H, t, J=7.1 Hz), 2.09 (3H, s). $^{13}$C NMR (151 MHz, CDCl$_3$) δ 170.7, 166.04, 165.96, 158.9, 149.4, 142.9, 142.2, 137.7, 121.8, 121.7, 38.9, 37.5, 33.1, 20.5, 9.7. MS (ESI+): Exact Mass Calculated for $C_{15}H_{16}N_2O_4S_2$ [M+H$^+$]$^+$: 353.1. Found: 352.9.

Doxorubicin Disubstituted Maleamic Acid Glutathione Conjugate (Dox-DMA-GSH) 8a/b.

Activation of pre-prodrug Dox-DMI-GSH 7 to prodrug Dox-DMA-GSH 8a/8b is shown in FIG. 45.

Sample preparation for mass analysis. A solution of Dox-DMI-GSH 7 (53.7 μg, 50 nmol, 357 μM) in 140 μL of aq. triethyl ammonium acetate (3.57 mM)/triethyl amine (3.57 mM) buffer with final pH of 9.9 was allowed to react at rt in the dark. After 10 min, pH of reaction mixture decreased to 9.6; thus, 25 μL of 10 mM triethyl ammonium acetate/10 mM triethyl amine aq. buffer (solution A) was added to adjust pH back to 9.9. After 1 hr, HPLC at pH 2-3 (condition C) showed that >70% of doxorubicin (tR 23.7 min) was released during HPLC, suggesting >70% DMI 7 (tR 25.0 min) had been converted to DMA 8a/b (which are not stable at pH 2-3). At 1.5 hr, the reaction mixture pH again decrease to 9.5, and 30 μL of solution A was added to adjust pH back to 9.9. After 2 hr, 2 μL of 100 mM aq. acetic acid solution was added to the reaction mixture to adjust pH to 8.2. The resulting solution was submitted for mass analysis (~24 hr at rt en route). MS (ESI-): exact mass calculated for Dox-DMA-GSH 8a/b $C_{47}H_{57}N_5O_{21}S_2$ [M–H$^+$]$^-$: expected 1090.3, found 1090.5; [M–2H$^+$]$^{-2}$: expected 544.7, found 545.2. Dox-DMI-GSH 7 was also present in the solution (exact mass calculated for Dox-DMI-GSH 7 $C_{47}H_{55}N_5O_{20}S_2$ [M–H$^+$]$^-$: expected 1072.3, found 1072.4).

Sample preparation for HPLC Dox release assay in phosphate buffer at rt. To a solution of Dox-DMI-GSH 7 (26.9 μg, 25 nmol, 25 μM) in 1 mL of 25 mM aq. sodium phosphate buffer (pH 8) was added small aliquots of 1 M aq. NaOH to adjust the pH to 9.9. The reaction solution was allowed to stand at rt for 1 hr in the dark, during which the pH decreased to 9.6. Reaction progress was monitored using pH 8 HPLC (condition D): s.m. Dox-DMI-GSH 7 tR 23.8 min, desired product Dox-DMA-GSH 8a/b tR 21.4 min and 21.8 min. After 1 hr, the pH of Dox-DMA-GSH 8a/b solution was adjusted to desired pH for doxorubicin release assays at RT (FIGS. 5A-5I, Table 1).

Sample preparation for HPLC Dox release assay in phosphate buffer at 37° C. To a solution of Dox-DMI-GSH 7 (86 µg, 80 nmol, 100 µM) in 800 µL of 25 mM aq. sodium phosphate buffer (pH 8) was added small aliquots of 1 M aq. NaOH to adjust the pH to 9.9. The reaction solution was allowed to stand at rt for 1 hr in the dark, during which the pH decreased to ~9.6. Reaction progress was monitored using pH 8 HPLC (condition E): s.m. Dox-DMI-GSH 7 tR 21-22 min, desired product Dox-DMA-GSH 8a/b tR 18-20 min. After 1 hr, the pH of Dox-DMA-GSH 8a/b solution was adjusted to desired pH and kept at 37° C. for doxorubicin release assays (FIG. 6A-B, Table 2).

Sample preparation for HPLC Dox release assay with 45% FBS at 371 WC. To a solution of Dox-DMI-GSH 7 (107.4 µg, 100 nmol, 1 mM) in 100 µL of 25 mM aq. sodium phosphate buffer (pH 8) was added small aliquots of 1 M aq. NaOH to adjust the pH to 9.9. The reaction solution was allowed to stand at rt for 1 hr in the dark, during which the pH decreased to 9.6. Reaction progress was monitored using pH 8 HPLC condition E. After 1 hr, the pH of Dox-DMA-GSH 8a/b solution was adjusted to pH 8, then mixed with 900 µL of 0.2 micron-filtered 1:1 FBS/DMEM-F12 with 1% Anti-Anti. The pH of Dox-DMA-GSH 8a/b solution in 10:45:45 aq. 25 mM phosphate/FBS/DMEM-F12 was adjusted to desired pH and kept at 37° C. for doxorubicin release assays (FIG. 6C-D, Table 3).

Sample preparations for pH-dependent anti-proliferation assays with cells.

Figure 23:
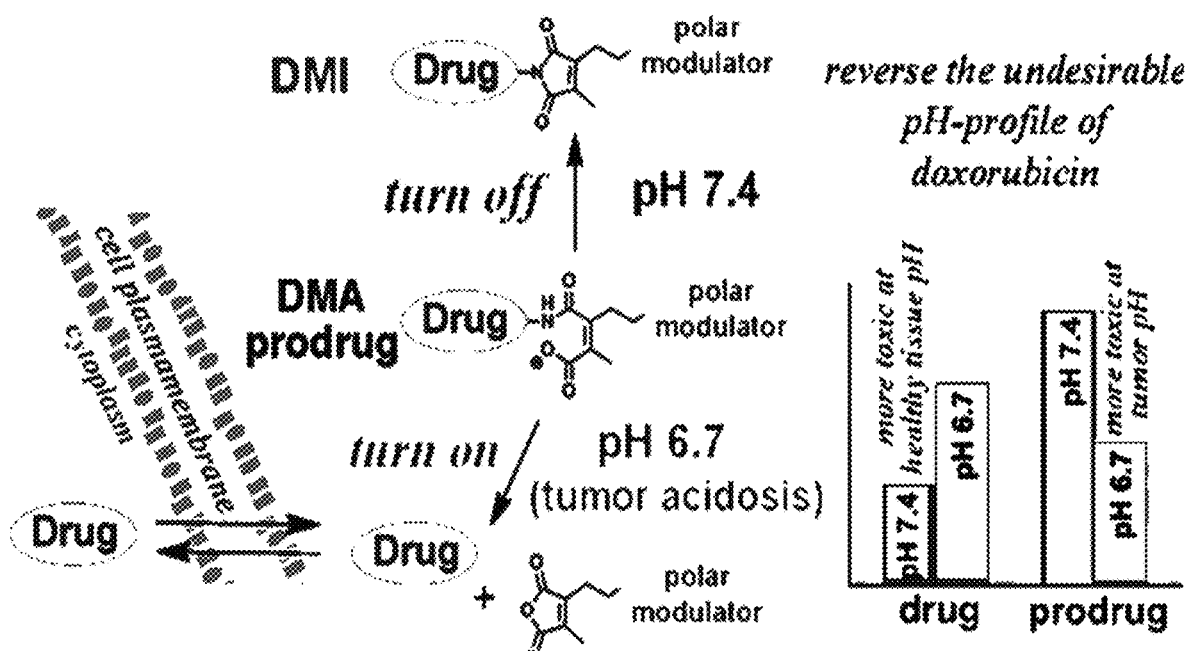
FIG. 23 shows a schematic drawings of pH dependent drug delivery.

FIG. 23 shows a schematic drawings of pH dependent drug delivery.

General Procedure: To a 300 µM solution of Dox-DMI-GSH 7 (30 nmol) in 100 µL of 25 mM aq. sodium phosphate buffer (pH 8) was added small aliquots of 0.1 M aq. NaOH to adjust the pH to 9.9. The reaction solution was allowed to stand at rt for 1 hr in the dark, during which the pH decreased to ~9.6. After 1 hr, the reaction solution was split into two 50-µL portions (for pH 7.4 vs. pH 6.2-6.8 cell experiments). The pH of one portion was adjusted to pH 8 (for pH 7.4 cell experiments) or pH 7 (for pH 6.2-6.8 cell experiments). Subsequently, the solution was diluted 30-fold (to 10 µM) with pH 7.4 or pH 6.2-6.8 cell media (final volume 1.5 mL) and then filtered (0.2 micron) before used in cell experiments.

For data shown in FIG. 7 (50% serum effect experiment), a similar procedure was used except the following: (a) A 100 µM solution of Dox-DMI-GSH 7 (22 nmol) in 220 µL of 10 mM aq. sodium phosphate buffer (pH 8) was used for conversion to DMA 8 at pH 9.9; (b) Subsequently, the DMA 8 solution was adjusted to pH 8, filtered (0.2 micron), and then diluted 17- to 50-fold (to ~2-6 µM final [DMA 8] concentration) with pH 7.4 or pH 6.7 cell media (DMEM-F12 without phenol red or 1:1 DMEM-F12 without phenol red/FBS) (final volume 250 µL per specific pH and dose). Small amounts of 10 mM aq. sodium phosphate buffer (pH 8) was added to the more diluted sample solutions to keep the final concentration of sodium phosphate constant across samples of different DMA dose.

For data shown in FIGS. 7D and 7H (concentration scan from 3 nM to 30 µM), a similar procedure was used except the following: (a) A 187 µM solution of Dox-DMI-GSH 7 (75 nmol) in 400 µL of 10 mM aq. sodium phosphate buffer (pH 8) was used for conversion to DMA 8; (b) Subsequently, the DMA 8 solution was adjusted to pH 8, filtered (0.2 micron), and then diluted to 10 µM and 30 µM stocks with pH 7.4 or pH 6.7 cell media (DMEM-F12 without phenol red), followed by serial dilutions to give the final concentrations (final volume 450 µL per specific pH and dose).

FIGS. 7A-7I show that prodrug 8 can reverse the unfavorable pH-profile of Dox. Cells were treated with Dox (positive control), Dox-DMA-GSH prodrug 8, Dox-DMI-GSH 7, or buffer (negative control) under the conditions specified (no serum except for i), then grown for 2-4 d before counting in viability assays. Percentages shown are normalized to buffer at pH 7.4. The pH values of the treatment solutions were measured before and after each experiment to give the ranges reported. Error bars reflect ±one standard deviation (SD) (except for (d) they represent 95% confidence level from fitting, see FIGS. 11A-11D). Statistical significances of the differences between the chosen data sets were evaluated using unpaired (with unequal variance), two-tailed Student's t-test (*: Po 0.05; : Po 0.01; *: Po 0.001). Exact numerical values of the mean, the SD and the P values are reported in the ESI, Table 4.

Figure 40:
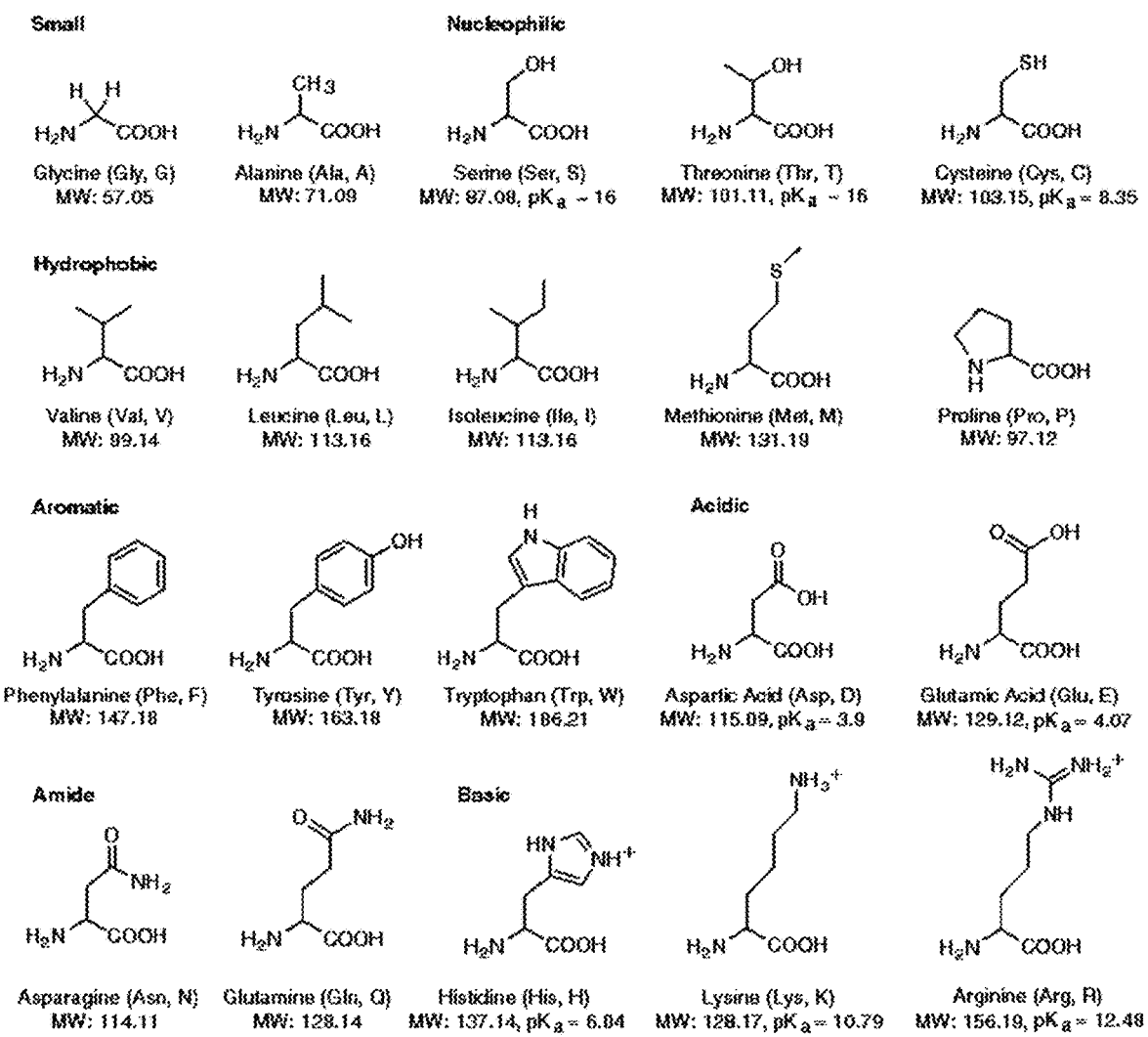
FIG. 40 shows the canonical structures for the 20 common amino acids.

Structures of Dox-DMA linker only prodrug and its precursor DMI preprodrug (stable shelf life, the product) are shown in FIG. 37, while FIG. 38 shows Dox-DMA linker-Glu-peptide prodrug and its precursor DMI, and FIG. 39 shows Dox-DMA linker-dipeptide prodrug and its precursor DM. FIG. 40 shows the canonical structures for the 20 common amino acids.

Figure 41:
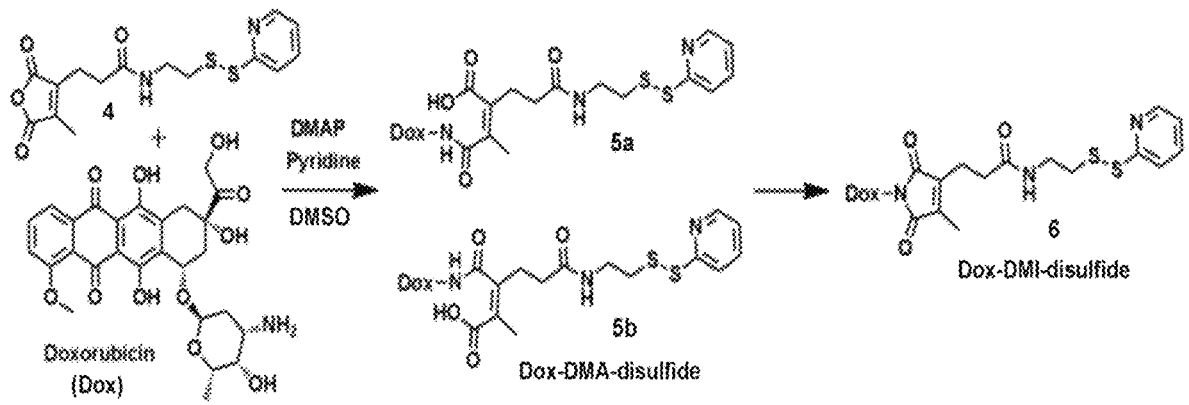
FIG. 41 shows a process for forming Dox-DMI-disulfide 6 from Dox and DMI-disulfide 4, by cyclization in DMAP Pyridine in DMSO, with Dox-DMA-disulfide 5a/5b as intermediates.

FIG. 41 shows a process for forming Dox-DMI-disulfide 6 from Dox and anhydride-disulfide 4, by cyclization in DMAP Pyridine in DMSO, with Dox-DMA-disulfide 5a/5b as intermediates.

Doxorubicin Disubstituted Maleamic Acid Disulfide Conjugate (Dox-DMA-Disulfide) 5a/b and Doxorubicin Disubstituted Maleimide Disulfide Conjugate (Dox-DMI-Disulfide) 6.

To a solution of 33 mg of doxorubicin, HCl salt (58 µmol, 1 eq.), 14 mg of DMAP (114 µmol, 2 eq.) and 14 µL of pyridine (13 mg, 170 µmol, 3 eq.) in 500 µL of DMSO was added a solution of 20 mg of anhydride-disulfide cross-linker 4 (58 µmol, 1 eq.) in 250 µL of DMSO. The reaction mixture was kept in the dark at rt. HPLC condition A (pH 8-8.5, see general procedures of HPLC section for details) showed that Dox-DMA-disulfide regioisomers 5a/b (tR 24.6-25.9 min) were formed within 15 min, which over time (5 days) slowly converted to Dox-DMI-disulfide 6 (tR 32.0-32.8 min). The product Dox-DMI-disulfide 6 (37 mg) was purified by HPLC condition B to give a yield of 74% from compound 4.

Dox-DMA-disulfide 5a/b: MS (ESI−), exact mass calculated for $C_{42}H_{45}N_3O_{15}S_2$ [M−H$^+$]$^-$: 894.2, found 894.6. (Dox-DMI-disulfide 6 also present, exact mass calculated for $C_{42}H_{43}N_3O_{14}S_2$ [M−H$^+$]$^-$: 876.2, found 876.6). The MS data of Dox-DMA-disulfide 5a/b are shown in FIG. S14 of the ESI. Dox-DMI-disulfide 6: $^1$H NMR (600 MHz, DMSO) δ 13.91 (1H, s), 13.14 (1H, s), 8.39-8.35 (1H, m), 8.04 (1H, t, J=5.6 Hz), 7.82-7.77 (2H, m), 7.77-7.72 (1H, m), 7.65 (1H, d, J=8.1 Hz), 7.55 (1H, d, J=8.3 Hz), 7.19-7.15 (1H, m), 5.28 (1H, s, br), 4.92-4.87 (1H, m), 4.59 (2H, s), 4.25 (1H, q, J=6.4 Hz), 4.17 (1H, d, J=13.8 Hz), 3.92 (3H, s), 3.40 (1H, s, br), 3.28-3.23 (2H, m), 3.11-3.04 (1H, m), 2.94 (1H, d, J=17.9 Hz), 2.83 (1H, d, J=17.9 Hz), 2.78 (2H, t, J=6.7 Hz), 2.51-2.46 (2H, m), 2.27-2.18 (3H, m), 2.12-2.05 (1H, m), 1.80 (3H, s), 1.58 (1H, dd, J=3.1, 12.1 Hz), 1.12 (3H, d, J=6.4 Hz). $^{13}$C NMR (151 MHz, CDCl3) δ 213.8, 186.3, 186.1, 172.0, 171.7, 170.9, 160.7, 159.0, 156.1, 154.5, 149.5, 138.5, 137.7, 137.0, 136.1, 135.3, 134.5, 134.0, 121.1, 119.8, 119.6, 119.3, 118.9, 110.6, 110.5, 100.5, 74.8, 70.2, 68.7, 66.6, 63.7, 56.5, 49.5, 37.7, 37.3, 36.5, 33.1, 31.9, 26.7, 19.4, 17.0, 8.4. MS (ESI*): exact mass calculated for $C_{42}H_{43}N_3O_{14}S_2$ [M+H$^+$]$^+$: 878.2, found 878.4. The $^1$H NMR and $^{13}$C NMR spectra of Dox-DMI-disulfide 6 are shown in FIGS. S15 and S16 of the ESI, respectively. The MS data of Dox-DMI-disulfide 6 is shown in FIG. S17 of the ESI.

Figure 43:
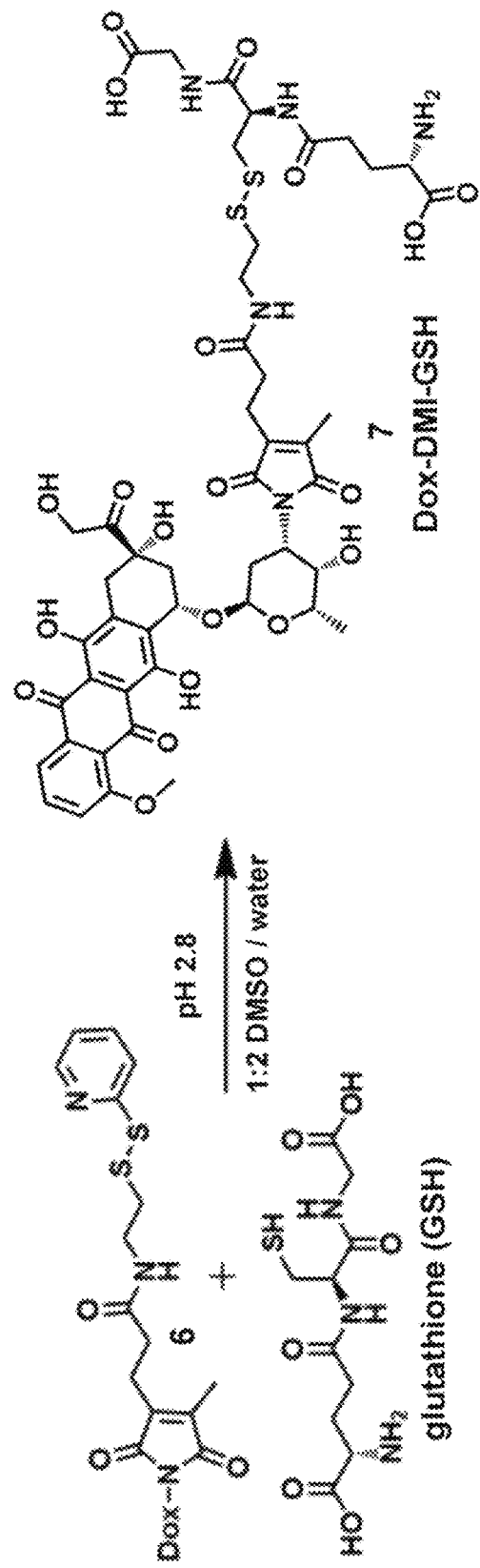
FIG. 43 shows formation of Dox-DMI-GSH from Dox-DMI-disulfide and GSH in 1:2 DMSO/water at pH 2.8.

FIG. 43 shows formation of Dox-DMI-GSH from Dox-DMI-disulfide and GSH in 1:2 DMSO/water at pH 2.8. Doxorubicin Disubstituted Maleimide Glutathione Conjugate (Dox-DMI-GSH) 7.

To a solution of Dox-DMI-disulfide 6 (10 mg, 11.4 μmol, 1 eq.) in 287 μL of DMSO was added glutathione free acid (7 mg, 22.8 μmol, 2 eq.) and 574 μL of water. The mixture was vortexed until all components dissolved, and the resulting pH 2.8 solution (pH was measured on a sample prepared by diluting 20 μL of reaction mixture with 30 μL of water) was kept at rt in the dark for 1 hr. The reaction progress was monitored (s.m. Dox-DMI-disulfide 6 tR 31.1 min, product Dox-DMI-GSH 7 tR 25.0 min), and the desired product (8.6 mg, 70% yield) was isolated using HPLC condition C (see FIG. S21 of the ESI for HPLC traces).

Formation of Dox-DMI-GSH 7 via disulfide exchange as followed by HPLC (pH 3) is shown in FIG. S21 of the ESI. The starting material (s.m.) Dox-DMI-disulfide 6 had a retention time (tR) of 31.1 min, while the desired product Dox-DMI-GSH 7 had a tR of 25.0 min. The facile activated disulfide exchange reaction was essentially complete within 10 min, (likely catalyzed by the acidic condition and protonation of the 2-mercaptopyridyl leaving group on the N atom). No other side-product was detected (the reaction was peak-to-peak). The 25 min peak was isolated to give the desired product 7 (8.6 mg) in 70% yield (the rest of the material is likely lost due to normal process of HPLC because the reaction scale is small).

Dox-DMI-GSH 7: $^1$H NMR (600 MHz, DMSO-d6) δ 13.91 (1H, s), 13.15 (1H, s), 8.39-8.32 (2H, m), 8.29 (3H, s, br), 8.03 (1H, t, J=5.6 Hz), 7.88-7.78 (2H, m), 7.56 (1H, d, J=8.4 Hz), 5.28 (1H, s, br), 4.92-4.86 (1H, m, br), 4.59 (2H, s), 4.54 (1H, dt, J=4.5, 9.0 Hz), 4.24 (1H, q, J=6.5 Hz), 4.17 (1H, d, J=13.9 Hz), 3.98-3.90 (1H, m), 3.93 (3H, s), 3.74 (2H, d, J=5.9 Hz), 3.40 (1H, s), 3.30-3.23 (2H, m), 3.11-3.03 (2H, m), 2.98-2.91 (1H, m), 2.87-2.77 (2H, m), 2.70 (2H, t, J=6.6 Hz), 2.48 (2H, t, J=7.4 Hz), 2.42-2.34 (1H, m), 2.34-2.27 (1H, m), 2.23 (2H, t, J=7.6 Hz), 2.26-2.18 (1H, m), 2.10-1.92 (3H, m), 1.82 (3H, s), 1.59-1.53 (1H, m), 1.12 (3H, d, J=6.4 Hz). $^{13}$C NMR (151 MHz, DMSO) δ 213.8, 186.4, 186.3, 172.1, 171.8, 171.2, 171.0, 170.9, 170.8, 170.3, 160.8, 156.1, 154.5, 138.6, 137.0, 136.2, 135.4, 134.6, 134.1, 119.9, 119.7, 119.0, 110.7, 110.6, 100.5, 74.8, 70.1, 68.8, 66.6, 63.7, 56.6, 51.8, 51.7, 49.5, 40.8, 40.6, 37.9, 37.0, 36.5, 33.1, 32.0, 30.7, 26.7, 25.9, 19.4, 16.9, 8.4. MS (ESI+): exact mass calculated for $C_{47}H_{55}N_5O_2O_{20}S_2$ [M+H$^+$]$^+$: 1074.3, found 1074.4; calculated for [M+Na$^+$]$^+$: 1096.3, found 1096.4.

Figure 14:
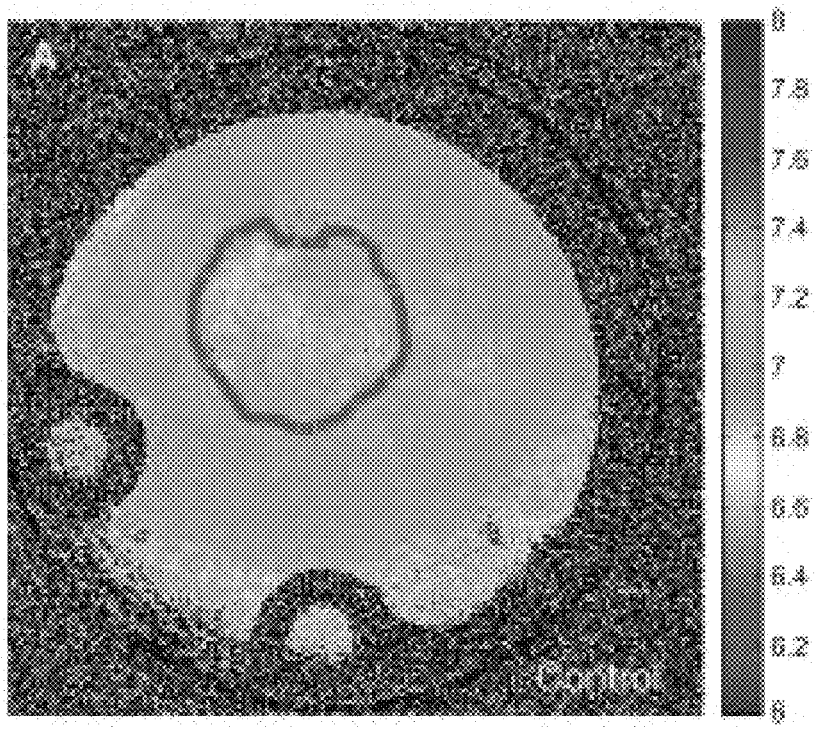
FIG. 14 (prior art) shows that solid tumor acidity (extracellular pH) is heterogeneous but mostly in the range of pH 6.5-7.0. (from I. F. Robey et al. Cancer Research 2009, 69: (6) p 2260-2268).

Di-substituted Maleamic Acid as an Ultra-sensitive, Cleavable Linker for Reversing the Cytotoxicity pH-profile of Doxorubicin Many cancerous tumors have extracellar pH (pHe) in the range of 6.5-7.0, with average pHe of 6.8, compared with that of 7.2-7.4 in healthy tissues. This small difference of about half pH unit presents an exciting novel opportunity, as well as a great challenge, for selective drug delivery to cancer cells. Tumor acidosis can reduce the effectiveness of chemotherapy by decreasing the membrane permeability of amine drugs such as doxorubicin (Dox), topotecan, and vinblastine. Current pH-sensitive cleavable linkers, such as ketal, acetal, cyclic orthoester, imine, acylhydrazone, boronate, and mono-substituted maleamic acid (i.e., cis-aconityl linker), can respond to endosomal acidity of pH 4.5-6.0, but they are not sensitive enough for triggering by tumor acidosis pHe. To address this need, super-sensitive, di-substituted maleamic acid (DMA) linkers were studied. and found that it is cleaved at pH 6.5-6.7 in ~12 hr (35-50% Dox release) compared to ~4 days (20-30% Dox release) at pH 7.4-7.6. The pH 6.5/7.4 release ratio is improved from the previous known best of 2:1 (in terms of concentration of drug released, using cyclic orthoester) to ~5:1 (at 9 hr). The closed maleimide form (DMI) is a major side-product (15-50%) during drug release at all pH values, as well as a convenient synthetic precursor of DMA for ease of handling and storage. Finally, conjugating Dox to glutathione (a membrane-impermeable peptide) via DMA gave a prodrug of Dox that is more toxic under acidic conditions than neutral pH, reversing the pH-profile of free drug cytotoxicity. Such DMA-linked prodrug of Dox may improve chemotherapy by reducing off target side-effects. FIG. 14 shows the solid tumor acidity (extracellular pH), which is heterogeneous, but mostly in the range of pH 6.5-7.0.

The DMA linker cleaves at pH 6.5 with a half-life of ~10 hr compared to that of ~4 days at pH 7.4. This DMA linker can be used for pH-dependent drug release, as shown above with Dox-DMA-GSH conjugate.

Example 2

The extracellular pH (pHe) difference between cancerous tumors (pHe 6.5-6.9) and healthy tissues (pHe 7.2-7.4) presents an opportunity for improving chemotherapy through pH-selective drug release. The minute pHe difference is beyond the reach of current pH-responsive prodrugs, which are generally triggered by lysosomal acidity of pH 4-6. A class of doxorubicin (Dox) prodrugs with ultrahigh pH-sensitivity is provided. In response to pH 6.5-6.9, these prodrugs release free Dox via cleavage of the di-substituted maleamic acid (DMA) linker. While all DMA prodrugs demonstrated pH-selectivity, structural variations in the polar modulator moiety influenced the kinetics of drug release. Any prodrug cleavable at such slight acidity will have concerns regarding background drug release at pH 7.4 and instability during storage and handling. The latter challenge is met by using the di-substituted maleimide (DMI) derivative as the pre-prodrug (and converting DMI pre-prodrug to DMA prodrug just prior to use). Furthermore, DMI formation also suppressed background drug release at pH 7.4. The most effective prodrug released 6-fold more Dox at pH 6.5 than 7.4. These DMA-based prodrugs may improve the therapeutic index of Dox.

Figure 15:
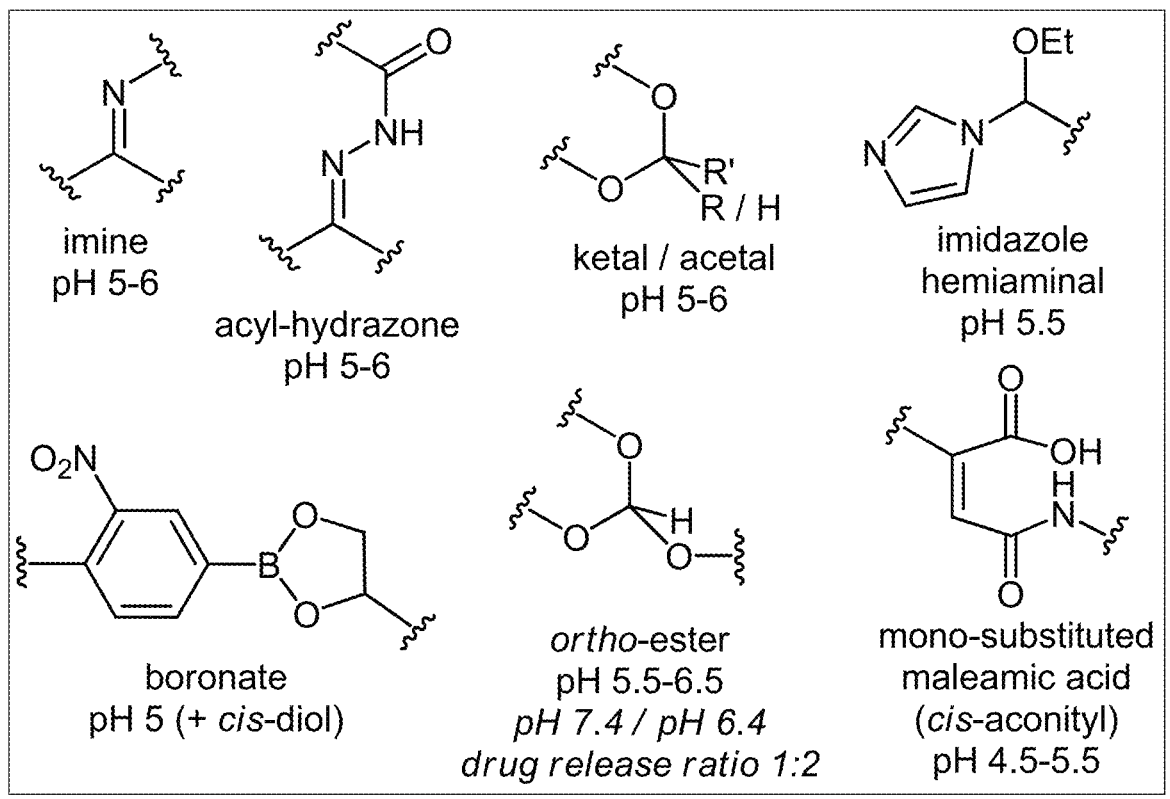
FIG. 15 shows that most acid-sensitive linkers are designed to respond to acidity in endosomes/lysosomes (pH 4.5-6.0)

FIG. 15 shows that most acid-sensitive linkers are designed to respond to acidity in endosomes/lysosomes (pH 4.5-6.0)

Figure 16:
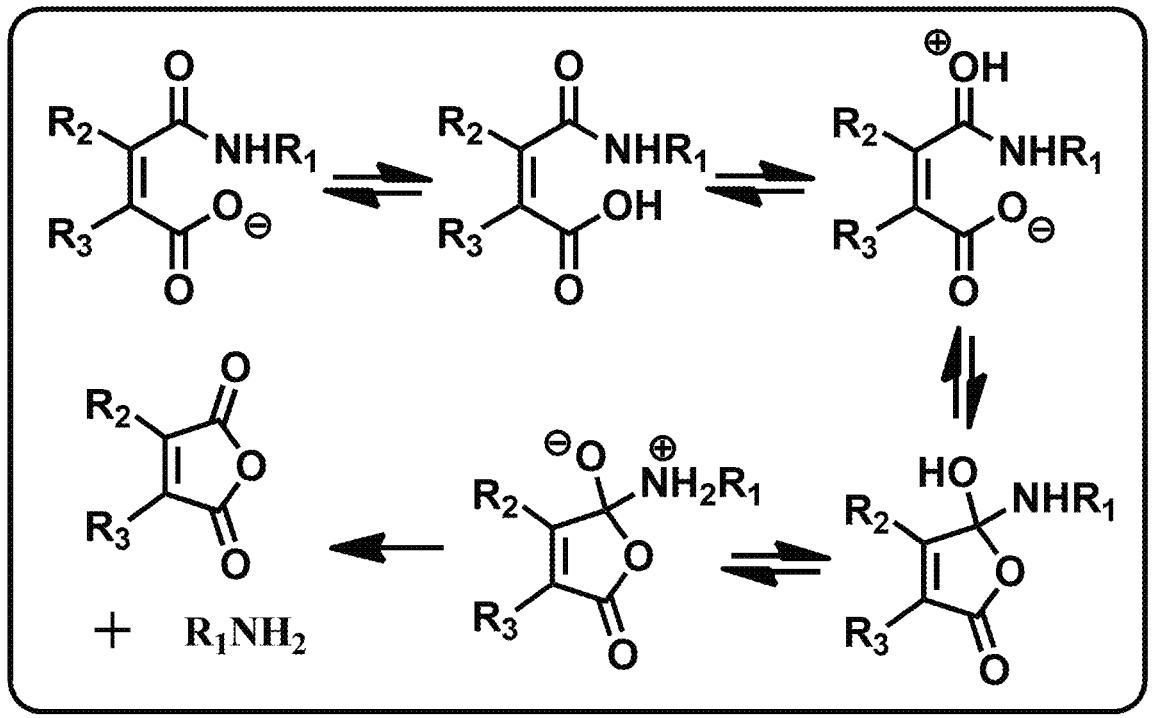
FIG. 16 shows a super-sensitive Linker: Di-substituted maleamic acid (DMA) linker, which has been used for polymer nanoparticle charge reversal in response to tumor acidosis.
Figure 20:
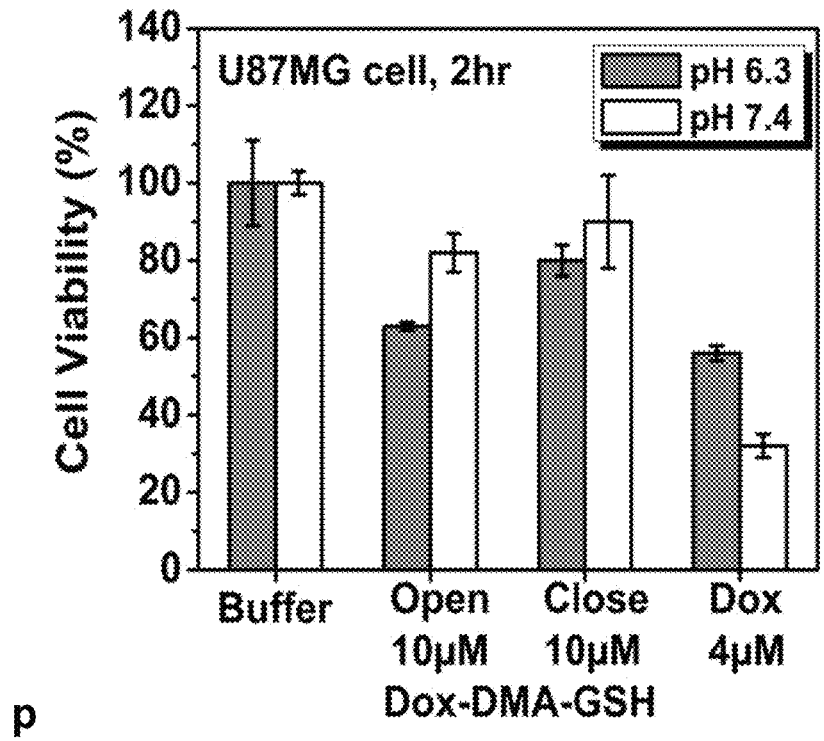
Figure 21:
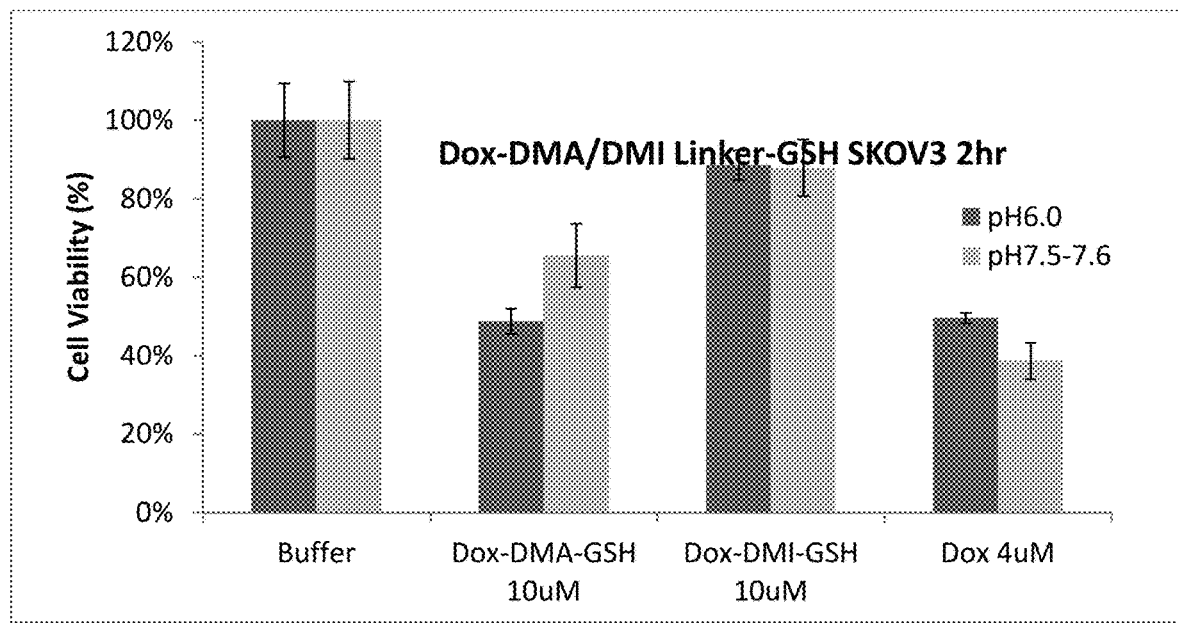
Figure 22:
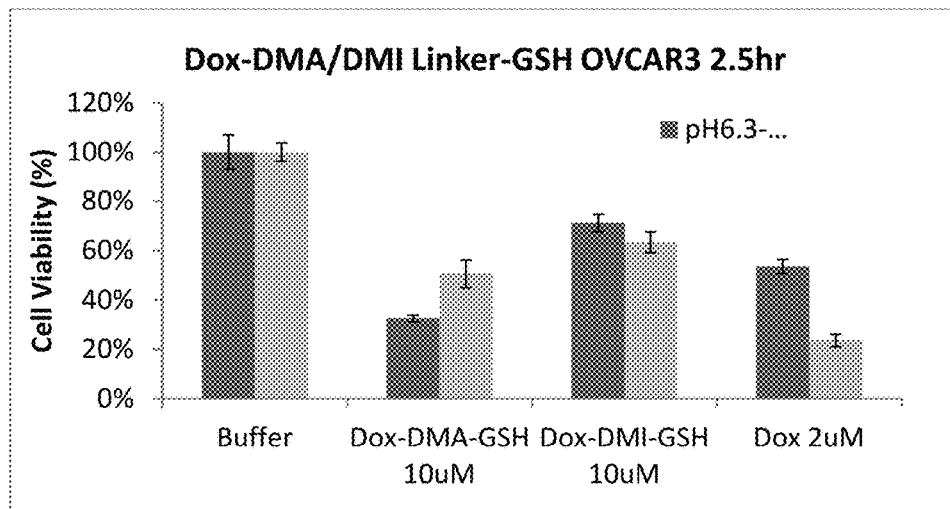

FIG. 16 shows a super-sensitive Linker: Di-substituted maleamic acid (DMA) linker, which has been used for polymer nanoparticle charge reversal in response to tumor acidosis.

FIG. 17 shows an overall Synthesis of DMI-prodrug (convert to DMA just prior to use).

Results and Discussion

Design of DMA prodrugs and DMI pre-prodrugs of Dox. The therapeutic target of Dox is DNA. In order for Dox to be active against cancer cells, it needs to reach the nucleus of the cell. The protonated ammonium form of Dox intercalates into DNA and inhibits topoisomerase II, which lead to cell death by a variety of mechanisms. The DMA linker is attached to the amino group of Dox, which is involved in binding to DNA. Thus, the linker conjugation would make the prodrug inactive or less active against cancer cells. The mechanisms by which Dox harms healthy tissues may involve targets other than DNA, as Dox is also an iron chelator that can damage membranes and proteins through Fenton chemistry and reactive oxygen species. To ensure the DMA prodrug is inactive in healthy tissues, the prodrug is kept outside of cells. Thus, the drug (e.g., Dox) is attached to a polar modulator moiety to make the prodrug membrane impermeable. This feature also makes likely that the prodrug should only respond to extracellular acidity rather than endosomal/lysosomal acidity. Under the acidotic tumor microenvironment, Dox should be released outside of the cancer cells through DMA cleavage. The released free drug molecules then cross plasma-membrane and accumulate in nucleus.

Figure 13:
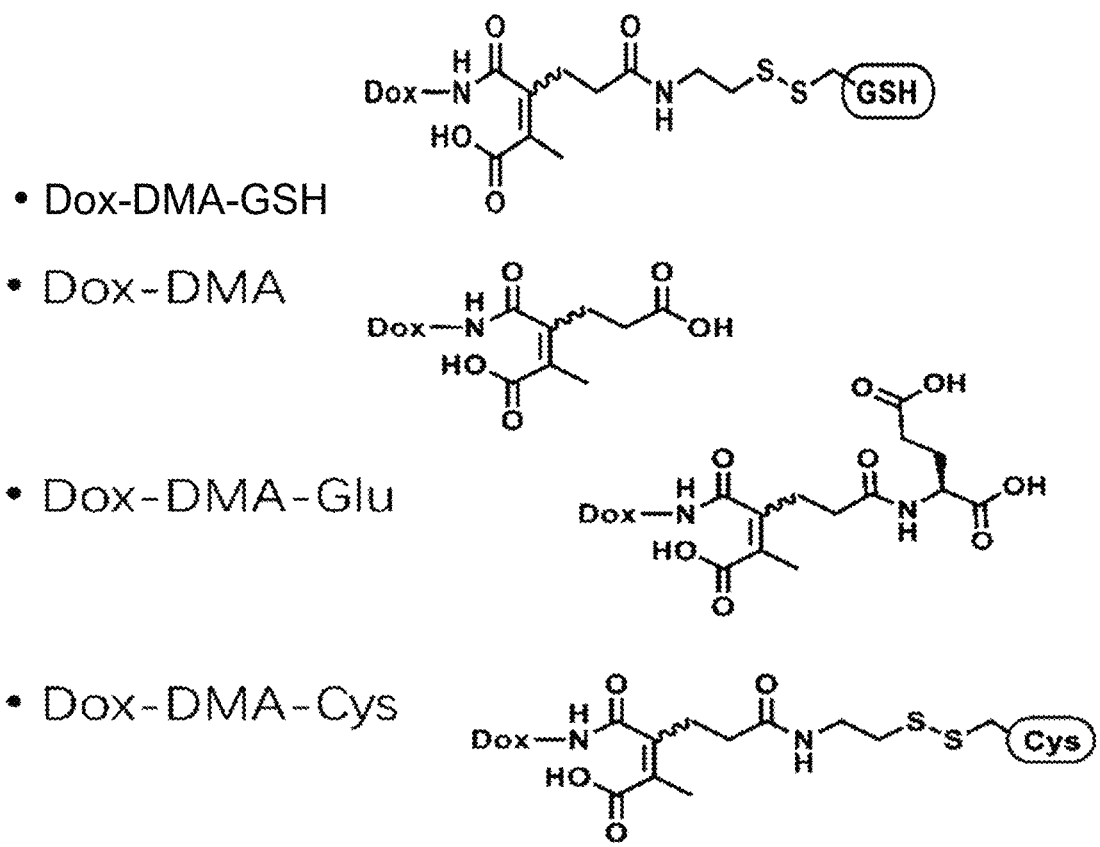
FIG. 13 shows structures for Dox-DMA-GSH, Dox-DMA, Dox-DMA-Glu, and Dox-DMA-Cys.

FIG. 13 shows structures for Dox-DMA-GSH, Dox-DMA, Dox-DMA-Glu, and Dox-DMA-Cys.

Three prodrugs that vary in the polar modulator portion are studied, as shown in FIG. 3A-3C and FIG. 4. In the simplest case, the linker itself is the polar modulator in the prodrug Dox-DMA 2a/b. The DMA group contains one negative charge in the carboxylate. There is a second carboxylate negative charge at the other end of the linker. Thus, Dox-DMA 2a/b has a formal charge of '−2' at pH 6-8. Dox-DMA-Glu 4a/b has a glutamic acid conjugated to the linker via an amide bond. The glutamate is a polar modulator with two negative charges, giving Dox-DMA-Glu 4a/b a formal charge of '−3' at pH 6-8. In Dox-DMA-Cys 6a/b, the polar modulator cysteine has its sidechain conjugated to the extended linker via a disulfide bond. The cysteine residue has a positive charge and a negative charge, and is overall zwitterionic and neutral, giving Dox-DMA-Cys 6a/b a formal charge of '−1' at pH 6-8. The disulfide containing prodrug Dox-DMA-Cys 6a/b can be considered as the simplified version of the previously reported Dox-DMA-GSH prodrug, with the Cys residue replacing the glutathione (GSH) as the polar modulator.

Figure 42:
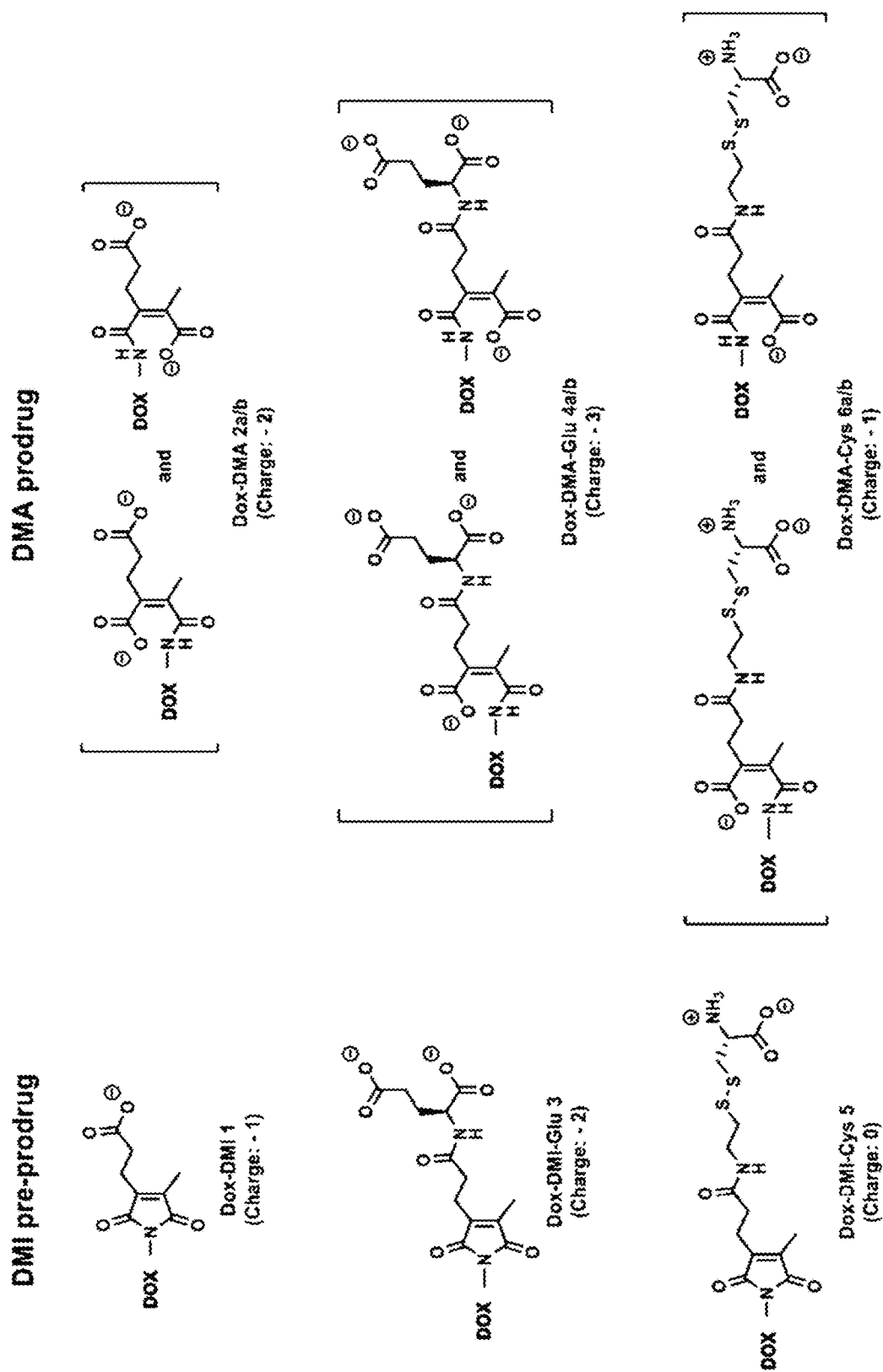
FIG. 42 shows structures of the DNA prodrugs and DMI pre-prodrugs.

The DMA linker group is unstable during handling or storage, which makes its practical use challenging or even questionable. The cyclized DMI form is stable and can be converted to the DMA prodrug in a facile fashion. Thus, the DMI form can serve as a convenient precursor to the prodrug (the pre-prodrug), offering a way to overcome DMA instability during prodrug synthesis and storage. Structures of the DMI pre-prodrugs are shown in FIG. 42.

Syntheses of DMI pre-prodrugs. Crosslinkers anhydride-acid 7 and anhydride-acyl chloride 8 were prepared following the methods of Isobe and co-workers. Towards pre-prodrug Dox-DMI-Glu 3, acyl chloride 8 was combined with L-glutamic acid di-t-butyl ester to give amide 9 in 60% yield over two steps. Deprotection of 9 through treatment with trifluoroacetic acid (TFA) provided anhydride 10 in 78% yield (FIG. 3A). Subsequently, to obtain the DMI pre-prodrugs 1 and 3, anhydrides 7 and 10 were treated with Dox (HCl salt) in the presence of 4-dimethylaminopyridine (DMAP). The DMA intermediates 2a/b and 4a/b were formed quickly after 1 h, followed by slow intramolecular cyclization to give Dox-DMI 1 and Dox-DMI-Glu 3 in 47% and 53% yield, respectively (FIG. 3B). Towards the pre-prodrug Dox-DMI-Cys 5, compound 11, which is an activated disulfide derivative of Dox with the DMI linker already installed, was prepared as described previously. Disulfide exchange between 11 and L-cysteine HCl gave Dox-DMI-Cys 5 in 85% yield (FIG. 3C).

Converting DMI pre-prodrugs to DMA prodrugs. To circumvent practical difficulties associated with DMA prodrugs of Dox, the stable DMI pre-prodrugs were converted to DMA prodrugs just prior to use. Treating DMI pre-prodrugs 1, 3 and 5 with a pH 10 aq. phosphate buffer at 37° C. for 1 hour gave DMA prodrugs 2a/b, 4a/b and 6a/b in high yields (usually 90-95% conversions, FIG. 4). Two isomers are generated depending on which carbonyl of the DMI ring was attacked by hydroxide.

Drug release vs. DMI formation: 'switch on' or 'switch off'. Subsequently, the pH of the DMA prodrug solution was adjusted to the desired experimental value in HPLC drug release assays or antiproliferation assays with cancer cells. In response to slight acidity, the DMA prodrug would 'switch on' to release Dox (FIG. 4). The byproduct of drug release is the anhydride (i.e. compounds 7, 10, 12), which will be shown below to be harmless to cells. At pH 7.4, the metastable DMA prodrug would slowly 'switch off' to form the stable, cyclized DMI byproduct (same structure as the pre-prodrug), limiting background drug release. Zhang et al. provides a detailed discussion of the competing mechanisms of drug release vs. DMI formation.

The pH-dependence of drug release from Dox-DMA prodrugs as followed in HPLC assays. To test the pH-sensitivity of drug release, solutions of a DMA prodrug were adjusted to have pH values between 6.0 and 7.4. Then Dox release and DMI formation were allowed to proceed at room temperature (rt, ~25° C.) or 37° C. The disappearance of DMA prodrug (s.m. consumption) and the appearances of Dox (free drug released), DMI byproduct, and other minor Dox-containing decomposition products (usually less than 10%), were followed with HPLC by tracking the absorbance of Dox at 480 nm. The HPLC runs were carried out with pH 8 solvents so that the DMA prodrug would not decompose during the HPLC analysis. Areas under the peaks were integrated to give the percentages.

FIGS. 24A-24F. pH-dependent drug release of Dox-DMA 2a/b at rt in aq. phosphate buffer. The dynamic conversion processes from Dox-DMA 2a/b to Dox or Dox-DMI 1 were monitored at pH 7.4 (24A), 7.0 (24B), 6.8 (24C), 6.5 (24D), 6.3 (24E), or 6.0 (24F). Shown in black is the consumption of the Dox-DMA 2a/b prodrug. Shown in red is the amount of Dox released. Shown in blue is the formation of Dox-DMI 1. Shown in green is background decomposition related to Dox-containing compounds. The legend for various compounds is shown in pH 7.4, see FIG. 24A.

The pH-dependence of drug release from Dox-DMA prodrug 2a/b was evaluated at rt by adjusting the solution pH value to 7.4, 7.0, 6.8, 6.5, 6.3, or 6.0 (FIG. 24A-24F). The overall trend is clear: as the pH became more acidic, Dox release accelerated dramatically. At pH 7.4, after 24 h, only about 20% of Dox was released while 35% of Dox-DMI 1 was present (a few percent of DMI was present at time 0) (FIG. 24A). At pH 7.0, Dox release reached 43% after 5 h, plateauing out at 67% after 24 h (FIG. 24B). At pH 6.8, about 43% of Dox was released after 4 h, and maximum drug release of 64% was reached after 15 h (FIG. 24C). For both pH 7.0 and 6.8, there was around 15% of DMI after 5 h, and this percentage did not increase afterwards. At pH 6.5, more than 60% of Dox was released after 2 h, reaching a plateau of 77% after 5 h; meanwhile, DMI was only present at less than 10% (FIG. 24D). At pH 6.3 and 6.0, about 75% of Dox was released after only 2 h and only a small amount of DMI (at most 10%) was present throughout (FIGS. 24E, 24F). As Dox release became more dominant, DMI formation was suppressed. The pH-low/pH-high ratio of drug release varied based on the specific time point. Pharmacokinetics modeling suggested that the therapeutic time window of Dox is in the first few hours. Therefore, drug release difference in the initial 1-6 hour would be the most meaningful parameter to follow.

FIG. 25A-24E. pH-dependent drug release from Dox-DMA-Glu 4a/b at rt in aq. phosphate buffer. Prodrug consumption (black), drug release (red), DMI formation (blue), and other decompositions (green) were followed by HPLC at pH 7.4 (25A), 7.1 (25B), 6.8 (25C), 6.5 (25D), or 6.2 (25E).

Drug release from Dox-DMA-Glu 4a/b was also examined at different pH values at rt. As expected, Dox release increased as the pH was lowered. Dox release will be compared at 1 h and at a longer time approaching maximum. At pH 7.4, after 1 h, Dox release was at 6%, reaching 41% after 10 h; meanwhile, formation of Dox-DMI-Glu 2 reached 23% after 10 h (12% of DMI was present at time 0) (FIG. 25A). At pH 7.1 and 6.8, after 1 h, 16% and 19% of Dox was released, respectively (FIG. 25B, 25C). Dox release reached the maxima of 55-60% after 10 h at both pH 7.1 and 6.8 (FIG. 25B, 25C). At pH 6.5, Dox release reached 21% at 1 h and 50% at 8 h (FIG. 25D). At pH 6.2, 41% of Dox was released after 1 h, plateauing ~70% after 4 h (FIG. 25E). At all pH values, often less than 10% of Dox-DMA-Glu 4a/b converted back to Dox-DMI-Glu 2 throughout all time periods followed (FIG. 25A-25E). DMI formation is not a significant factor in this case.

FIGS. 26A-26E. pH-dependent drug release from Dox-DMA-Cys 6a/b at rt in aq. phosphate buffer. Prodrug consumption (black), drug release (red), DMI formation (blue), and other decompositions (green) were tracked by HPLC at pH 7.4 (26A), 7.1 (26B), 6.8 (26C), 6.5 (26D), and 6.2 (26E).

Drug release from Dox-DMA-Cys 4a/b prodrug at rt also displayed ultra acid-sensitivity. After 3 h, Dox release reached ~5% at pH 7.4 and 7.1 (FIGS. 26A, 26B), 14% at pH 6.8 (FIG. 26C), and ~40% at pH 6.5 and 6.2 (FIG. 26D, 26E). At longer time points, more Dox was released at all pH values: 27% in 39 h at pH 7.4, 35% in 31 h at pH 7.1, 48% in 25 h at pH 6.8, and ~60% in 15 h at both pH 6.5 and 6.2. At higher pH values of 7.4 and 7.1, DMI formation outpaced drug release in the initial period of 1-6 h, from 5-7% at time 0 to ~20% in just a few hours. At pH 6.5 and 6.2, drug release was so fast that DMI formation was almost absent.

FIGS. 27A-27F. pH-selective drug release from DMA prodrugs at 37° C. Prodrug consumption (black), drug release (red), DMI formation (blue), and other decompositions (green) were tracked by HPLC at pH 7.4 (27A, 27C, 27E) and 6.5 (27B, 27D, 27F). Data regarding Dox-DMA 2a/b are shown in FIGS. 27A and 27B, Dox-DMA-Glu 4a/b in FIGS. 27C and 27D, and Dox-DMA-Cys 6a/b in FIGS. 27E and 27F.

Next, drug release from DMA prodrugs were investigated at 37° C. at pH 7.4 and 6.5. All three prodrugs released Dox quicker at 37° C. than rt, yet the pH-selectivity is maintained. After 2 h, Dox-DMA 2a/b released 79% of Dox at pH 6.5, compared to 33% at pH 7.4, giving a pH 6.5/7.4 ratio of 2.4 (FIG. 27A, 27B). A better ratio was observed for Dox-DMA-Glu 4a/b. After 2 h, Dox release from Dox-DMA-Glu 4a/b reached 49% at pH 6.5 and 14% at pH 7.4, resulting in a pH 6.5/7.4 ratio of 3.4 (FIG. 27C, 27D). Finally, Dox-DMA-Cys 6a/b displayed the largest difference, with 55% of Dox released after 2 h at pH 6.5 and 9% at pH 7.4, giving a pH 6.5/7.4 ratio of 6.1 (FIG. 27E, 27F).

FIG. 28A-28F. Drug release comparison of various DMA prodrugs at 37° C. The behavior of the three prodrugs are plotted side-by-side in this figure. Dox release at pH 7.4 (A) and 6.5 (28B) are shown in red. DMA consumption at pH 7.4 (28C) and 6.5 (28D) are shown in black. DMI formation at pH 7.4 (28E) and 6.5 (28F) are shown in blue. Round dots with dash-dot lines are the data relating to Dox-DMA 2a/b. Rhombuses with dotted lines are the data of Dox-DMA-Glu 4a/b. Squares with solid lines are the data regarding Dox-DMA-Cys 6a/b.

Alternatively, the same data of drug release at 37° C. were replotted to compare the prodrug behaviors side-by-side (FIGS. 28A-28F). The rate of background Dox release at pH 7.4 is considerably different among the three prodrugs, with Dox-DMA 2a/b the fastest (which is undesirable) and Dox-DMA-Cys 6a/b the slowest (FIG. 28A). This trend is inversely reflected in the disappearance of DMA prodrugs at pH 7.4 (FIG. 28C). At pH 7.4 after 6 h, about 80% of Dox-DMA 2a/b was consumed, compared to ~60% for Dox-DMA-Glu 4a/b and 51% for Dox-DMA-Cys 6a/b (the most stable, FIG. 28C). Interestingly, the rate of Dox release at pH 6.5 is roughly the same among the three prodrugs in the first hour, with more drug released by Dox-DMA 2a/b than the other two by 2 h (FIG. 28B). Dox-DMA-Glu 4a/b and Dox-DMA-Cys 6a/b released similar amounts of Dox at pH 6.5, even though Dox-DMA-Cys 6a/b is more stable than Dox-DMA-Glu 4a/b at pH 7.4 (FIG. 28A, 28B). More DMA prodrugs converted to their corresponding DMI forms at pH 7.4 than 6.5 (compare FIG. 28E vs. 28F). At pH 7.4 after 10 h, about 13% Dox-DMI 1 was formed, compared to 26% for Dox-DMI-Glu 3 and Dox-DMI-Cys 5 (FIG. 28E). At pH 6.5, in all cases only a few percent of DMI was formed. These trends reflect the competing reaction pathways of 'switch-on' (Dox release) vs. 'switch-off' (DMI formation). When Dox is rapidly released at pH 6.5, the DMA prodrug did not have enough time to form DM. At pH 7.4, faster DMI formation (Dox-DMI-Cys 5>Dox-DMI-Glu 3>Dox-DMI 1 in FIG. 28E) correlated with slower drug release (Dox-DMA-Cys 6a/b<Dox-DMA-Glu 4a/b<Dox-DMA 2a/b in FIG. 28A). In this way, DMI formation may help suppress background drug release.

Evaluations of DMA prodrugs of Dox in cancer and kidney cells. Due to rapid growth, many cancerous tumors have pHe in the range of 6.5-6.9 (average 6.7), compared with pHe of 7.4 in healthy tissues. Such tumor acidosis can impede chemotherapy by decreasing the membrane permeability of amine drugs, in particular, anthracyclines such as Dox. Thus, Dox is more cytotoxic at pHe of 7.4 (as in healthy tissues) than 6.7 (as in tumor). To turn tumor acidosis against cancer, ultra acid-sensitive, small molecule prodrugs were developed to selectively release Dox in response to acidic tumor pHe. To evaluate whether DMA prodrugs 2a/b, 4a/b, and 6a/b can inhibit the growth of cancer cells in a pH-dependent fashion, these compounds were tested at various pH values with ES2 ovarian cancer cells. The reported pH values were measured before and after the experiment. To simulate cytotoxicity in off-target healthy tissues, these DMA prodrugs were also tested on noncancerous kidney epithelial HK2 cells.

Figure 29A:
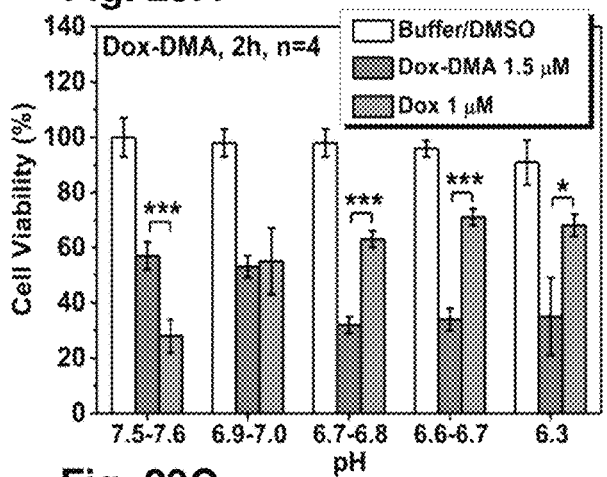
FIGS. 29A-29E show effects of pH, dose and treatment time on the pH-sensitive cytotoxicity of Dox-DMA 2a/b. The prodrug was evaluated in antiproliferation assays with ES2 ovarian cancer cells or noncancerous HK2 kidney cells. (29A) The effect of pH on the cytotoxicity of Dox-DMA 2a/b and free Dox. ES2 cells were treated for 2 h with Dox-DMA 2a/b (blue bars), free Dox (orange bars), or vehicle (phosphate buffer with small amount of DMSO, white bars) at various pH values between pH 6.3 and 7.6. (29B) Cytotoxicity of Dox-DMA 2a/b and free Dox on noncancerous kidney epithelial HK2 cells at pH 7.4. HK2 cells were treated with Dox-DMA 2a/b (blue) or free Dox (orange) at concentrations ranging from 3 nM to 30 $\mu$M. (29C) The effect of dose on the pH-dependent cytotoxicity of Dox-DMA 2a/b. ES2 cells were treated for 2 h with 0.5, 1, 2 or 4 $\mu$M of Dox-DMA 2a/b at pH 6.6-6.9 (blue) or pH 7.2-7.7 (orange). (29D) The anhydride byproduct 7 of drug release is not cytotoxic. ES2 cells were treated with 2, 20 or 200 $\mu$M of 7 at pH 6.7-6.8 (blue) or 7.5-7.6 (orange) for 2 h. (29E) The effect of treatment duration on the pH-dependent cytotoxicity of Dox-DMA 2a/b. ES2 cells were treated with Dox-DMA 2a/b (2 $\mu$M), free Dox (1 $\mu$M), or vehicle for 1, 2 or 4 h at pH 6.8 (blue) or pH 7.6-7.7 (orange). All pH values reported were based on measurements done before and after each treatment. All experiments were carried out in 96-well plates. After treatment, cells were grown for a few days before the number of live cells per well was counted using the MTS assay. Data shown represent the average ±standard deviation (SD) (n=6 except for FIG. 29A where n=4). Statistical significances of the difference between the chosen data sets were evaluated using unpaired, two-tailed Student's test (*: P<0.05, : P<0.01, *: P<0.001).

Prodrug Dox-DMA 2a/b was first evaluated in a pH-scan experiment (FIG. 29A). ES2 cancer cells were treated with 1.5 µM of Dox-DMA 2a/b, 1 µM of free Dox (a positive control), or vehicle (aq. phosphate buffer with a small amount of DMSO) for 2 h at pH 7.5, 6.9, 6.7, 6.6 or 6.3. The vehicle negative control demonstrates that the effect of pH (within this range) on cell growth is minimal, i.e. cell viability at pH 6.3 is at ~90% level of that at pH 7.5. The lower pH did not kill cells to any significant extent. The overall trend is as expected, the free Dox is more cytotoxic at higher pH (28% viability at pH 7.5 vs. ~60-70% at pH 6.7, compared to vehicle at pH 7.5 as the 100%), while the prodrug is the opposite— more cytotoxic at lower pH (57% viability at pH 7.5 vs. 32% at pH 6.7). Especially interesting is the data that Dox-DMA 2a/b reached maximum cytotoxicity at pH 6.7. The potency was maintained at lower pH values but not improved. This level of cytotoxicity (~32% viability), achieved with 1.5 µM of Dox-DMA 2a/b at pH 6.6-6.8, is higher than that of 1 µM of free Dox at the same pH (60-70% viability), which means that almost all of the prodrugs converted to free Dox within 2 h, consistent with results from HPLC assays (FIGS. 28A-28F).

Figure 29B:
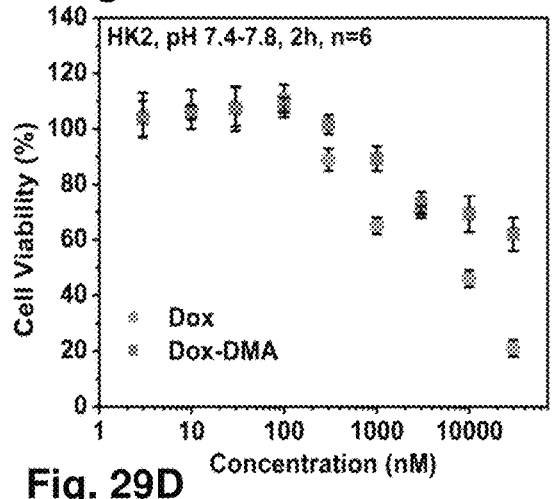
Figure 29C:
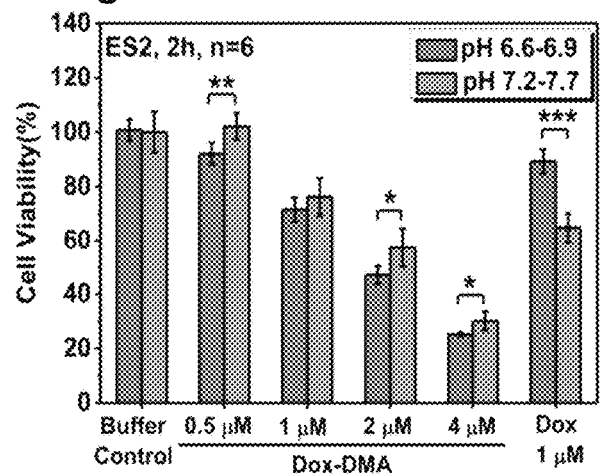

The effect of dose on prodrug 2a/b behavior was examined in FIG. 29C. As expected, higher dose killed ES2 cells more efficiently. After 1 µM treatment, 72% and 76% cells were alive at pH 6.7 and 7.4, compared to 25% (at pH 6.7) and 30% (at pH 7.4) after 4 µM treatment, respectively (FIG. 29C). More importantly, at 2 h treatment time, the proficiency of cytotoxicity pH-profile reversal (in prodrug vs. free Dox) seems to be better at 2 µM than either high (4 µM) or lower (1 µM) concentrations. The desired pH-selective cytotoxicity is quite sensitive to dose. If the concentration is too high, too much drug is release (and too many cells die) at pH 7.4.

FIGS. 29A-29E. Effects of pH, dose and treatment time on the pH-sensitive cytotoxicity of Dox-DMA 2a/b. The prodrug was evaluated in antiproliferation assays with ES2 ovarian cancer cells or noncancerous HK2 kidney cells. (29A) The effect of pH on the cytotoxicity of Dox-DMA 2a/b and free Dox. ES2 cells were treated for 2 h with Dox-DMA 2a/b (blue bars), free Dox (orange bars), or vehicle (phosphate buffer with small amount of DMSO, white bars) at various pH values between pH 6.3 and 7.6. (29B) Cytotoxicity of Dox-DMA 2a/b and free Dox on noncancerous kidney epithelial HK2 cells at pH 7.4. HK2 cells were treated with Dox-DMA 2a/b (blue) or free Dox (orange) at concentrations ranging from 3 nM to 30 µM. (29C) The effect of dose on the pH-dependent cytotoxicity of Dox-DMA 2a/b. ES2 cells were treated for 2 h with 0.5, 1, 2 or 4 µM of Dox-DMA 2a/b at pH 6.6-6.9 (blue) or pH 7.2-7.7 (orange). (29D) The anhydride byproduct 7 of drug release is not cytotoxic. ES2 cells were treated with 2, 20 or 200 µM of 7 at pH 6.7-6.8 (blue) or 7.5-7.6 (orange) for 2 h. (29E) The effect of treatment duration on the pH-dependent cytotoxicity of Dox-DMA 2a/b. ES2 cells were treated with Dox-DMA 2a/b (2 µM), free Dox (1 µM), or vehicle for 1, 2 or 4 h at pH 6.8 (blue) or pH 7.6-7.7 (orange). All pH values reported were based on measurements done before and after each treatment. All experiments were carried out in 96-well plates. After treatment, cells were grown for a few days before the number of live cells per well was counted using the MTS assay. Data shown represent the average ±standard deviation (SD) (n=6 except for FIG. 29A where n=4). Statistical significances of the difference between the chosen data sets were evaluated using unpaired, two-tailed Student's test (*: P<0.05, : P<0.01, *: P<0.001).

Figure 29D:
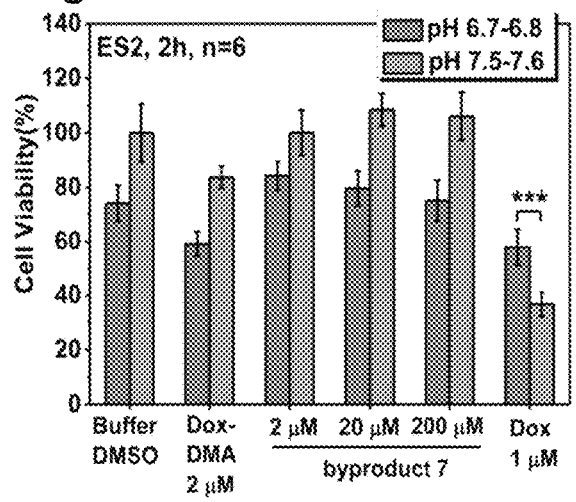
Figure 29E:
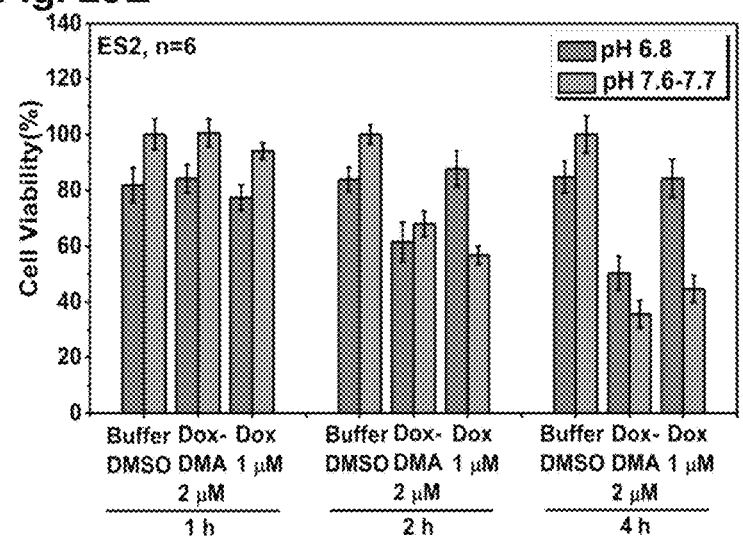

The treatment time also has an effect on the pH-sensitivity of Dox-DMA (FIG. 29E). When the prodrug vs. free Dox concentrations are fixed at 2 µM for 2a/b and 1 µM for Dox, 2 h treatment showed more of the desired pH-profile than 4 h treatment. After 2 h, the prodrug is more toxic than free drug at pH 6.8 while less toxic than free drug at pH 7.6; after 4 h, the prodrug is more toxic than free drug at both low and high pH.

Effects of prodrug Dox-DMA 2a/b on noncancerous HK2 kidney cells were also examined (in conjunction with free Dox). Data shown in FIG. 29B indicate that prodrug 2a/b is less cytotoxic than free Dox towards HK2 cells at pH 7.4 (e.g., ~60% viability for 30 µM of Dox-DMA 7a/b, compared to 21% viability with 30 µM of Dox). These noncancerous HK2 cells are less sensitive to Dox than ES2 cancer cells in general.

To find out if the drug release byproduct 7 is toxic, ES2 cells were treated with 2 µM, 20 µM, or 200 µM of anhydride 7 (FIG. 29D). At both pH 6.7 and 7.5, no difference was observed between vehicle and anhydride 7, even at 200 µM concentration; thus, this byproduct is harmless to cells. MS data suggest that such type of anhydride can be slowly hydrolyzed to the di-carboxylate at pH~7-8.

FIGS. 30A-30E. Effects of pH, dose and treatment time on the pH-sensitive cytotoxicity of Dox-DMA-Glu 4a/b. (30A) The effect of pH on the cytotoxicity of Dox-DMA-Glu 4a/b and free Dox. ES2 ovarian cancer cells were treated for 3 h with 3 µM of Dox-DMA-Glu 4a/b (blue bars), 1 µM of free Dox (orange bars), or vehicle (phosphate buffer with small amount of DMSO, white bars) at various pH values between pH 6.1 and 7.4. (30B) Cytotoxicity of Dox-DMA-Glu 4a/b and free Dox on noncancerous kidney epithelial HK2 cells at pH 7.4. HK2 cells were treated with Dox-DMA-Glu 4a/b (blue) or free Dox (orange) at concentrations ranging from 3 nM to 30 µM. (30C) The effect of dose on the pH-dependent cytotoxicity of prodrug 4a/b. ES2 cells were treated for 2.5 h with 1, 2, 4 or 8 µM of Dox-DMA-Glu 4a/b at pH 6.5-6.7 (blue) or pH 7.2-7.5 (orange). (30D) The anhydride byproduct 10 of drug release is not cytotoxic. ES2 cells were treated with 3, 30 or 300 µM of 10 at pH 6.5-6.6 (blue) or 7.4-7.5 (orange) for 3 h. (30E) The effect of treatment duration on the pH-dependent cytotoxicity of Dox-DMA-Glu 4a/b. ES2 cells were treated with Dox-DMA-Glu 4a/b (2 µM), free Dox (0.5 µM), or vehicle for 1, 2, 4 or 8 h at pH 6.5-6.6 (blue) or pH 7.5-7.7 (orange). All pH values reported were based on measurements done before and after each treatment. All experiments were carried out in 96-well plates. After treatment, cells were grown for a few days before the number of live cells per well was counted using the MTS assay. Data shown represent the average ±SD (n=6 except for FIG. 30A where n=4 and FIG. 30D where n=5). Statistical significances of the difference between the chosen data sets were evaluated using unpaired, two-tailed Student's test (*: P<0.05, : P<0.01, *: P<0.001).

Next, prodrug Dox-DMA-Glu 4a/b was evaluated in antiproliferation assays with ES2 ovarian cancer cells (or noncancerous HK2 cells) (FIGS. 31A-31D). The layout and setup of the Dox-DMA-Glu 4a/b data and experiments in FIGS. 31A-31D are similar to those for prodrug 2a/b in FIG. 42, which have been discussed in detail previously.

The pH scan experiment (ES2 cells, 3 µM of 4a/b, 3 h) revealed that the prodrug 4a/b is more cytotoxic at lower pH: 85% viability at pH 7.4 vs. 40% at pH 6.6 (FIG. 30A). More significantly, near-maximum level of cytotoxicity could be reached at pH 6.6. Compared to the pH-scan experiment of Dox-DMA 2a/b (FIG. 29A), cells were treated at a higher concentration of 4a/b (3 µM vs. 1.5 µM) for a longer time (3 h vs. 2 h), on account of its slower release rate. The higher concentration of 4a/b in itself is not necessarily undesirable as 3 µM of 4a/b is still much less cytotoxic than 1 µM of Dox at pH 7.4 (FIG. 30A).

In FIGS. 30C and 30E, dose scan and time scan experiments again confirmed that only at certain concentration (4 µM) and treatment time (2 h), the desired pH-profile in cytotoxicity, i.e. the prodrug being more cytotoxic than free Dox at pH 6.5-6.7 and less cytotoxic than free Dox at pH 7.4, could be achieved for prodrug 4a/b. At higher concentration or longer treatment time, too much Dox is released, e.g., after 2 h of treatment, there was ~20% less viable cells at pH 6.5 than 7.5 while at 4 h, no difference was observed (FIG. 30E).

Towards noncancerous HK2 cells, free Dox is more cytotoxic than prodrug 4a/b (FIG. 30B): 1 µM of Dox killed 20% cells while 1 µM of Dox-DMA-Glu 4a/b had no effect, and there were ~70% viable cells after treatment with 30 µM of 4a/b, but only 31% viable cells after treatment with 30 µM of Dox. Furthermore, the anhydride, drug release byproduct 10 is not cytotoxic up to 30 µM concentration (FIG. 30D).

FIGS. 31A-31E. Effects of pH, dose and treatment time on the pH-sensitive cytotoxicity of Dox-DMA-Cys 6a/b. (31A) The effect of pH on the cytotoxicity of Dox-DMA-Cys 6a/b and free Dox. ES2 ovarian cancer cells were treated for 2 h with 2 µM of Dox-DMA-Cys 6a/b (blue bars), 1 µM of free Dox (orange bars), or vehicle (phosphate buffer with small amount of DMSO, white bars) at various pH values between pH 6.1 and 7.5. (31B) Cytotoxicity of Dox-DMA-Cys 6a/b and free Dox on noncancerous kidney epithelial HK2 cells at pH 7.4. HK2 cells were treated with Dox-DMA-Cys 6a/b (blue) or free Dox (orange) at concentrations ranging from 3 nM to 30 µM. (31C) The effect of dose on the pH-dependent cytotoxicity of prodrug 6a/b. ES2 cells were treated for 3 h with 1, 2, 4 or 8 µM of Dox-DMA-Cys 6a/b at pH 6.4-6.5 (blue) or pH 7.3-7.4 (orange). (31D) The anhydride byproduct 12 of drug release is not cytotoxic. ES2 cells were treated with 2, 20 or 200 µM of 12 at pH 6.7 (blue) or 7.4-7.5 (orange) for 2 h. (31E) The effect of treatment duration on the pH-dependent cytotoxicity of Dox-DMA-Cys 6a/b. ES2 cells were treated with Dox-DMA-Cys 6a/b (2 µM), free Dox (0.5 µM), or vehicle for 1, 2, 4 or 8 h at pH 6.7 (blue) or pH 7.4-7.6 (orange). All pH values reported were based on measurements done before and after each treatment. All experiments were carried out in 96-well plates. After treatment, cells were grown for a few days before the number of live cells per well was counted using the MTS assay. Error bars reflect ±SD (n=6 except for FIG. 31A where n=4). Statistical significances of the difference between the chosen data sets were evaluated using unpaired, two-tailed Student's test (*: $P<0.05$, : $P<0.01$, *: $P<0.001$).

The disulfide containing prodrug, Dox-DMA-Cys 6a/b, was next examined in antiproliferation assays with ES2 and HK2 cells as described previously (FIGS. 31A-31E). Among the three prodrugs reported here, Dox-DMA-Cys 6a/b is the most similar to the previously reported prodrug Dox-DMA-GSH. The pH scan (ES2 cells, 2 µM of 6a/b, 2 h) confirmed that the prodrug is significantly more cytotoxic at pH 6.5-6.8 (~40% viability) than at pH 7.5 (~90% viability), while the free Dox is the opposite (~40-60% viability at pH 6.5-6.8 vs. ~20% viability at pH 7.5) (FIG. 31A). It appears that prodrug 6a/b reached even higher cytotoxicity (only 20% cells viable) at pH 6.1; however, in this particular experiment, the low pH in itself may have killed some cells, as seen in the lower bar for the vehicle buffer control at pH 6.1 (FIG. 31A). In the dose scan data shown in FIG. 31C, prodrug 6a/b displayed robust pH-dependent cytotoxicity in the 1-8 µM concentration range. The best result was achieved at 4 µM of 6a/b, with both pH-profile reversal and potency present when compared to Dox. In the 2-4 h range, Dox-DMA-Cys 6a/b was not only more cytotoxic at pH 6.7 than 7.4, but also more cytotoxic than Dox at pH 6.7 while less cytotoxic than Dox at pH 7.4 (FIG. 31E). Prodrug 6a/b is less cytotoxic than free Dox towards noncancerous HK2 cells at pH 7.4 (FIG. 31B). For instance, 30 µM of Dox killed >80% of the cells while 30 µM of 6a/b killed only 30% of the cells (FIG. 31B). The drug release byproduct 12 did not show any cytotoxicity even at 200 µM concentration (FIG. 31D).

FIGS. 32A-32D. Side-by-side comparison of prodrugs 2a/b, 4a/b and 6a/b. In FIGS. 32A to 32C, ES2 ovarian cancer cells were treated for 2 h with 2 µM of Dox-DMA 2a/b, Dox-DMA-Glu 4a/b and Dox-DMA-Cys 6a/b at pH 6.4 vs 7.2 (32A), pH 6.6 vs 7.4 (32B), or pH 6.8 vs 7.3 (32C). In FIG. 32D, ES2 cells were treated with 4 µM of prodrugs at pH 6.8 vs 7.5. The positive control was 1 µM of Dox and the negative control was the vehicle (buffer with a trace amount of DMSO). Cell proliferation was determined by MTS assay after 3 days of incubation. The pH ranges reported come from measurements made before and after the experiment. Error bars reflect ±SD. Statistical significances of the difference between the chosen data sets were evaluated using unpaired, two-tailed Student's test (*: $P<0.05$, : $P<0.01$, *: $P<0.001$).

(Among the three prodrugs, data in FIGS. 28-30 were obtained under slightly different conditions. Behavior of cells (e.g., sensitivity to Dox, growth rate) also varied to a small extent from week to week.) To gain information about the relative performance of the three prodrugs, it was necessary to assess them in the same experiment on one 96-well plate. Results of these head-to-head comparisons are shown in FIGS. 31A-32D. A limited pH scan was conducted at 2 µM dose of prodrug vs. 1 µM of Dox with 2 h treatments: ES2 cells were incubated with Dox-DMA 2a/b, Dox-DMA-Glu 4a/b, Dox-DMA-Cys 6a/b and free Dox at pH 7.2-7.4 and pH 6.4 (FIG. 32A), 6.6 (FIG. 32B), or 6.8 (FIG. 32C).

In all cases, the prodrugs were more cytotoxic at lower pH, which validate the overall design. Furthermore, in FIG. 32A, all three prodrugs were also more potent than free Dox at pH 6.4 yet less cytotoxic than free Dox at pH 7.2-7.3. As the lower pH increased to pH 6.6 in FIG. 32B and pH 6.8 in FIG. 32C, the potency of Dox-DMA-Glu 4a/b and Dox-DMA-Cys 6a/b gradually declined, while Dox-DMA 2a/b remained effective throughout.

These results would give the impression that Dox-DMA 2a/b may be the most promising prodrug among the three. However, when the dose was increased to 4 µM of prodrug, only Dox-DMA-Cys 6a/b demonstrated the desired cytotoxicity pH-profile and potency (FIG. 29D). Thus, which of the three prodrugs is most effective depends on the detailed conditions employed (e.g., dose, treatment time). Although the range of experimental conditions used in this study (i.e. 1-8 µM concentration, 1-8 h treatment time) are modeled after tumor exposure to Dox in cancer patients, whether these parameters are applicable to prodrug is unknown. Tumor exposure to prodrug (concentration of prodrug in tumor over time) would be dictated by pharmacokinetics of the prodrug, which could only be evaluated in animal studies in the future.

Confocal microscopy studies of free Dox, DMA prodrugs 2a/b, 4a/b, 6a/b and DMI 1, 3, 5. Dox can serve as a biocompatible fluorophore, which provides an opportunity to gain further insights about DMA prodrug—cell interactions through microscopy. Specific goals of the following experiments are (a) to seek direct imaging evidence of pH-selective Dox release (by comparing Dox fluorescence intensity at different pH values), and (b) to gain information about whether the DMA prodrugs are membrane-impermeable.

The strategy to approach goal (b) are indirect and requires further explanation. The overarching aim is to build prodrugs that release Dox in response to acidic extracellular pH in the tumor. To contain the DMA prodrug in the extracellular compartment, a charged polar modulator moiety is incorporated into the structure in an attempt to make the prodrug membrane-impermeable (FIG. 42). It is important to test if the polar modulator is fulfilling this role. When visualized through the Dox channel (excitation: 488 nm, emission: 560-630 nm), the signal could come from Dox and/or any Dox-containing compounds that entered cells, including DMA prodrug and DMI byproduct. The DMA prodrug is unstable and cannot be imaged directly. During the 1 h treatment period, the DMA prodrug would cleave to release Dox or cyclize to the DMI byproduct. To clarify this situation, for each DMA prodrug, images were also acquired for the DMI form, because it is more stable than the DMA prodrug at pH 6.7-7.7. From previous studies, it is known that the DMI form has lower cytotoxicity (the desired therapeutic effect) than the DMA prodrug. Upon cyclization from DMA to DMI, one negative charge is removed (FIG. 42). It is reasonable to expect the DMI byproduct to be less polar and more membrane-permeable than the corresponding DMA prodrug. Thus, the DMI-cell interactions can infer on whether the DMA prodrug is membrane impermeable, as in 'if the DMI form is membrane impermeable, the DMA form should be even more membrane impermeable'.

ES2 cells were treated at pH 6.7 or 7.7 for 1 h with 8 μM of a DMA prodrug, 8 μM of a DMI byproduct, or 4 μM of free Dox. Afterwards, the treatment solution was removed; the nuclei of the cells were labeled with staining dye Hoechst 33342; and then images were taken on a scanning confocal microscope.

Imaging results for free Dox treatments are shown in FIG. 33. There is accumulation of Dox inside the cells at both pH 6.7 and 7.7. More Dox fluorescence signals were observed at pH 7.7 than 6.7, which is consistent with the data from antiproliferation assays that Dox is more cytotoxicity at pH 7.7 than 6.7.

FIG. 33. Confocal microscopy images of free Dox at pH 6.7 and 7.7. ES2 cells were treated with 4 μM of Dox at pH 6.7 or 7.7 for 1 hour; the treatment solution was removed; then the nuclei of ES2 cells were labeled with Hoechst 33342 (blue) for 10 min; images were taken immediately afterwards with a Leica TCS SP5 Confocal Laser Scanning Microscope with a 63× oil lens. The scale bars represent 25 m. Red: fluorescence of Dox (or Dox-containing compounds), blue: nuclei.

For all three DMA prodrugs, significantly more Dox fluorescence signals were observed at pH 6.7 than 7.7 (compare the first two rows of FIGS. 34-36), a reversal of free Dox behavior (FIG. 33). This trend is consistent with the knowledge that prodrugs 2a/b, 4a/b and 6a/b release more Dox (FIGS. 24-28) and are more cytotoxic at pH 6.7 than 7.6 (FIGS. 29-32). The DMA prodrugs would be mostly stable at pH 7.7 (as shown in FIGS. 28A-28F, 10-15% conversion to the DMI form and 10-20% drug release would be expected in 1 h). The much weaker Dox signal at pH 7.7 directly support the notion that DMA prodrugs 2a/b, 4a/b and 6a/b do not enter cells (FIGS. 34-36).

Figure 34:
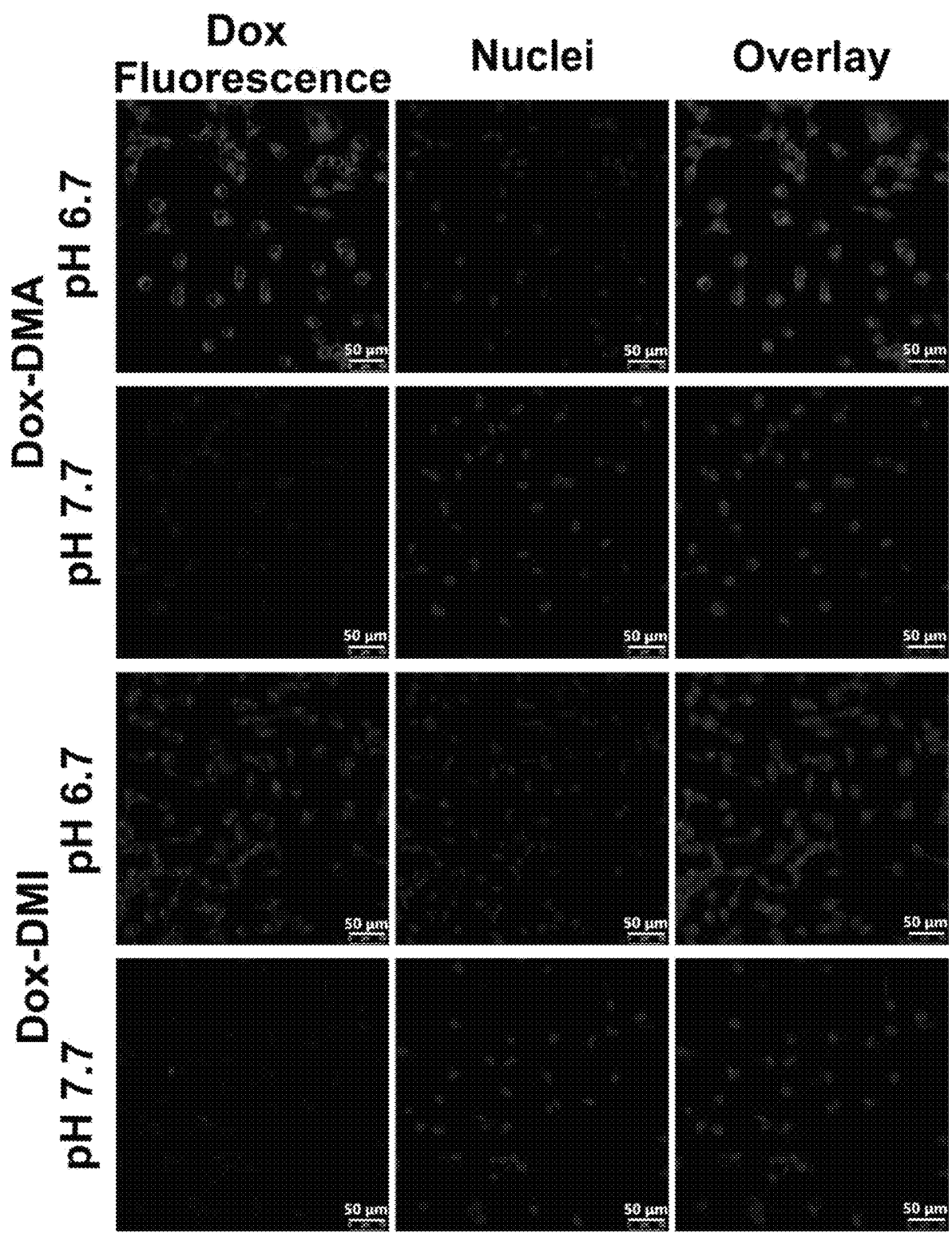
FIG. 34 shows confocal microscope images of Dox-DMA 2a/b and Dox-DMI 1. ES2 cells were treated with 8 μM of Dox-DMA 2a/b or Dox-DMI 1 at pH 6.7 or 7.7 for 1 hour. After removal of treatment solution, the nuclei of ES2 cells were labeled with Hoechst 33342 (blue) for 10 min. Images were taken afterwards with a Leica TCS SP5 Confocal Laser Scanning Microscope with a 40× oil lens. The scale bars represent 50 m. Red: Dox channel, blue: nuclei staining.
Figure 35:
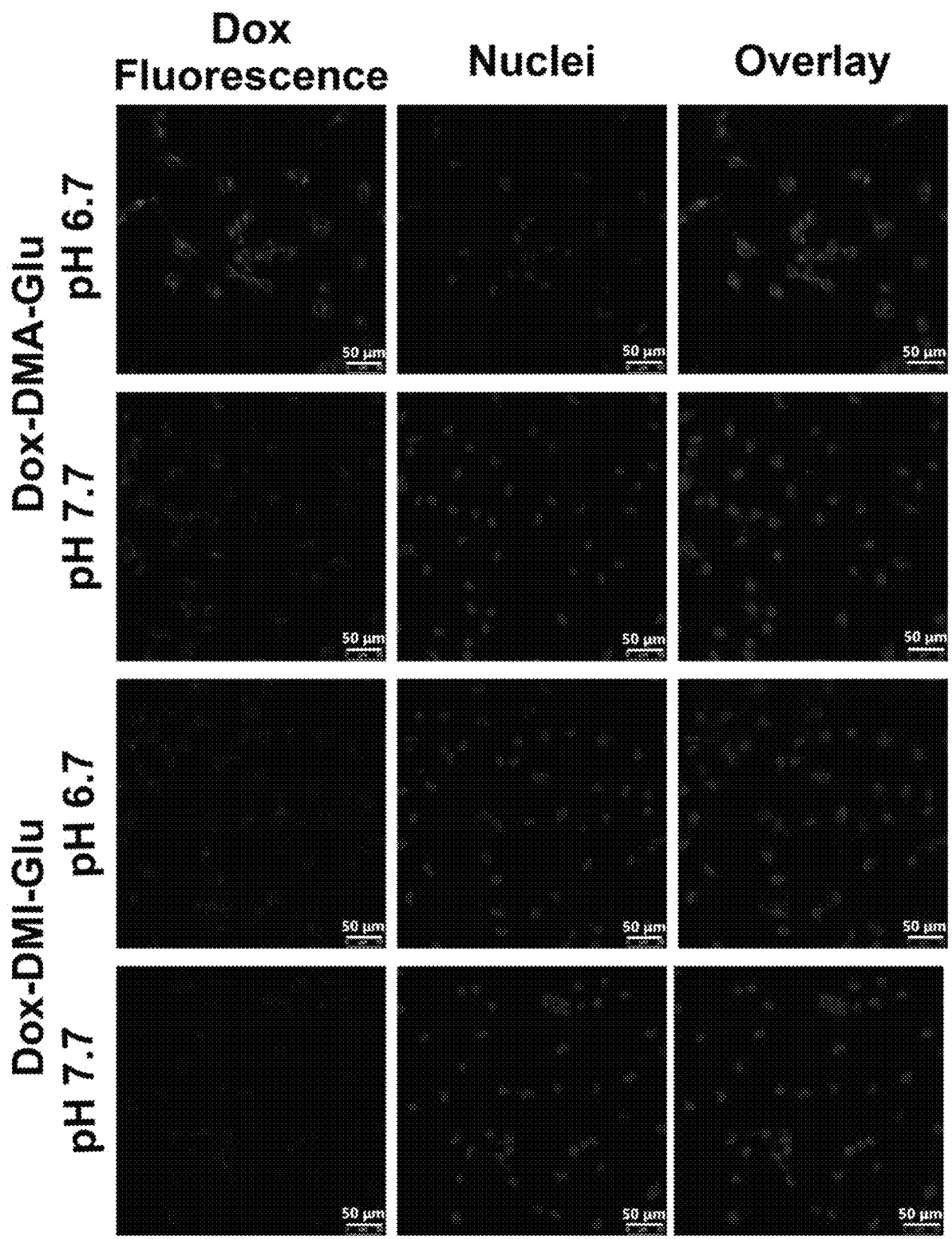
FIG. 35 shows confocal microscope images of Dox-DMA-Glu 4a/b and Dox-DMI-Glu 3. ES2 cells were treated with 8 μM of Dox-DMA-Glu 4a/b or Dox-DMI-Glu 3 at pH 6.7 or 7.7 for 1 hour. After removal of treatment solution, the nuclei of ES2 cells were labeled with Hoechst 33342 (blue) for 10 min. Images were taken afterwards with a Leica TCS SP5 Confocal Laser Scanning Microscope with a 40× oil lens. The scale bars represent 50 m. Red: Dox channel, blue: nuclei staining.
Figure 36:
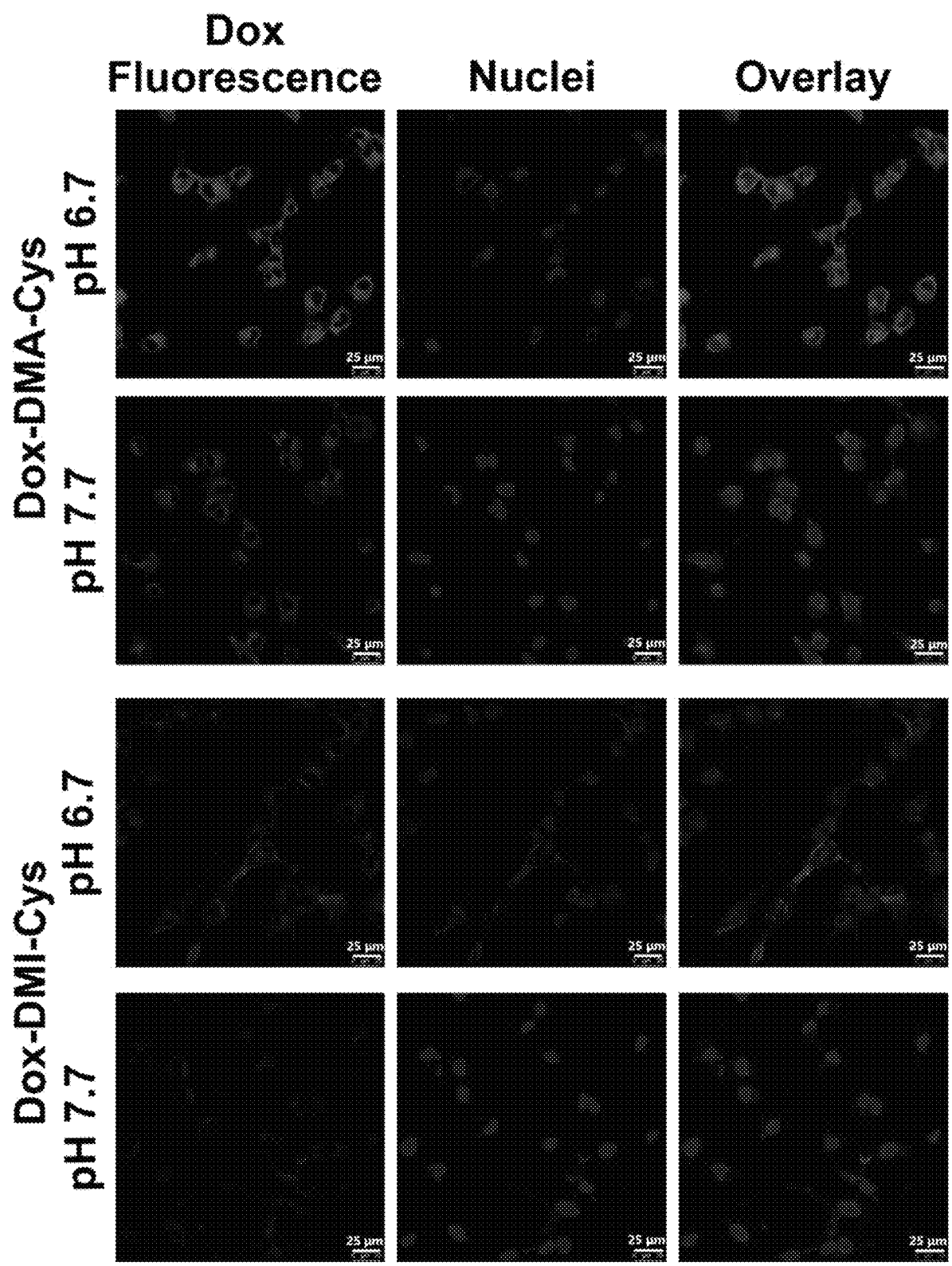
FIG. 36 shows confocal microscope images of Dox-DMA-Cys 6a/b and Dox-DMI-Cys 5. ES2 cells were treated with 8 μM of Dox-DMA-Cys 6a/b or Dox-DMI-Cys 5 at pH 6.7 or 7.7 for 1 hour. After removal of treatment solution, the nuclei of ES2 cells were labeled with Hoechst 33342 (blue) for 10 min. Images were taken afterwards with a Leica TCS SP5 Confocal Laser Scanning Microscope with a 63× oil lens. The scale bars represent 25 m. Red: Dox channel, blue: nuclei staining.

Comparing the Dox signal of the DMA prodrug to their corresponding DMI byproduct, in all three cases, the DMI byproduct had much less signal regardless of pH (FIGS. 34-36). These imaging data further support the conclusions that (a) DMI byproducts 1, 3, and 5, and by inference, the DMA prodrugs 2a/b, 4a/b and 6a/b, are largely membrane-impermeable, (b) the signals seen for DMA prodrugs at pH 6.7 are mostly from released free Dox, and (c) DMI byproducts are much less toxic than DMA prodrugs.

FIG. 34. Confocal microscope images of Dox-DMA 2a/b and Dox-DMI 1. ES2 cells were treated with 8 μM of Dox-DMA 2a/b or Dox-DMI 1 at pH 6.7 or 7.7 for 1 hour. After removal of treatment solution, the nuclei of ES2 cells were labeled with Hoechst 33342 (blue) for 10 min. Images were taken afterwards with a Leica TCS SP5 Confocal Laser Scanning Microscope with a 40× oil lens. The scale bars represent 50 μm. Red: Dox channel, blue: nuclei staining.

FIG. 35. Confocal microscope images of Dox-DMA-Glu 4a/b and Dox-DMI-Glu 3. ES2 cells were treated with 8 μM of Dox-DMA-Glu 4a/b or Dox-DMI-Glu 3 at pH 6.7 or 7.7 for 1 hour. After removal of treatment solution, the nuclei of ES2 cells were labeled with Hoechst 33342 (blue) for 10 min. Images were taken afterwards with a Leica TCS SP5 Confocal Laser Scanning Microscope with a 40× oil lens. The scale bars represent 50 m. Red: Dox channel, blue: nuclei staining.

FIG. 36. Confocal microscope images of Dox-DMA-Cys 6a/b and Dox-DMI-Cys 5. ES2 cells were treated with 8 μM of Dox-DMA-Cys 6a/b or Dox-DMI-Cys 5 at pH 6.7 or 7.7 for 1 hour. After removal of treatment solution, the nuclei of ES2 cells were labeled with Hoechst 33342 (blue) for 10 min. Images were taken afterwards with a Leica TCS SP5 Confocal Laser Scanning Microscope with a 63× oil lens. The scale bars represent 25 m. Red: Dox channel, blue: nuclei staining.

Among the DMI byproducts, more signals were seen for Dox-DMI 1 (FIG. 34) than Dox-DMI-Cys 5 (FIG. 36) and Dox-DMI-Glu 3 (FIG. 35). The Dox-DMI 1 signal levels are also higher at pH 6.7 than 7.7. These patterns are consistent with the properties of the different polar modulators. Perhaps the carboxylate group of Dox-DMI 1 (bearing its only negative charge, see FIG. 42) was more easily protonated to the neutral carboxylic acid form at pH 6.7 than 7.7. Accordingly, small amounts of neutral Dox-DMI 1 could go through cell membrane and display fluorescence signal in cells.

Interestingly, the distribution pattern of Dox fluorescence within cells are also different between the free Dox experiment (FIG. 33) and the DMA prodrug experiments (FIGS. 34-36). For free drug treatment in FIG. 33, most of the Dox signals were found within the nuclei, which is expected as Dox binds to DNA. For DMA prodrug treatments in FIGS. 34-36, Dox channel signals were mainly located outside of the nuclei. Such discrepancy might be attributable to differences in the kinetics of cellular entry of Dox: In the free drug experiments, 4 μM of Dox was present all at once even at time 0, while in the DMA prodrug dishes, free Dox concentration was built up gradually over time during the 1 h treatment period. Another factor or an alternative explanation might be the following: The fluorescence intensity of Dox is known to be much lower when Dox is bound to DNA (the fluorescence is quenched); thus, the population of Dox not bound to DNA may overshadow the population bound to DNA.

CONCLUSIONS

As a prominent and representative anthracycline chemodrug, Dox is commonly used in the treatments of sarcomas, childhood solid tumors, various carcinomas (breast, ovarian, bladder, gastric, lung, liver and kidney carcinomas) and other malignancies. Unfortunately, Dox and related anthracyclines cause cumulative, irreversible myocardial damage which limits their therapeutic dosages. DMA-type Dox prodrugs may be considered as improved versions of Dox, designed to improve the therapeutic window through pH-selective drug release when treating acidic solid tumors.

pH-sensitive drug release is accomplished through a three-state switch DMA linker: (1) cleaved—the 'on' state, (2) not cleaved—the 'temporarily off' prodrug state, and (3) the cyclized DMI state that is more 'permanently off'. The validation of such behavior for this class of Dox prodrugs are presented here, drawing on evidence gathered from HPLC cleavage tests, antiproliferation assays, and imaging with live cells, all carried out at various pH values.

These DMA-based prodrugs aim to improve the safety profile of chemo-drug by suppressing drug exposure at healthy tissues while preferentially releasing free drug at the tumors. This approach is also applicable to other chemo-drugs to help them reach to their therapeutic potentials by reducing side effects.

1. Chemicals for Synthesis (General Information).

Dimethylformamide (DMF), triethylamine (TEA), trifluoroacetic acid (TFA), and 2-aminoethanethiol hydrochloride (98% pure) were purchased from Acros Organics; triethyl-2-phosphonopropionate (98% pure), sodium hydride (57-63% dispersion in mineral oil, moist powder), pyridyl disulfide (98% pure), dimethylsulfoxide (DMSO), anhydrous acetonitrile, 1,8-diazabicyclo[5,4,0]undec-7-ene (DBU, 99% pure), 4-dimethylaminopyridine (DMAP, 99% pure), and oxalyl chloride (98% pure) from Alfa Aesar; dimethyl-2-oxo-glutarate (95% pure) from TCI America; (L)-cysteine.HCl (98%) from Sigma-Aldrich; tetrahydrofuran (THF), ethyl ether, anhydrous magnesium sulfate, ethyl acetate, sodium hydroxide, methanol, pyridine from Fisher Scientific; chloroform-d, $D_2O$, and dimethyl sulfoxide-d6 from Cambridge Isotope Laboratories (CIL); doxorubicin (Dox) hydrochloride salt from LC Laboratories; hexanes from BDH; ethanol from Pharmaco-APPER; dichloromethane from Macron Fine Chemicals/Avantor Performance Materials; L-glutamic acid di-tert-butyl ester hydrochloride from CHEM-IMPEX INT'L INC; acetic acid, sodium phosphate (dibasic and monobasic) from JT Baker; SiliaFlash P60 silica gel, 40-63 m, 60 Å from SiliCycle; and acetonitrile (HPLC solvent) from Spectrum or JT Baker. Purity of each reagent and solvent is greater than 99% (unless noted otherwise) and used without further purification. Water was obtained from ELGA VEOLIA system connected to in-house water source.

2. Preparation of Anhydride Byproduct 12 for Anti-Proliferation Cell Experiments FIG. 46 shows Synthesis of anhydride byproduct 12.

During drug release, Dox-DMA-Cys 6a/b generates anhydride-cysteine 12 as a byproduct (FIG. 46). Anhydride 12 is tested for cytotoxicity in anti-proliferation assays (FIGS. 31A-31E). Unlike similar byproducts 7 and 10 (FIG. 4), anhydride 12 is not a synthetic intermediate. This compound 12 was independently synthesized according to FIG. 46, by facile disulfide exchange between cysteine and cross-linker anhydride-disulfide 13. Compound 13 was synthesized according to previously published procedures.

To a solution of cross-linker anhydride-disulfide 13 (10 mg, 28 μmol, 1 eq.) in 500 μL of methanol was added L-cysteine-HCl salt (Cys, 4.5 mg, 28 μmol, 1 eq.). The reaction mixture turned yellow immediately, signaling the release of 2-mercaptopyridine/2-thiopyridone. Formation of desired product 12 and 2-thiopyridone were confirmed with $^1$H-NMR (data not shown). Color change stopped after a few min (i.e. disulfide exchange mostly finished). The reaction mixture was kept at rt in the dark for 1 h, and then analyzed by LCMS to give the following results. Anhydride 12: LCMS $t_R$ 5 min; MS(ESI+) from LCMS, exact mass calculated for $C_{13}H_{18}N_2O_6S_2$ $[M+H^+]^+$: 363.1, found: 362.9 (MS spectrum of compound 12. This MS was obtained on LCMS. Mass 380.97 is ring-opened di-carboxylic acid species 14 due to pH 8 mobile phase on LCMS. Dimer of 12 is also present. ESI FIG. S22); MS (ESI−) from LCMS (same peak), exact mass calculated for $C_{13}H_{18}N_2O_6S_2$ $[M-H^+]^-$: 361.1, found: 360.9 (MS spectrum of compound 12. This MS was obtained on LCMS. Mass 378.98 is ring-opened di-carboxylic acid species 14 due to pH 8 mobile phase on LCMS. Dimer of 12 is also present. ESI FIG. S23).

FIG. 47. Anhydride is in Equilibrium with the Dicarboxylic Acid (and its Conjugate Base) During LCMS.

FIG. 47 shows Scheme S2, equilibrium of anhydrife with the dicarboxylic acid.

In the same $t_R$ 5 min peak was also found the hydrolyzed, ring-opened, dicarboxylic acid derived from compound 12, which is in equilibrium with 12 during LCMS (likely due to LC mobile phase solvents at pH 8-9) (FIG. 47). Dicarboxylic acid 14: MS(ESI+) from LCMS (same peak), exact mass calculated for $C_{13}H_{20}N_2O_7S_2$ $[M+H^+]^+$: 381.1, found: 381.0 (ESI FIG. S22); MS (ESI−) from LCMS (same peak), exact mass calculated for $C_{13}H_{20}N_2O_7S_2$ $[M-H^+]^-$: 379.1, found: 378.9 (ESI FIG. S23).

The reaction mixture, which contained anhydride 12 and 2-mercaptopyridine/2-thiopyridone, was used as stock solution for anti-proliferation assays without further purification (see FIG. 31D, anhydride 12 showed no cytotoxic effect).

3. Characterizations of Compounds 1, 2a/b, 3, 4a/b, 5, 6a/b, 9, 10 and 12: $^1$HNMR, $^{13}$CNMR and MS Spectra (ESI FIGS. S1-S23).

4. Dox Release in Phosphate Buffer from Various Prodrugs at pH 7.4 vs. 6.5 as Followed by HPLC with Mobile Phase Solvents Buffered at pH 8-9 (ESI FIG. S24-S29).

5. Information on Cell Cultures.

5.1. Materials.

The following media, buffers, and cell culture reagents were purchased from Life Technologies—Invitrogen: DMEM/F-12 Medium without phenol red (Gibco 21041), DMEM/F-12 μMedium (Gibco 11320), Fetal Bovine Serum (FBS) (Gibco 26140), Antibiotic-Antimycotic (Anti-Anti) 100× (Gibco 15240), Trypan blue stain 0.4% (for cell counting), and Trypsin-EDTA (for cell dissociation). Good's buffers ingredients 2-[4-(2-hydroxyethyl)-piperazin-1-yl]-ethane-sulfonic acid (HEPES, pKa=7.5 at 25° C.) and 2-(N-morpholino)-ethane-sulfonic acid (MES, pKa=6.2 at 25° C.) were purchased from EMD Chemicals—Cal-Biochem. RPMI-1640 Medium (ATCC 30-2001) was purchased from American Type Culture Collection (ATCC). McCoy's 5A Medium (Lonza 12-688) was purchased from Lonza. MTS assay kit (CellTiter 96® AQueous One Solution Cell Proliferation Assay solution) was purchased from Promega Corp. Sterile cell culture flasks (25 cm2 and 75 cm2) were obtained from Corning Inc. MTS experiments were carried out in 96-well plates purchased from Greiner Bio-one.

5.2. Cell Lines.

HK2 human kidney cortex/proximal tubule cells (epithelial, non-cancerous, human papilloma-virus 16 transformed) were obtained from the American Type Culture Collection (ATCC). ES-2 human ovarian cancer cells (clear cell carcinoma, ovary, fibroblast) were gifts from Dr. Juntao Luo (Department of Pharmacology, SUNY Upstate Medical University). ES-2 cells were cultured in McCoy's 5A Medium (Lonza 12-688) supplemented with 1× Penicillin (100 IU)/

Streptomycin (100 g/ml) (Corning 30-002-CI); HK2 cells were cultured in DMEM/F12 Medium (Gibco 11320) supplemented with Anti-Anti (1×). All cells were grown with media supplemented with 10% FBS (Gibco 26140). Cells were grown in an incubator (Thermo Electron Corp., Napco series 8000 WJ, model 3578, Revco Elite II) under a humidified atmosphere of air and 5% $CO_2$ at 37° C.

5.3. Instruments.

In the 96-well plate format, 490 nm absorbance readings for MTS cell viability assays were obtained using a BioTek ELx808 microplate reader. The pH values of treatment and incubation media were measured before and after the experiments using an Orion Ross Glass Combination Micro pH electrode connected to an Orion 3-Star Benchtop pH-meter with a BNC connector (both from Thermo Scientific).

Synthesis and Characterization Methods.

General Methods. All synthetic reagents were sourced commercially and of high purity (usually >98%), see supporting information (SI) for more details. All compounds characterized below had a purity of >90% when checked on $^1H/^{13}C$ NMR, HPLC and LCMS. $^1H$ and $^{13}C$ NMR were used to confirm compound identity and purity whenever possible. When not possible (as in the case of unstable DMA prodrugs), MS was used to ascertain compound identity. MS data and HPLC retention times are given below to characterize the compounds. All reactions were carried out under dry and inert conditions unless otherwise stated.

Thin layer chromatography (TLC) was carried out on SiliaPlate silica gel 60 F254 plates using UV absorbance for visualization. Flash column chromatography was performed using SiliaFlash P60 silica gel, (40-63 μm, 60 Å).

When doxorubicin-containing material was quantified using absorbance at 480 nm, the extinction coefficient of 11,500 $M^{-1} \cdot cm^{-1}$ was used. Since all Dox conjugations described in this paper took place on the amino group of the pyranose sugar daunosamine, which is not part of the chromophore, it was assumed that all Dox conjugates would also have the same extinction coefficient at 480 nm as Dox free drug (11,500 $M^{-1} \cdot cm^{-1}$).

NMR. $^1H$ and $^{13}C$ NMR spectra were recorded on Bruker Fourier 400 MHz or 600 MHz spectrometer. Chemical shifts (δ) are expressed in ppm (reference to TMS as 0 ppm or NMR solvent peaks). Signal splitting patterns are described as singlet (s), doublet (d), triplet (t), quartet (q), multiplet (m), broad (b), or combinations thereof.

MS and LC-MS. Electron spray ionization (ESI) mass spectra were obtained under LCMS setting (on Shimadzu LCMS-2020) using pure samples. The ESI MS were acquired in positive or negative ion mode. The LC component of LCMS was ran using a combination of solvent A (water/acetonitrile 95:5, with 0.08% TEA and 0.04% acetic acid (or 0.01% formic acid), pH 8-9) and solvent B (acetonitrile with 0.08% TEA and 0.04% acetic acid (or 0.01% formic acid), pH 8-9) as the mobile phase. The column used was a Hamilton 2.1 mm (w)×100 mm (1), 5 μm particle size, PRP-1 polystyrene-divinylbenzene (PS-DVB) polymer reverse phase analytical column. The following method was used: 50-min, at 99:1 A/B for 7 min, followed by 99:1 A/B to 1:99 A/B in 30 min (the gradient), then at 1:99 A/B for 5 min, 1:99 A/B to 99:1 A/B in 2 min, and then at 99:1 A/B for 6 min, at flow rate of 0.25 mL/min. Some ES mass measurements were obtained (under standard, non-LCMS conditions) by the Mass Spectrometry Laboratory at the University of Illinois, Urbana-Champaign.

HPLC. HPLC was used to purify various compounds, monitor reaction progress, isolate desired products, and ascertain sample integrity over time. A Shimadzu HPLC system F (two LC-6AD pumps with a SPD-M20A Prominence 200-800 nm full-spectrum diode array detector) or a Shimadzu HPLC system P (one LC-20AT quaternary pump with a SPD-20A two-wavelengths UV-vis detector) connected to a semi-prep Agilent Zorbax 9.4 mm (width)×250 mm (length) SB-C18 reverse phase semi-prep column (column Z) or a Hamilton 4.1 mm (w)×150 mm (1), 10 μm particle size, PRP-1 polystyrene-divinylbenzene (PS-DVB) polymer reverse phase analytical column (column H) is run with the following general method: flow rate, 3 mL/min for semiprep column Z, or 1 mL/min for analytical column H; solvent systems A/B will be defined in specific HPLC conditions below; 60-min method: at 99:1 A/B for 10 min, followed by 99:1 A/B to 1:99 A/B in 30 min (the gradient), then at 1:99 A/B for 5 min, 1:99 A/B to 99:1 A/B in 2 min, and then at 99:1 A/B for 13 min. Specific HPLC conditions that differ in column choice (Z or H), solvents A/B, mobile phase pH (pH 2-3 or pH 8-8.5) and specific HPLC set-up (system F or P) are described below:

HPLC condition A: C18 column Z; pH 2-3; HPLC system F; phase A is water/acetonitrile 95:5 (with 0.01% TFA); phase B is acetonitrile (with 0.01% TFA).

HPLC condition B: C18 column Z; pH 2-3; HPLC system P; phase A is water/acetonitrile 95:5 (with 0.01% TFA); phase B is acetonitrile (with 0.01% TFA).

HPLC condition C: PS-DVB column H; pH 8-8.5; HPLC system P; phase A is water/acetonitrile 95:5 (with 0.08% TEA and 0.04% Acetic Acid); phase B is acetonitrile (with 0.08% TEA and 0.04% Acetic Acid).

Synthesis and characterization of intermediates, DMI pre-prodrugs, and DMA prodrugs. Compounds 7, 8 and 11 were synthesized according to published procedures.

Dox-DMI (1). To a solution of 18 mg of doxorubicin.HCl salt (30 μmol, 1 eq.), 7 mg of DMAP (60 μmol, 2 eq.) and 7 μL of pyridine (7 mg, 90 μmol, 3 eq.) in 600 μL of DMSO was added 6 mg of 2-propionic-3-methylmaleic anhydride 7 (30 μmol, 1 eq.). The reaction mixture was kept in the dark at rt. HPLC condition C showed that Dox-DMA regioisomers 2a/b ($t_R$ 20.8-22 min) were formed within 5 min, which overnight slowly converted to Dox-DMI 1 ($t_R$ 22.5-22.9 min, HPLC condition C). The product Dox-DMI 1 (10 mg) was isolated via HPLC condition A/B ($t_R$ 25.2-25.6 min) to give a yield of 47% from compound 7. Dox-DMI 1: MS (ESI$^-$): exact mass calculated for $C_{35}H_{35}NO_{15}$ [M−H$^+$]$^-$: 708.2, found 708.6 (ESI FIG. S1). $^1H$ NMR (600 μMHz, CDCl$_3$) δ 13.81 (1H, s), 13.20 (1H, s), 8.00 (1H, d, J=7.8 Hz), 7.77 (1H, t(apparent), J=8.1 Hz), 7.38 (1H, d, J=8.4 Hz), 6.00-3.50 (4H(OH), b), 5.56 (1H, d, J=3.6 Hz), 5.28 (1H, m), 4.80 (2H, s), 4.42-4.38 (1H, m), 4.12 (1H, q(apparent), J=6.6 Hz), 4.06 (3H, s), 3.71 (1H, s), 3.27 (1H, dd, J=1.8, 18.6 Hz), 3.01 (1H, d, J=18.6 Hz), 2.79 (1H, dt(apparent), J=4.0, 13.5 Hz), 2.69-2.67 (2H, m), 2.65-2.56 (2H, m), 2.41-2.40 (1H, m), 2.16 (1H, dd, J=4.2, 15.0 Hz), 1.97 (3H, s), 1.72 (1H, dd, J=3.9, 13.5 Hz), 1.31 (3H, d, J=5.4 Hz) (ESI FIG. S2). $^{13}C$ NMR (151 MHz, CDCl$_3$) δ 214.0, 187.1, 186.7, 175.7, 172.8, 172.0, 161.1, 156.4, 155.8, 139.3, 138.7, 136.0, 135.6, 134.0, 133.6, 120.9, 120.0, 118.6, 111.7, 111.5, 100.2, 76.8, 70.4, 69.1, 69.0, 65.7, 56.8, 49.3, 35.2, 34.2, 31.7, 27.2, 19.4, 17.2, 9.0 (ESI FIG. S3).

Dox-DMA (2a/b). Briefly, treating Dox-DMI 1 at pH 10 for 1 h at 37° C. in a 10 mM sodium phosphate (NaPi) buffer provided Dox-DMA 2a/b in near quantitative yield (90-99%, for example, see ESI FIGS. S24-S25 time 0 panels). See general procedure of DMI to DMA conversion below for more details. For HPLC cleavage assays, this ring-opening reaction was almost always carried out in 25 mM aq. NaPi buffer, pH 10, rt, 2 h; for cell experiments (imaging and antiproliferation), Dox-DMA 2a/b solutions were prepared as described above.

For MS experiment, a solution of Dox-DMI 1 (35.5 µg, 50 nmol, 250 µM) in 200 µL of aq. triethyl ammonium acetate (5 mM)/triethyl amine (5 mM) buffer with final pH of 9.9 was allowed to react at rt in the dark. After 1 h, HPLC at pH 8 (condition C) showed that >50% of Dox-DMI 1 ($t_R$ 22.7 min) had been converted to Dox-DMA 2a/b ($t_R$ 21.0, 21.7 min). Addition of 2 µL of 100 mM aq. acetic acid solution adjusted the pH of the reaction mixture to pH 8. The resulting solution was submitted to Mass Spectrometry Laboratory at the University of Illinois, Urbana-Champaign for mass analysis (~24 h at ambient temperature en route). Dox-DMA 2a/b: MS (ESI−), exact mass calculated for $C_{35}H_{37}NO_{16}$ [M−H$^+$]$^-$: 726.2, found 726.2 (ESI FIG. S4).

Di-tert-butyl (3-(4-methyl-2,5-dioxo-2,5-dihydrofuran-3-yl)propanoyl)glutamate (9). A solution of L-glutamic acid di-tert-butyl ester HCl salt (291 mg, 0.98 mmol, 1 eq.) and DBU (0.149 mL, 1 mmol, 1 eq.) in 2 mL of dichloromethane (DCM) was added to acyl chloride 8 (~203 mg, 1 mmol, 1 eq.) generated in situ from the corresponding carboxylic acid 7 as reported previously. The resulting reaction mixture was kept at rt for 1 h, and then directly loaded onto a silica gel column for purification. The desired product 3 (260 mg) was isolated after flash column chromatography (2:1 ethyl acetate/hexane) as an oil in 60% yield over two steps from 2-propionic-3-methylmaleic anhydride 7 (the precursor to acyl chloride 8). Compound 9: LCMS ($t_R$=27.5 min) ESI−, exact mass calculated for $C_{21}H_{31}NO_8$ [M−H$^+$]$^-$: 424.2, found: 424.3 (ESI FIG. S5). $^1$H NMR (400 MHz, CDCl$_3$) δ 6.24 (1H, d, J=7.6 Hz), 4.44-4.35 (1H, m), 2.86-2.71 (2H, m), 2.58 (2H, t, J=7.0 Hz), 2.34-2.17 (2H, m), 2.12-2.02 (1H, m), 2.09 (3H, s), 1.94-1.82 (1H, m), 1.45 (9H, s), 1.44 (9H, s) (ESI FIG. S6). $^{13}$C NMR (100 MHz, CDCl$_3$) δ 172.4, 171.0, 170.5, 166.09, 166.08, 142.6, 142.4, 82.6, 81.1, 52.6, 32.9, 31.7, 28.2, 28.1, 27.3, 20.4, 9.8 (ESI FIG. S7).

(3-(4-methyl-2,5-dioxo-2,5-dihydrofuran-3-yl)propanoyl)glutamic acid (10). To a solution of compound 9 (85 mg, 0.2 mmol) in 500 µL of DCM was added 500 µL of TFA. The resulting reaction mixture was kept at rt for 1 h. The desired product 10 (49 mg, 78% yield) was extracted into water and isolated after lyophilization. Compound 10: LCMS ($t_R$=2.5 min) ESI+, exact mass calculated for $C_{13}H_{15}NO_8$ [M+H$^+$]$^+$: 314.1, found: 314.0 (ESI FIG. S8); LCMS ESI−, exact mass calculated for $C_{13}H_{15}NO_8$ [M−H$^+$]$^-$: 312.1, found: 312.0 (ESI FIG. S9). $^1$H NMR (400 MHz, DMSO-d$_6$) δ 14.50-10.50 (0.3H, b), 8.41-8.31 (0.3H, m, minor conformer), 8.27-8.17 (0.7H, m, major conformer), 4.30-4.12 (1H, m, both conformers), 2.63 (2H, t, J=14.4 Hz), 2.43 (2H, t, J=14.4 Hz), 2.38-2.30 (1.4H, m, major conformer), 2.30-2.21 (0.6H, m, minor conformer), 2.02-1.89 (1H, m), 1.97 (3H, s), 1.87-1.67 (1H, m) (ESI FIG. S10). $^{13}$C NMR (100 MHz, D$_2$O) δ 177.0, 175.0, 174.4, 167.5, 167.0, 143.3, 142.3, 52.0, 32.4, 30.0, 25.6, 19.9, 8.9 (ESI FIG. S11).

Dox-DMI-Glu (3). To a solution of 24 mg of doxorubicin.HCl salt (41 µmol, 1 eq.) and 17 mg of DMAP (139 µmol, 3 eq.) in 2 mL of DMSO was added 14 mg of compound 10 (45 µmol, 1 eq.). The reaction mixture was kept in the dark at rt. HPLC condition C showed that Dox-DMA-Glu regioisomers 4a/b ($t_R$ 19.1-19.6 min) were formed within 5 min, which overnight slowly converted to Dox-DMI-Glu 3 ($t_R$ 21.4 min). The product Dox-DMI-Glu 3 (20 mg) was isolated using HPLC condition C to give a yield of 53%. Dox-DMI-Glu 3: Exact mass (ESI−) calculated for $C_{40}H_{42}N_2O_{18}$ [M−H$^+$]$^-$: 837.2, found 837.2 (ESI FIG. S12).

$^1$H NMR (600 MHz, DMSO-d$_6$) δ 14.00-13.88 (1H, m), 13.22-13.12 (1H, m), 8.14-8.10 (1H, m), 7.92-7.75 (2H, m), 7.62-7.52 (1H, m), 5.44 (1H, b), 5.28 (1H, s), 4.90 (1H, s), 4.59 (2H, s), 4.27-4.22 (1H, m), 4.21-4.10 (2H, m), 4.00-3.89 (3H, s), 3.80-3.15 (5H(OH), b), 3.41 (1H, s), 3.12-3.03 (1H, m), 3.00-2.90 (1H, m), 2.90-2.81 (1H, m), 2.52-2.46 (2H, m), 2.30 (2H, t, J=7.6 Hz), 2.27-2.13 (3H, m), 2.13-2.04 (1H, m), 1.95-1.85 (1H, m), 1.82 (3H, s), 1.73-1.64 (1H, m), 1.58 (1H, dd, J=3.9, 13.5 Hz), 1.11 (3H, d, J=6.4 Hz) (ESI FIG. S13). $^{13}$C NMR (151 MHz, DMSO-d$_6$) δ 213.8, 186.4, 186.3, 173.6, 173.2, 172.0, 171.8, 171.0, 160.7, 156.1, 154.5, 138.5, 137.0, 136.1, 135.3, 134.6, 134.0, 119.9, 119.7, 118.9, 110.7, 110.6, 100.5, 74.8, 70.1, 68.7, 66.5, 63.7, 56.5, 51.2 (51.1 minor conformer), 49.5, 36.5, 32.8 (32.7 minor conformer), 31.9, 30.0, 26.7, 26.23 (26.20 minor conformer), 19.3, 16.9, 8.4 (ESI FIG. S14).

Dox-DMA-Glu (4a/b). Briefly, treating Dox-DMI-Glu 3 at pH 10 for 1 h at 37° C. in a 10 mM aq. NaPi buffer provided Dox-DMA-Glu 4a/b in high yield (~90%, for example, see ESI FIGS. S26-S27 time 0 panels). See general procedure of DMI to DMA conversion below for more details.

For MS experiment, a solution of Dox-DMI-Glu 3 (42 µg, 50 nmol, 500 µM) in 100 µL of aq. triethyl ammonium acetate (5 mM)/triethyl amine (5 mM) buffer with final pH of 9.9 was allowed to react at rt in the dark. After 1.5 hr, HPLC at pH 8 (condition C) showed that >50% of Dox-DMI-Glu 3 had been converted to Dox-DMA-Glu 4a/b. Two µL of 100 mM aq. acetic acid solution was added to the reaction mixture to adjust its pH to 8. The resulting solution was submitted to Mass Spectrometry Laboratory at the University of Illinois, Urbana-Champaign for mass analysis (~24 hr at ambient temperature en route). Dox-DMA-Glu 4a/b: MS (ESI−), exact mass calculated for $C_{40}H_{44}N_2O_{19}$ [M−H$^+$]$^-$: 855.3, found 855.1 (ESI FIG. S15).

Dox-DMI-Cys (5). To a solution of compound 11 (58 mg, 0.07 mmol, 1 eq.) in 1 mL of DMSO was added cysteine.HCl salt (21 mg, 0.14 mmol, 2 eq.). The resulting reaction mixture was kept under Ar at rt in the dark for 1 h. Reaction progress was monitored (s.m. 11 $t_R$ 31.1 min, product Dox-DMI-Cys 5 $t_R$ 24.0 min, HPLC condition A), and the desired product (50 mg, 85% yield) was isolated using HPLC conditions A and B (see general procedures of HPLC section for details). Dox-DMI-Cys 5: LCMS ($t_R$=21.5 min) ESI+, exact mass calculated for $C_{40}H_{45}N_3O_{16}S2$ [M+H$^+$]$^+$: 888.2, found: 888.3 (ESI FIG. S16); LCMS ESI−, exact mass calculated for $C_{40}H_{45}N_3O_{16}S2$ [M−H$^+$]$^-$: 886.2, found: 886.3 (ESI FIG. S17). $^1$H NMR (600 MHz, DMSO-d$_6$) δ 14.23-13.63 (1H, b), 13.51-12.91 (1H, b), 8.14-8.06 (1H, m), 7.90-7.82 (2H, m), 7.64-7.56 (1H, m), 5.58-5.38 (1H, b), 5.32-5.26 (1H, m), 5.20-4.50 (5H, b), 4.97-4.89 (1H, m), 4.58 (2H, s), 4.24 (1H, q(apparent), J=6.5 Hz), 4.17 (1H, d(apparent), J=13.9 Hz), 4.00-3.92 (4H, m), 3.41 (1H, s), 3.33-3.26 (2H, m), 3.25-3.19 (1H, m), 3.11-3.02 (2H, m), 2.97 (1H, d, J=18.1 Hz), 2.90 (1H, d, J=17.8 Hz), 2.80-2.71 (2H, m), 2.53-2.46 (2H, m), 2.27-2.19 (3H, m), 2.13-2.06 (1H, m), 1.83 (3H, s), 1.60-1.54 (1H, m), 1.12 (3H, d, J=6.4 Hz) (ESI FIG. S18). $^{13}$C NMR (151 µMHz, DMSO-d$_6$) δ 213.8, 186.5, 186.4, 172.1, 171.8, 171.0, 169.2, 160.8, 156.1, 154.5, 138.6, 136.9, 136.2, 135.5, 134.6, 134.1, 119.9, 119.7, 119.0, 110.7, 110.6, 100.4, 74.8, 70.2, 68.7, 66.6, 63.7, 56.6, 51.7, 49.5, 38.5, 37.9, 36.8, 36.6, 33.1, 32.0, 26.7, 19.4, 16.9, 8.4 (ESI FIG. S19).

Dox-DMA-Cys (6a/b). Briefly, treating Dox-DMI-Cys 5 at pH 10 for 1 h at 37° C. in a 10 mM aq. NaPi buffer provided Dox-DMA-Cys 6a/b in near quantitative yield (~99%, for example, see ESI FIGS. S28-S29 time 0 panels). See general procedure of DMI to DMA conversion below for more details.

For MS experiment, to a solution of Dox-DMI-Cys 5 (89 μg, 100 nmol, 100 μM) in 1 mL of 10 mM aq. NaPi buffer (pH 8) was added small aliquots of 1 μM aq. NaOH to adjust the pH to 9.9. The reaction solution was allowed to stand at rt for 1 h in the dark, during which the pH decreased to ~9.6. After 1 h, the reaction mixture was injected into LCMS. Dox-DMA-Cys 6a/b: LCMS ($t_R$ 17.9 and 18.5 min) ESI+, exact mass calculated for $C_{40}H_{47}N_3O_{17}S_2$ $[M+H^+]^+$: 906.2, found 906.3 (ESI FIG. S20); LCMS ESI−, exact mass calculated for $C_{40}H_{47}N_3O_{17}S_2$ $[M-H^+]^-$: 904.2, found: 904.4 (ESI FIG. S21).

General procedure for converting DMI pre-prodrugs 1/3/5 to DMA prodrugs 2/4/6, respectively, and the preparation of various DMA prodrug solutions for HPLC drug release assays and cell experiments (antiproliferation assays and imaging studies). A general procedure for converting DMI pre-prodrugs 1/3/5 to DMA prodrugs 2/4/6: To a 50-100 μM stock solution of DMI 1/3/5 in 0.5-5 mL of 10 mM aq. NaPi buffer at pH 8 was added small aliquots of 0.1 M aq. NaOH to adjust the pH to 10. The reaction solution was allowed to stand at 37° C. for 1 h in the dark. As shown in ESI FIGS. S24-S29 time 0 panels, this simple procedure could achieve near-quantitative DMI to DMA conversion (usually 90-99% yield of DMA prodrugs 2/4/6). To this solution of DMA 2/4/6 was added small aliquots of 0.1 or 1 M aq. HCl to adjust the pH to 8 (or the desired final experimental pH between 6 to 8 for HPLC drug release assays). For some 1 to 2 conversions, the pH of a stock solution of DMI 1 in 25 mM aq. NaPi buffer was adjusted from 8 to 10, and then allowed to stand at rt for 1-2 h (sometimes the pH decreased to ~9.6 after 1 h, and was readjust to pH 10 again if DMI to DMA conversion was <90% by 1 h at rt).

For cell experiments, a pH 8 or pH 10 (directly from DMI to DMA conversion) solution of DMA 2/4/6 was sterilized by filtering through a 0.2-micron membrane. Subsequently, this 50-100 μM DMA 2/4/6 stock solution was diluted to a final concentration of 0.5-8 μM (for experiments in FIGS. 29-32) with pH 7.2-7.7 or pH 6.1-6.9 cell media (DMEM-F12 without phenol red, pH-controlled with Good's buffer compounds HEPES, 60 mM, for pH 7.2-7.7, or MES, 60 mM, for pH 6.1-6.9). At this point, small amounts of 10 (or 25) mM of sterile aq. NaPi buffer (stock filtered through 0.2 micron membrane) and DMSO were added to make sure all samples tested contained the same amount of extra phosphate (~1 mM) and DMSO (1% by volume in antiproliferation 96-well plate assays, 0.5% in imaging studies) as the negative (vehicle) or positive (Dox) control.

For cytotoxicity assay against noncancerous HK2 cells shown in FIGS. 29B, 30B and 31B (concentration scan from 3 nM to 30 μM), a similar procedure was used except the following, using DMI 1 to DMA 2 as an example: (a) A more concentrated 187 μM stock solution of Dox-DMI 1 (75 nmol) in 400 μL of 10 mM aq. NaPi buffer (pH 8) was used for conversion to Dox-DMA 2a/b (at pH 10, 37° C., 1 h); (b) Subsequently, the Dox-DMA 2a/b solution was filtered (0.2 micron membrane), and then diluted to 10 μM and 30 μM stocks with pH 7.4 cell media (DMEM-F12 without phenol red), followed by serial dilutions to give the final concentrations.

HPLC Assay of Dox Release from DMA Prodrugs 2/4/6 at Different pH Values.

Release of Dox from Dox-DMA 2a/b, Dox-DMA-Glu 4a/b and Dox-DMA-Cys 6a/b were studied at different pH and temperature (25° C. or 37° C.) through monitoring by HPLC condition C (mobile phase at pH 8-9). Various DMA prodrugs of Dox were converted from their corresponding DMI pre-prodrugs (see general procedure of DMI to DMA conversion section above for more details on DMA solution preparations). The pH of the DMA prodrug solution was adjusted to different pH values in the range of pH 7.4-6.0. Then the solution was allowed to sit at rt (~25° C.) or placed in an incubator at 37° C. in the dark for up to a few days (the pH did not change significantly during this time). Release of Dox, consumption of DMA prodrug (s.m.) and formation of DMI byproduct were monitored using HPLC condition C (pH 8-9, 480 nm, ~5 nmol of s.m. per HPLC run). Representative HPLC traces are shown in ESI FIGS. S24-S29 (see these figures and their captions for more detailed information). Areas under the peaks were integrated using the HPLC program LabSolutions Lite to give the percentages reported in FIGS. 24-28.

Figure 48:
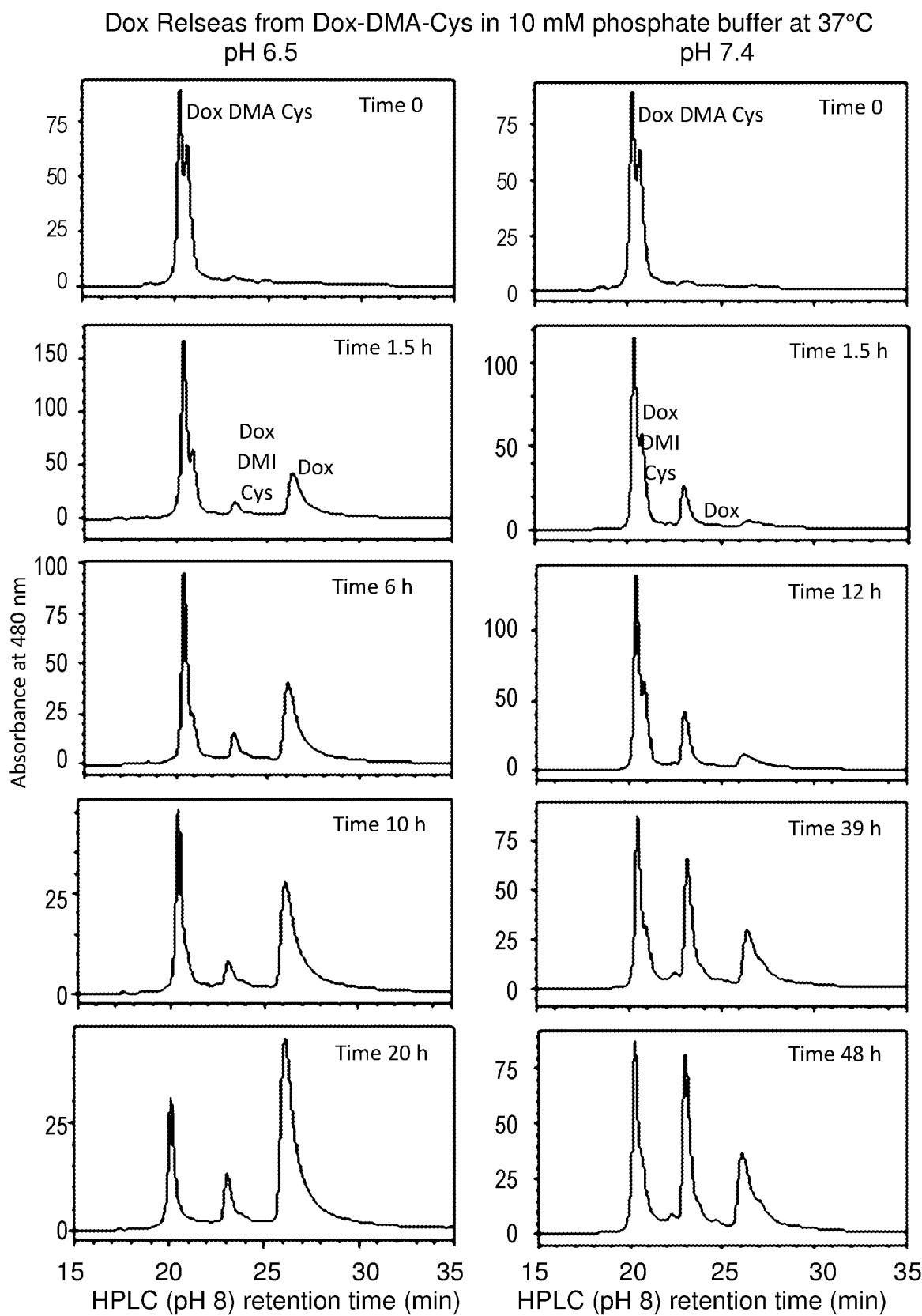
FIG. 48 shows Dox release from Dox-DMA-Cys prodrug 6a/b in 10 mM aq. sodium phosphate buffer, at 37° C., pH 7.4 vs. 6.5, as followed by HPLC (condition C, pH 8-9, 480 nm is absorbance of Dox). Minor shifts in retention times are due to small variations in pH of HPLC solvents.
Figure 49:
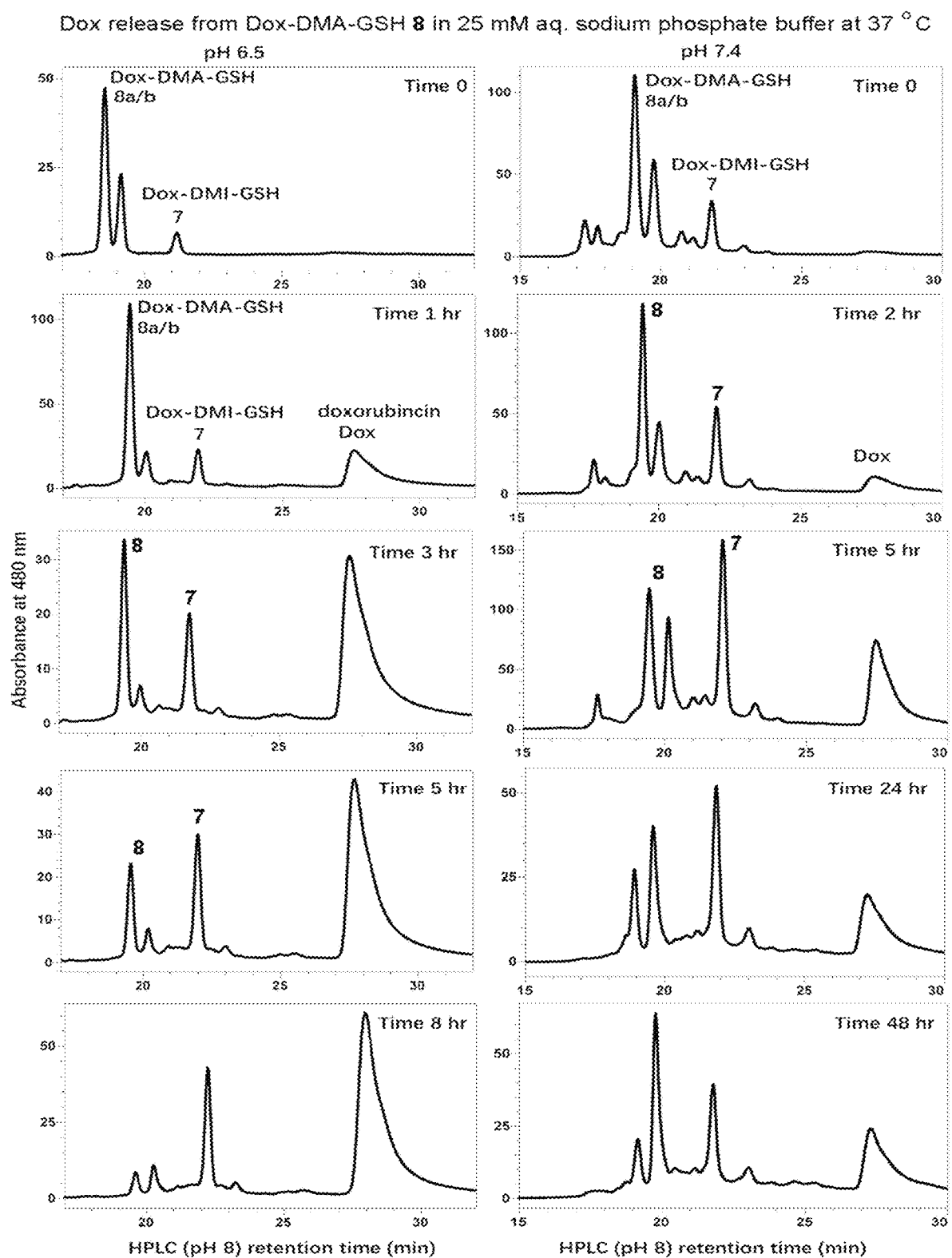
FIG. 49 shows Dox release from Dox-DMA-GSH prodrug 8 in 25 mM aq. sodium phosphate buffer, at 37° C., pH 7.4 vs. 6.5, as followed by HPLC (condition E, pH 8, 480 nm is absorbance of Dox). Areas under the peaks were integrated to give the percentages reported in Table 2. Minor shifts in retention times are due to small variations in pH of HPLC solvents. At pH 7.4, the peak with tR~20 min at 24 or 48 hr is mostly not DMA 8 but a decomposition byproduct (confirmed by MS, data not shown).

FIGS. 48 and 49 show an unexpected difference in product purity when the DMI pre-prodrug is converted to the corresponding DMA prodrug in alkaline solution. When converted from their DMI pre-prodrugs (rt, pH 10, 2 hr), the Dox-DMA-Cys disulfide has less unknown decomposition product (impurity) than Dox-DMA-GSH disulfide. In FIGS. 48 and 49, DMA drug release at 37° C., pH 7.4 or pH 6.5, Dox-DMA-Cys (FIG. 48) vs. Dox-DMA-GSH (FIG. 49), were followed by HPLC (480 nm absorbance tracks all Dox-containing compounds, such as DMA, DMI, free Dox, and other unknown decomposition products containing Dox). Compare Time 0 (top panels in FIGS. 48-49), just after DMI pre-prodrug to DMA prodrug conversion was completed: In the FIG. 48, Dox-DMA-Cys is clean, just the two DMA peaks (DMA has two isomers) around 20 min, regardless of pH. In FIG. 49, Dox-DMA-GSH is much less clean, especially at pH 7.4.

Peptides such as GSH (a 3 amino acid residue peptide) posed some difficulties for DMI to DMA conversion. Dox-DMI-GSH cannot be completely ring-opened to Dox-DMA-GSH. Smaller and more polar molecules, such as single amino acid Cys, did not have this problem. Dox-DMI-Cys pre-prodrug to Dox-DMA-Cys prodrug conversion could be quantitative, i.e., substantially complete without side products. The DMI to DMA conversion difficulty is probably caused by the fact that GSH is a larger and more hydrophobic molecule than Cys.

Suitable molecules that can be the targeting or detargeting agent include polar (charged in aqueous solution at pH 6.8) modulators that are either thiol-containing (for making disulfide bonds) include polar small molecules (with 1-3 overall negative charges or zwitterionic) with MW<300. These molecules include molecules such as D/L-homo-Cys, thiol-containing mono- or di-carboxylic acids, sulfonic acids, phosphonic acids.

Where non-disulfide linkages are employed, polar small molecule (with 1-3 overall negative charges or zwitterionic) with MW<500 may be suitable. These molecules include molecules such as amino acids, mono- or di-carboxylic acids, alcohols, amines, sulfonic acids, phosphonic acids.

Antiproliferation assays against ES2 cancer cells at different pH values. In 96-well plates, ~3,000 cancerous ES2 cells were seeded per well then grown for 24-48 h until 30-40% confluency. After removing the growth media, cells were treated with different DMA prodrugs 2/4/6, anhydride byproducts 7/10/12, free drug Dox (positive control, with 1% DMSO), or buffer/DMSO negative vehicle control (see general procedure of DMI to DMA conversion section above for more details on treatment sample preparations; the amount of DMSO, 1%, and extra phosphate, ~1 mM, in all wells were kept constant) at a given concentration (in the range of 0.5-8 µM) and pH (as shown in FIGS. 29-32) in modified DMEM/F-12 media (without phenol red, supplemented with 60 mM of MES for pH 6.1-6.9 or 60 mM HEPES for pH 7.2-7.7 experiments) for 1-8 h at 37° C. in the incubator. Treatment solution volume was 50-100 µL per well, with a set volume per well for all wells in a plate. After treatment solutions were removed, cells were incubated with normal growth media (pH 7.4, 10% FBS) and allowed to proliferate for additional 2-4 days until the buffer vehicle negative control wells have reached >80% confluency, then MTS cell viability assays were performed (i.e. growth media was replaced with 50 µL of pH 7.4 DMEM/F-12 media without phenol red, 10 µL of MTS reagent was added, absorbance at 490 nm was recorded 0.5-4 h afterwards). The pH values of treatment solutions were measured before and after each experiment to give the pH ranges reported in FIGS. 29-32.

Cytotoxicity assays with noncancerous HK2 kidney cells. For cytotoxicity assay against noncancerous cells (results shown in FIGS. 29B, 30B and 31B), ~3,000 HK2 kidney cells per well were seeded in a 96-well plate; after incubation at 37° C. with 5% $CO_2$ overnight, the HK2 cells were treated with vehicle negative control (buffer/DMSO), or serial dilutions of free Dox or DMA prodrugs 2/4/6 at concentrations ranging from 3 nM to 30 µM (see general procedure of DMI to DMA conversion section above for more details on treatment sample preparations) for 2-2.5 h at 37° C. in the incubator. Dox and DMA prodrug experiments were carried out on separate plates. After treatment solutions were removed, cells were incubated with normal growth media (pH 7.4, 10% FBS) and allowed to proliferate for additional 2-3 days until the buffer vehicle negative control wells have reached >70% confluency, then MTS cell viability assays were performed as described above. The cell viability in vehicle (buffer/DMSO) negative control treatment groups were treated as 100% during normalization of data.

Statistical information for antiproliferation data. Error bars shown in figures reflect ±1 standard deviation (SD). Statistical significance of the difference between the chosen data sets was evaluated using unpaired (unequal variance), two-tailed Student's t-test (*: $P<0.05$; : $P<0.01$; *: $P<0.001$). All presented data were reproduced in at least one other plate. However, due to plate-to-plate and week-to-week cell variabilities, only data from one representative plate was plotted.

Imaging studies (confocal microscopy). Approximately 8,000 ES2 cells were seeded on a collagen-coated glass dish (MatTek Corporation, part No. P35GCOL-0-10-C) and cultured in McCoy's 5A medium with 10% fetal bovine serum and 1% penicillin-streptomycin at 37° C. in the incubator (5% $CO_2$) overnight. After removing growth medium, cells were treated with serum-free, pH-specific (pH 6.7 or 7.7) DMEM/F12 media containing 8 µM of DMA prodrugs 2/4/6 (see general procedure of DMI to DMA conversion section above for more details on treatment sample preparations), 8 µM of DMI 1/3/5, or 4 µM of free Dox for 1 h at 37° C. in the incubator (5% $CO_2$). After treatment solution was removed, the cells were washed 1× with 100 µL of DMEM/F12 pH-specific media. Prior to fluorescence imaging, the nuclei of cells were stained with 1 µg/mL Hoechst 33342 in PBS for 20 min at 37° C. in the incubator. Afterwards, cells stayed in pH-specific DMEM/F12 media during imaging. Images were taken with a Leica TCS SP5 Confocal Laser Scanning Microscope with a 40× or 63× oil lens at Dox fluorescence (Ex: 488 nm; Em: 565-630 nm) and nuclei staining dye (Ex: 405 nm; Em: 440-470 nm) channels. The images in FIGS. 33-36 were processed using LAS X and ImageJ.

Chemotherapeutic agents for use in combination with the present invention include: Alkylating agents: (Mustard gas derivatives: Mechlorethamine, Cyclophosphamide, Chlorambucil, Melphalan, and Ifosfamide; Ethylenimines: (Thiotepa and Hexamethylmelamine; Alkylsulfonates: Busulfan; Hydrazines and Triazines: Altretamine, Procarbazine, Dacarbazine and Temozolomide; Nitrosureas: Carmustine, Lomustine and Streptozocin) Nitrosureas: (note that nitrosureas are unique because, unlike most types of chemo treatments, they can cross the blood-brain barrier and can be useful in treating brain tumors); Metal salts: Carboplatin, Cisplatin, and Oxaliplatin), plant alkaloids: (Vinca alkaloids: Vincristine, Vinblastine and Vinorelbine); Taxanes: (Paclitaxel and Docetaxel and alburment bound taxol (Abraxane); Podophyllotoxins) Etoposide and Tenisopide; Camptothecan analogs: (Irinotecan and Topotecan), Antitumor antibiotics: (Anthracyclines: Doxorubicin, Daunorubicin, Epirubicin, Mitoxantrone, and Idarubicin; Chromomycins: Dactinomycin and Plicamycin); Miscellaneous: (Mitomycin and Bleomycin); Antimetabolites: (Folic acid antagonist, Methotrexate); Pyrimidine antagonist: (5-Fluorouracil, Foxuridine, Cytarabine, Capecitabine, and Gemcitabine;) Purine antagonist: (6-Mercaptopurine and 6-Thioguanine); Adenosine deaminase inhibitor: (Cladribine, Fludarabine, Nelarabine and Pentostatin); Topoisomerase inhibitors: (Topoisomerase I inhibitors, Ironotecan, topotecan); Topoisomerase II inhibitors: (Amsacrine, etoposide, etoposide phosphate, teniposide); Proteosome inhibitors: (Bortezomib, carfilzomib, Ixazomib); Other agents: (Ribonucleotide reductase inhibitor, Hydroxyurea); Adrenocortical steroid inhibitor: (Mitotane); Enzymes: (Asparaginase and Pegaspargase); Antimicrotubule agent: (Estramustine); Retinoids: (Bexarotene, Isotretinoin, Tretinoin, ATRA); Antibodies: (Alemtuzumab, transtuzumab, cetuximab, brentuximab vedotin, ado-transtuzumab emtasine, Denileukin difitox, blinatumomab, bevacizumab, alemtuzumab, ipilimumab, nivolumab, ofatumumab, pembrolizumab, rituximab); Kinase inhibitors: (inhibitors of ALK (Crizotinib, Ceritinib, Alectinib, Brigatinib), BCR-Abl (Crizotinib, Ceritinib, Alectinib, Brigatinib), B-Raf (Crizotinib, Ceritinib, Alectinib, Brigatinib), BTK (Ibrutinib), CDK family (Palbociclib, Sorafenib, Ribociclib), c-Met (Crizotinib, Cabozantinib), EGFR family (Gefitinib, Erlotinib, Lapatinib, Vandetanib, Afatinib, Osimertinib), JAK family (Ruxolitinib, Tofacitinib), Mek1/2 (Trametinib), PDGFR a/b (Axitinib, Gefitinib, Imatinib, Lenvatinib, Nintedanib, Pazopanib, Regorafenib, Sorafenib, Sunitinib), RET (Vandetanib), Src family (Bosutinib, Dasatinib, Ponatinib, Vandetanib), VEGFR family (Axitinib, Lenvatinib, Nintedanib, Regorafenib, Pazopanib, Sorafenib, Sunitinib)).

The term "pharmaceutically acceptable" means approvable by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, chalk, silica gel, sodium stearate, glycerol monostearate, sodium chloride, glycerol, propylene, glycol, water, ethanol and the like. The composition, if desired, can also contain minor amounts of wetting or emulsifying agents, or pH modifying and/or buffering agents. These compositions can take the form of solutions, suspensions, and emulsions. Examples of suitable pharmaceutical carriers are described in "Remington's Pharmaceutical Sciences" by E. W. Martin. Such compositions will contain a therapeutically effective amount of the pre-prodrug, leading to a therapeutic amount of the prodrug after activation, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the invention which will be determined based on a balance between required cytotoxicity (therapeutic benefit), and acute and cumulative toxicity which can be determined by standard clinical techniques. In addition, in vitro and pre-clinical animal assays may optionally be employed to help identify optimal dosage ranges. The precise dose to be employed in the formulation will also depend on the route of administration, the targeted condition, history of prior administration of drugs to the patient or subject, and should be decided according to the judgment of the practitioner and each patient's circumstances. Effective doses may be extrapolated from dose-response curves derived from in vitro or animal model test systems.

Cumulative dose should generally be below a cumulative lifetime dose of 550 mg/m$^2$. Doses may be administered e.g, every 21 days or three weeks. For example, a dose of about 60 to 75 mg/m$^2$ equivalent of anthracycline, IV repeated every 21 days as a single agent; 40 to 75 mg/m$^2$ IV equivalent of anthracycline repeated every 21 to 28 days in combination with other chemotherapy agents. The drug may also be administered topically, e.g., 50 to 150 mg equivalent of anthracycline in 150 mL of normal saline instilled into the bladder. The solution is then retained for at least 30 minutes.

The disubstituted maleimide pre-prodrug may be supplied as a lyophilized powder vial or an injectable solution having about 2 mg/ml solution. As discussed above, in any case, the pre-prodrug is processed ex vivo before administration with a base, e.g., pH 10, to convert the DMI to DMA with high purity and specificity. Preferably, the resulting DMA is substantially pure, and preferably at least 95% pure, consisted of mostly (>90%) decyclized DMA and a small amount (<5%) of starting DMI, with less than 5% other side products.

A targeting agent or moiety is one which has an affinity for particular tissues or cells. A detargeting agent is one which has a low affinity for particular tissues or cells. In the present context, a ligand which is charged at physiological pH is detargeted for cellular uptake, while an antibody which has a high affinity for a cell surface receptor would be targeted to the cell.

A unit dosage form generally provides sufficient dose for a single patient, but a limited amount to avoid undue waste or risk of overdose or miscalculation by pharmacist.

BSA measures the total surface area of the body and is used to calculate drug dosages and medical indicators or assessments. Various estimates of body surface area are available, e.g., the Mosteller formula, which takes the square root of the height (cm) multiplied by the weight (kg) divided by 3600. A large male may have a BSA of 3 m$^2$, with an average of 1.7 m$^2$.

While typical dose as a sole agent, 60 to 75 mg/m$^2$, in combination therapy, lower doses may be employed. Therefore, unit dosage forms may include up to 225 mg equivalent of anthracycline, and for example, unit dosage forms of 1 mg, 2 mg, 5 mg, 10 mg, 15 mg, 20 mg, 25 mg, 40 mg, 50 mg, 75 mg, 100 mg, 125 mg, 150 mg, 175 mg, 200 mg, 225 mg, 250 mg, 275 mg, and/or 300 mg may be provided. These may be used in appropriate combination to achieve a desired dose.

The invention also provides a pharmaceutical pack or kit comprising one or more containers filled with one or more of the ingredients of the pharmaceutical compositions of the invention. Optionally associated with such container(s) can be a notice in the form prescribed by governmental agency regulating the manufacture, use or sale of pharmaceuticals or biological products, which notice reflects approval by the agency of manufacture, use or sale for human administration.

The compositions and methods described herein can be administered to a subject in need of treatment, e.g., in need of treatment for cancer or sarcoma. In some embodiments, the methods described herein comprise administering an effective amount of compositions described herein, to a subject in order to alleviate a symptom. As used herein, "alleviating a symptom" is ameliorating any condition or symptom associated with a given condition. As compared with an equivalent untreated control, such reduction is by at least 50%, 60%, 80%, 90%, 95%, 99%, 99.5%, 99.9%, 99.99% or more as measured by any standard technique. A variety of means for administering the compositions described herein to subjects are known to those of skill in the art.

Effective amounts, toxicity, and therapeutic efficacy can be determined by standard pharmaceutical procedures in cell cultures or experimental animals, e.g., for determining the ED50 (the dose therapeutically effective in 50% of the population). The dosage can vary depending upon the dosage form employed and the route of administration utilized. The dose ratio between toxic and therapeutic effects is the therapeutic index and can be expressed as the ratio ED$_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the IC$_{50}$ (i.e., the concentration of an engineered microbial cell which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation, among others. The dosage can be determined by a physician and adjusted, as necessary, to suit observed effects of the treatment.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. In some embodiments, the terms can represent a 100% decrease, i.e., a non-detectable level as compared to a reference level. In the context of a marker or symptom, a "decrease" is a statistically significant decrease in such level. The decrease can be, for example, at least 10%, at least 20%, at least 30%, at least 40% or more, and is preferably down to a level accepted as within the range of normal for an individual without such disorder. In some instances, the symptom can be essentially eliminated which means that the symptom is reduced, i.e., the individual is in at least temporary remission.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or non-human animal. Usually the non-human animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Animals also include armadillos, hedgehogs, and camels, to name a few. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, cow, or pig, but is not limited to these examples. Mammals other than humans can be advantageously used as subjects that represent animal models of a given condition. A subject can be male or female.

A subject can be one who has been previously diagnosed with or identified as suffering from or having a condition in need of treatment, and optionally, have already undergone treatment. Alternatively, a subject can also be one who has not been previously diagnosed as having a condition. For example, a subject can be one who exhibits one or more risk factors or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g., cancer or inflammation. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g., a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications; including literature references, issued patents, published patent applications, and co-pending patent applications; cited throughout this application are expressly incorporated herein by reference for all purposes, including, but not limited to, describing and disclosing, for example, the methodologies described in such publications that might be used in connection with the technology described herein.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

TABLE 1 pH-dependent release of doxorubicin from Dox-DMA-GSH 8 at 25° C. in phosphate buffer.

| pH | Time | Mol. % of DMA 8 | Mol. % of DMI 7 formed | Mol. % of Dox Released | Mol. % of Decomposition Products |
|---|---|---|---|---|---|
| pH 7.4 | 0 hr | 94 | 0 | 0 | 6 |
| | 24 hr | 45 | 23 | 19 | 13 |
| | 44 hr | 29 | 29 | 28 | 14 |
| | 69 hr | 18 | 32 | 27 | 23 |
| | 94 hr | 16 | 30 | 31 | 23 |
| | 123 | 11 | 27 | 23 | 39 |
| | 144 | 10 | 27 | 23 | 40 |
| pH 7.0 | 0.5 hr | 75 | 7 | 8 | 10 |
| | 4 hr | 71 | 11 | 8 | 10 |
| | 21 hr | 31 | 24 | 34 | 11 |
| | 25 hr | 26 | 24 | 35 | 15 |
| | 30 hr | 22 | 25 | 38 | 15 |
| | 48 hr | 12 | 30 | 43 | 15 |
| pH 6.8 | 0.2 hr | 79 | 8 | 4 | 9 |
| | 15 hr | 31 | 18 | 42 | 9 |
| | 20 hr | 26 | 21 | 43 | 10 |
| | 22 hr | 22 | 21 | 47 | 10 |
| | 24 hr | 16 | 25 | 49 | 10 |
| | 48 hr | 6 | 22 | 54 | 18 |
| pH 6.5 | 1 hr | 69 | 7 | 10 | 14 |
| | 6 hr | 32 | 11 | 43 | 14 |
| | 9 hr | 24 | 11 | 50 | 15 |
| | 24 hr | 5 | 13 | 67 | 15 |
| pH 6.3 | 0.1 hr | 74 | 9 | 9 | 8 |
| | 3.5 hr | 36 | 9 | 47 | 8 |
| | 6 hr | 23 | 8 | 59 | 10 |
| | 24 hr | 4 | 16 | 68 | 12 |
| pH 6.0 | 0.1 hr | 67 | 12 | 16 | 5 |
| | 2 hr | 28 | 10 | 57 | 5 |
| | 5 hr | 12 | 10 | 68 | 10 |
| | 24 hr | 0 | 10 | 80 | 10 |

TABLE 2 pH-dependent release of doxorubicin from Dox-DMA-GSH 8 at 37° C. in phosphate buffer.

| pH | Time | Mol. % of DMA 8 | Mol. % of DMI 7 formed | Mol. % of Dox Released | Mol. % of Decomposition Products |
|---|---|---|---|---|---|
| pH 7.4 | 0 hr | 73 | 10 | 0 | 17 |
| | 2 hr | 53 | 17 | 10 | 20 |
| | 5 hr | 23 | 24 | 33 | 20 |
| | 9 hr | 19 | 26 | 33 | 22 |
| | 12 hr | 18 | 26 | 34 | 22 |
| | 16 hr | 14 | 27 | 34 | 25 |
| | 20 hr | 12 | 27 | 36 | 25 |
| | 24 hr | 12 | 24 | 36 | 28 |
| | 48 hr | 8 | 18 | 29 | 45 |
| | 81 hr | 1 | 11 | 28 | 60 |
| pH 6.5 | 0 hr | 94 | 6 | 0 | 0 |
| | 1 hr | 56 | 8 | 35 | 1 |
| | 3 hr | 20 | 10 | 69 | 1 |
| | 4 hr | 16 | 10 | 73 | 1 |
| | 5 hr | 13 | 12 | 74 | 1 |
| | 6.5 hr | 6 | 12 | 76 | 6 |
| | 8 hr | 2 | 12 | 78 | 8 |
| | 9 hr | 2 | 16 | 74 | 8 |
| | 12 hr | 1 | 16 | 73 | 10 |

TABLE 3 pH-dependent release of doxorubicin from Dox-DMA-GSH 8 at 37° C. with 45% FBS.

| pH | Time | Mol. % of DMA 8 | Mol. % of DMI 7 formed | Mol. % of Dox Released | Mol. % of Decomposition Products |
|---|---|---|---|---|---|
| pH 7.4 | 0 hr | 86 | 5 | 0 | 9 |
| | 1 hr | 81 | 10 | 0 | 9 |
| | 4 hr | 35 | 15 | 11 | 29 |
| | 8 hr | 22 | 20 | 11 | 47 |
| | 24 hr | 15 | 22 | 13 | 50 |
| | 32 hr | 3 | 21 | 11 | 65 |
| | 45 hr | 0 | 6 | 10 | 84 |
| pH 6.5 | 0 hr | 90 | 8 | 0 | 2 |
| | 1 hr | 61 | 10 | 27 | 2 |
| | 2 hr | 47 | 13 | 37 | 3 |
| | 3 hr | 38 | 13 | 45 | 4 |
| | 5 hr | 11 | 13 | 57 | 19 |
| | 6 hr | 8 | 12 | 59 | 21 |
| | 7 hr | 6 | 11 | 61 | 22 |
| | 8.5 hr | 5 | 10 | 62 | 23 |
| | 12 hr | 4 | 10 | 63 | 23 |
| | 24 hr | 3 | 3 | 65 | 29 |
| | 28.5 hr | 2 | 2 | 59 | 37 |
| | 32 hr | 2 | 2 | 59 | 37 |
| | 48 hr | 0 | 2 | 54 | 44 |

TABLE 4

Exact numerical values of the mean, the standard deviation, and the P values used to generate the cell viability graphs in FIGS. 7A-7I and FIGS. 8-10.
Dose Dependence

| FIG. 7A ES-2, 6 hr (n = 5) | pH 6.6-6.8 Cell Viability Average (Avg) | pH 6.6-6.8 Ave, Standard Deviation (SD) | pH 7.2-7.5 Avg | pH 7.2-7.5 SD | P value |
|---|---|---|---|---|---|
| Buffer (4% 25 mM Pi) | 96 | 3 | 100 | 5 | |
| Dox-DMI-GSH 0.5 μM | 90 | 4 | 97 | 5 | |
| Dox-DMI-GSH 1 μM | 79 | 3 | 80 | 3 | |
| Dox-DMA-GSH 0.5 μM | 64 | 12 | 61 | 14 | |
| Dox-DMA-GSH 1 μM | 22 | 4 | 45 | 8 | pH 6.6-6.8 vs. pH 7.2-7.5: 0.00141 |
| Dox 0.5 μM | 32 | 2 | 16 | 1 | pH 6.6-6.8 vs. pH 7.2-7.5: 0.0000225 |
| P value | Dox-DMA-GSH 1 μM vs. Dox 0.5 μM: 0.00331 | | Dox-DMA-GSH 1 μM vs. Dox 0.5 μM: 0.00127 | | |

| FIG. 7B MDA-MB231, 2 hr (n = 5) | pH 6.3-6.4 Avg | pH 6.3-6.4 SD | pH 7.6-7.7 Avg | pH 7.6-7.7 SD | P value |
|---|---|---|---|---|---|
| Buffer | 92 | 11 | 100 | 12 | |
| Dox - - - MA-GSH 4 μM | 53 | 6 | 68 | 2 | |
| Dox-DMA-GSH 6 μM | 24 | 2 | 68 | 2 | |
| Dox-DMA-GSH 8 μM | 13 | 1 | 68 | 7 | pH 6.3-6.4 vs. pH 7.6-7.7: 0.0000311 |
| Dox 3 μM | 30 | 5 | 15 | 2 | pH 6.3-6.4 vs. pH 7.6-7.7: 0.00213 |
| P value | Dox-DMA-GSH 8 μM vs. Dox 3 μM: 0.0015 | | Dox-DMA-GSH 8 μM vs. Dox 3 μM: 0.0000242 | | |

TABLE 4-continued

Exact numerical values of the mean, the standard deviation, and the P values used
to generate the cell viability graphs in FIGS. 7A-7I and FIGS. 8-10.
Dose Dependence

| FIG. 7C OVCAR3, 2 hr (n = 5) | pH 6.3-6.4 Avg | pH 6.3-6.4 SD | pH 7.4-7.6 Avg | pH 7.4-7.6 SD | P value |
|---|---|---|---|---|---|
| Buffer | 102 | 3 | 100 | 6 | |
| Dox-DMA-GSH 4 μM | 64 | 3 | 57 | 3 | |
| Dox-DMA-GSH 6 μM | 18 | 1 | 38 | 2 | pH 6.3-6.4 vs. pH 7.4-7.6: 0.00000102 |
| Dox 3 μM | 57 | 13 | 24 | 2 | pH 6.3-6.4 vs. pH 7.4-7.6: 0.00391 |
| P value pH scan | Dox - - - DMA - - - GSH 6 μM vs. Dox 3 μM: 0.00213 | | Dox - - - DMA - - - GSH 6 μM vs. Dox 3 μM: 0.00000177 | | |

FIG. 7E, pH scan, ES2, 2.5 hr, n = 3 for buffer, n = 4 for others

| pH | Buffer Avg | Buffer SD | Dox-DMA-GSH 2 μM Avg | Dox-DMA-GSH 2 μM SD | Dox 1 μM Avg | Dox 1 μM SD | P value |
|---|---|---|---|---|---|---|---|
| 7.2-7.4 | 100 | 4 | 80 | 3 | 23 | 1 | Dox-DMA-GSH 2 μM vs. Dox 1 μM: 0.00000485 |
| 7.2 | 105 | 2 | 69 | 8 | 25 | 3 | Dox-DMA-GSH 2 μM vs. Dox 1 μM: 0.000676 |
| 6.8-6.9 | 106 | 3 | 63 | 2 | 42 | 2 | Dox-DMA-GSH 2 μM vs. Dox 1 μM: 0.00000322 |
| 6.7-6.8 | 96 | 2 | 51 | 3 | 44 | 3 | |
| 6.5 | 101 | 4 | 50 | 5 | 49 | 4 | |
| 6.3-6.4 | 87 | 5 | 43 | 3 | 43 | 4 | |

FIG. 7F, pH scan, MDA - - - MB231, 2.5 hr, n = 3 for buffer, n = 4 for others

| pH | Buffer Avg | Buffer SD | Dox-DMA-GSH 6 μM Avg | Dox-DMA-GSH 6 μM SD | Dox 3 μM Avg | Dox 3 μM SD | P value |
|---|---|---|---|---|---|---|---|
| 7.5-7.7 | 100 | 2 | 84 | 4 | 31 | 13 | Dox-DMA-GSH 6 μM vs. Dox 3 μM: 0.00205 |
| 7.2-7.3 | 86 | 2 | 66 | 3 | 29 | 2 | Dox-DMA-GSH 6 μM vs. Dox 3 μM: 0.00000342 |
| 6.9-7.0 | 78 | 4 | 56 | 2 | 30 | 6 | Dox-DMA-GSH 6 μM vs. Dox 3 μM: 0.0012 |
| 6.6-6.7 | 77 | 2 | 53 | 4 | 36 | 5 | Dox-DMA-GSH 6 μM vs. Dox 3 μM: 0.0011 |
| 6.5 | 77 | 3 | 32 | 3 | 29 | 2 | |
| 6.3-6.4 | 71 | 6 | 27 | 1 | 30 | 3 | |

FIG. 7G, pH scan, OVCAR3, 2 hr, n = 3 for buffer, n = 4 for others

| pH | Buffer Avg | Buffer SD | Dox-DMA-GSH 6 μM Avg | Dox-DMA-GSH 6 μM SD | Dox 2 μM Avg | Dox 2 μM SD | P value |
|---|---|---|---|---|---|---|---|
| 7.2-7.5 | 100 | 2 | 52 | 8 | 48 | 7 | |
| 7.1-7.3 | 108 | 8 | 55 | 6 | 51 | 2 | |
| 6.8-6.9 | 102 | 4 | 46 | 2 | 46 | 3 | |
| 6.6-6.7 | 105 | 7 | 34 | 1 | 58 | 3 | Dox-DMA-GSH 6 μM vs. Dox 2 μM: 0.0000856 |
| 6.4-6.5 | 102 | 3 | 16 | 1 | 55 | 3 | Dox-DMA-GSH 6 μM vs. Dox 2 μM: 0.00000472 |
| 6.2-6.4 | 99 | 7 | 15 | 3 | 60 | 5 | Dox-DMA-GSH 6 μM vs. Dox 2 μM: 0.0000287 |

HK2 toxicity
FIG. 7H, HK2, effect on noncancerous cells

| Concentration (nM) | Dox Avg (n = 6) | Dox SD | Dox-DMA-GSH Avg (n = 5) | Dox-DMA-GSH SD |
|---|---|---|---|---|
| 3 | 101 | 5 | 103 | 4 |
| 10 | 101 | 5 | 105 | 6 |
| 30 | 97 | 11 | 98 | 6 |

TABLE 4-continued

Exact numerical values of the mean, the standard deviation, and the P values used to generate the cell viability graphs in FIGS. 7A-7I and FIGS. 8-10.

Dose Dependence

| | | | | |
|---|---|---|---|---|
| 100 | 95 | 5 | 107 | 10 |
| 300 | 95 | 6 | 96 | 5 |
| 1000 | 71 | 2 | 106 | 5 |
| 3000 | 60 | 3 | 93 | 3 |
| 10000 | 50 | 6 | 78 | 5 |
| 30000 | 31 | 3 | 71 | 4 |

FIG. 7I, ES2, Dox - - - DMA - - - GSH, FBS effect (n = 3)

| Time | pH 6.5-6.9 Avg | pH 6.5-6.9 SD | pH 7.2-7.7 Avg | pH 7.2-7.7 SD | P value |
|---|---|---|---|---|---|
| Buffer | 92 | 9 | 100 | 1 | |
| Dox-DMA-GSH 2 μM | 58 | 6 | 86 | 4 | pH 6.5-6.9 vs. pH 7.2 - - - 7.7: 0.0046 |
| Dox-DMA-GSH 4 μM | 21 | 2 | 32 | 6 | |
| Dox-DMA-GSH 6 μM | 7 | 1 | 17 | 1 | pH 6.5-6.9 vs. pH 7.2-7.7: 5.61E−4 |
| Dox 1 μM | 77 | 1 | 48 | 16 | |
| Buffer/FBS (50%) | 89 | 1 | 94 | 3 | |
| Dox-DMA-GSH/FBS(50%) 2 μM | 50 | 3 | 89 | 5 | pH 6.5-6.9 vs. pH 7.2-7.7: 9.15E−4 |
| Dox-DMA-GSH/FBS(50%) 4 μM | 19 | 5 | 46 | 6 | pH 6.5-6.9 vs. pH 7.2-7.7: 0.00407 |
| Dox-DMA-GSH/FBS(50%) 6 μM | 8 | 2 | 21 | 3 | pH 6.5-6.9 vs. pH 7.2-7.7: 0.00406 |
| Dox/FBS(50%) 1 μM | 71 | 1 | 36 | 7 | pH 6.5-6.9 vs. pH 7.2-7.7: 0.0135 |

Figure 8A:
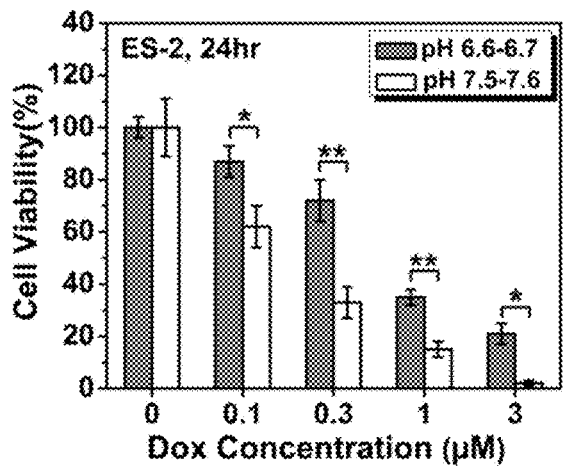
FIGS. 8A-8B show the undesirable pH-profile of free Dox—more cytotoxic at physiological pHe of 7.2-7.6 than tumor pHe of 6.6-6.8. In antiproliferation experiments with ES-2 cells, such undesirable pH-profile was seen over a wide range of PK-relevant concentrations (a, 0.1-3 μM) and time frames (b, 2-24 hr). ES-2 cells in 96-well plates were treated with Dox or buffer (negative control) at the given concentration and pH for the durations shown, then grown under normal conditions for 2-4 days before counted in MTS assays. Cell viability percentages shown are normalized to the buffer negative control at pH 7.4, which is shown as 0 μM in (8A) and not shown in (8B). The pH values of treatment solutions were measured before and after each experiment to give the pH ranges reported. Error bar is ±standard deviation (SD) (for (8A): n=3; for (8B): 2 hr, n=4; 6 hr and 12 hr, n=5; 24 hr, n=3). Statistical significance of the difference between the chosen data sets was evaluated using unpaired, two-tailed Student's t-test (*: P<0.05; : P<0.01; *: P<0.001). Exact numerical values of the mean, the SD, and the P values are reported in Table 4.
Figure 8B:
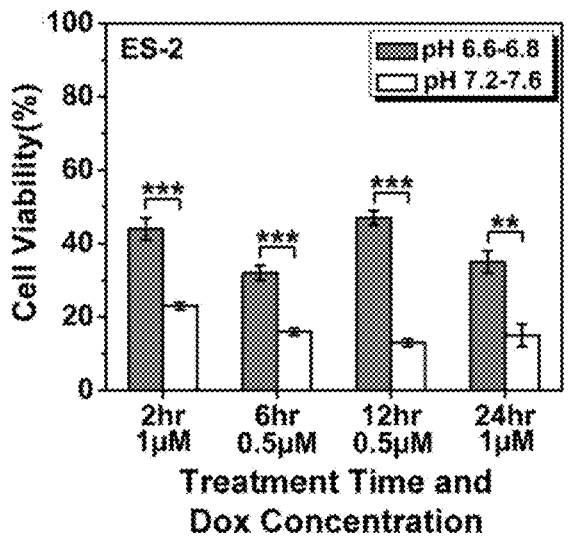

Free Dox Dose and Time
FIG. 8A ES2 (n = 3)

| [Dox] μM | pH 6.6-6.7 Avg | pH 6.6-6.7 SD | pH 7.5-7.6 Avg | pH 7.5-7.6 SD | P value |
|---|---|---|---|---|---|
| 0 | 100 | 4 | 100 | 11 | |
| 0.1 | 87 | 6 | 62 | 8 | pH 6.6-6.7 vs. pH 7.5-7.6: 0.0147 |
| 0.3 | 72 | 8 | 33 | 6 | pH 6.6-6.7 vs. pH 7.5-7.6: 0.00291 |
| 1 | 35 | 3 | 15 | 3 | pH 6.6-6.7 vs. pH 7.5-7.6: 0.00128 |
| 3 | 21 | 4 | 2 | 1 | pH 6.6-6.7 vs. pH 7.5-7.6: 0.01053 |

| Time | pH 6.6-6.8 Avg | pH 6.6-6.8 SD | pH 7.2-7.6 Avg | pH 7.2-7.6 SD | P value |
|---|---|---|---|---|---|
| 2 hr, 1 μM (n = 4) | 44 | 3 | 23 | 1 | pH 6.6-6.8 vs. pH 7.2-7.6: 0.000256 |
| 6 hr, 0.5 μ (n = 5) | 32 | 2 | 16 | 1 | pH 6.6-6.8 vs. pH 7.2-7.6: 0.0000225 |
| 12 hr, 0.5 μM (n = 5) | 47 | 2 | 13 | 1 | pH 6.6-6.8 vs. pH 7.2-7.6: 0.0000000211 |
| 24 hr, 1 μM (n = 3) | 35 | 3 | 15 | 3 | pH 6.6-6.8 vs. pH 7.2-7.6: 0.00128 |

PC3 and SKOV3

Figure 9A:
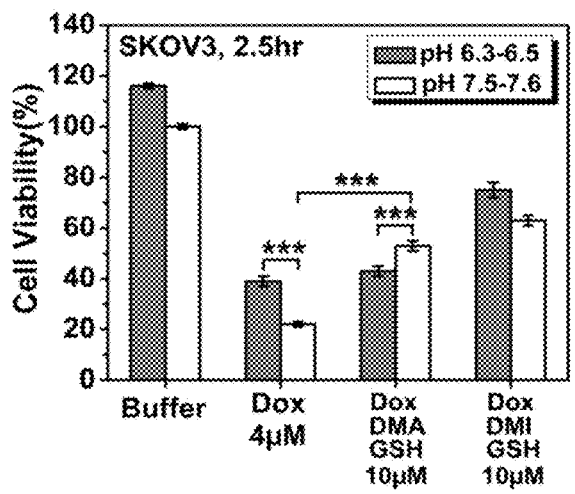
FIGS. 9A-9B show the antiproliferation effects of Dox-DMA-GSH 8 with SKOV3 and PC-3 cells. SKOV3 (9A) and PC-3 (9B) cells in 96-well plates were treated with Dox (positive control), DMA prodrug 8, Dox-DMI-GSH 7, or buffer vehicle (negative control) at the given concentration and pH for 2.5 hrs, then grown under normal conditions for 2-4 days before counted in MTS assays. Cell viability percentages shown are normalized to the buffer negative control at pH 7.4. The pH values of treatment solutions were measured before and after each experiment to give the pH ranges reported. Error bar is ±standard deviation (SD) (n=6). Statistical significance of the difference between the chosen data sets was evaluated using unpaired, two-tailed Student's t-test (*: P<0.05; : P<0.01; *: P<0.001). Exact numerical values of the mean, the SD, and the P values are reported in Table 4.
Figure 9B:
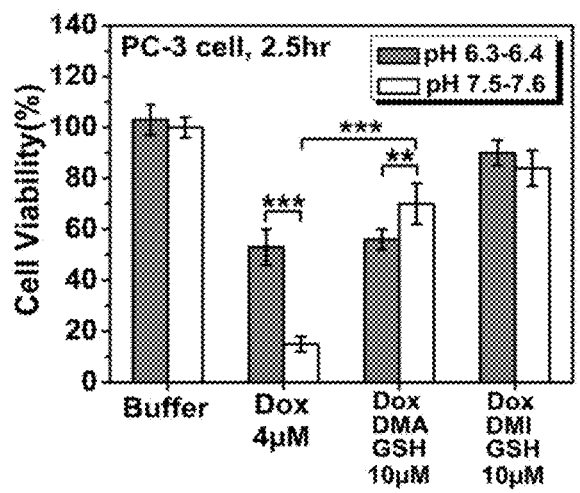

| FIG. 9B PC3, 2.5 hr (n = 6) | pH 6.3-6.4 Avg | pH 6.3-6.4 SD | pH 7.5-7.6 Avg | pH 7.5-7.6 SD | P value |
|---|---|---|---|---|---|
| Buffer | 103 | 6 | 100 | 4 | |
| Dox 4 μM | 53 | 7 | 15 | 3 | pH 6.3-6.4 vs. pH 7.5-7.6: 0.00000742 |
| Dox-DMA-GSH 10 μM | 56 | 4 | 70 | 8 | pH 6.3-6.4 vs. pH 7.5 - - - 7.6: 0.00617 |
| Dox-DMI-GSH 10 μM | 90 | 5 | 84 | 7 | |
| P value | | | Dox-DMA-GSH 10 μM vs. Dox 4 μM: 0.00000226 | | |

TABLE 4-continued

Exact numerical values of the mean, the standard deviation, and the P values used to generate the cell viability graphs in FIGS. 7A-7I and FIGS. 8-10.

Dose Dependence

| | pH 6.3-6.5 Avg | pH 6.3-6.5 SD | pH 7.5-7.6 Avg | pH 7.5-7.6 SD | P value |
|---|---|---|---|---|---|
| FIG. 9A SKOV3, 2.5 hr (n = 6) | | | | | |
| Buffer | 116 | 1 | 100 | 1 | |
| Dox 4 μM | 39 | 2 | 22 | 1 | pH6.3-6.5 vs. pH 7.5-7.6: 0.000000530 |
| Dox-DMA-GSH 10 μM | 43 | 2 | 53 | 2 | pH6.3-6.5 vs. pH 7.5-7.6: 0.00000870 |
| Dox-DMI-GSH 10 μM | 75 | 3 | 63 | 2 | |
| P value | | | Dox-DMA-GSH 10 μM vs. Dox 4 μM: 0.00000000160 | | |

Longer Time Effects

Figure 10A:
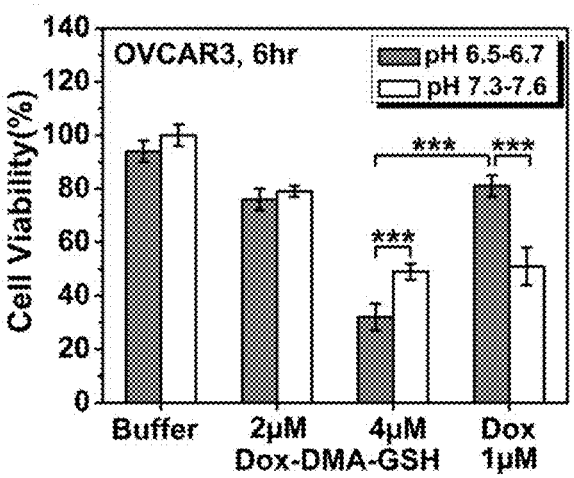
FIGS. 10A-10B show the antiproliferation effects of Dox-DMA-GSH 8 at longer treatment times. OVCAR3 cells (10A) and ES-2 cells (10B) were treated with Dox (positive control), prodrug 8, or buffer vehicle (negative control) at the given concentration and pH for 6 hrs (10A) and 12 hrs (10B), respectively, then grown under normal conditions for 2-4 days before counted in MTS assays. Cell viability percentages shown are normalized to the buffer negative controls at pH 7.4. The pH values of treatment solutions were measured before and after each experiment to give the pH ranges reported. Error bar is ±standard deviation (SD) (n=5). Statistical significance of the difference between the chosen data sets was evaluated using unpaired, two-tailed Student's t-test (*: P<0.05; : P<0.01; *: P<0.001). Exact numerical values of the mean, the SD, and the P values are reported in Table 4.

| | pH 6.5-6.7 Avg | pH 6.5-6.7 SD | pH 7.3-7.6 Avg | pH 7.3-7.6 SD | P value |
|---|---|---|---|---|---|
| FIG. 10A OVCAR3, 6 hr (n = 5) | | | | | |
| Buffer (4% 25 mM Pi) | 94 | 4 | 100 | 4 | |
| Dox-DMA-GSH 2 μM | 76 | 4 | 79 | 2 | |
| Dox-DMA-GSH 4 μM | 32 | 5 | 49 | 3 | pH 6.5-6.7 vs. pH 7.3-7.6: 0.000315 |
| Dox 1 μM | 81 | 4 | 51 | 7 | pH 6.5-6.7 vs. pH 7.3-7.6: 0.000158 |
| P value | Dox - - - DMA - - - GSH 4 μM vs. Dox 1 μM: 0.000000181 | | | | |

Figure 10B:
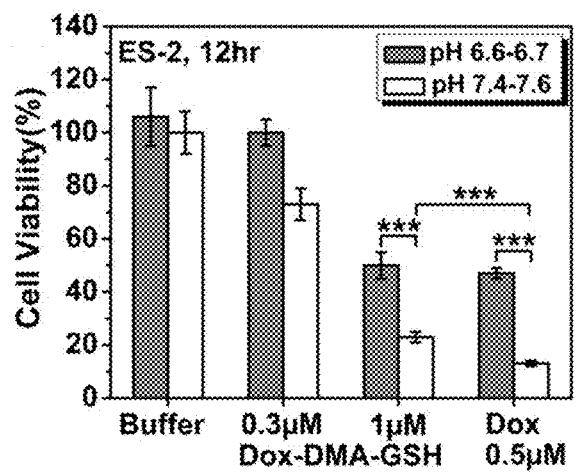
Figure 12:
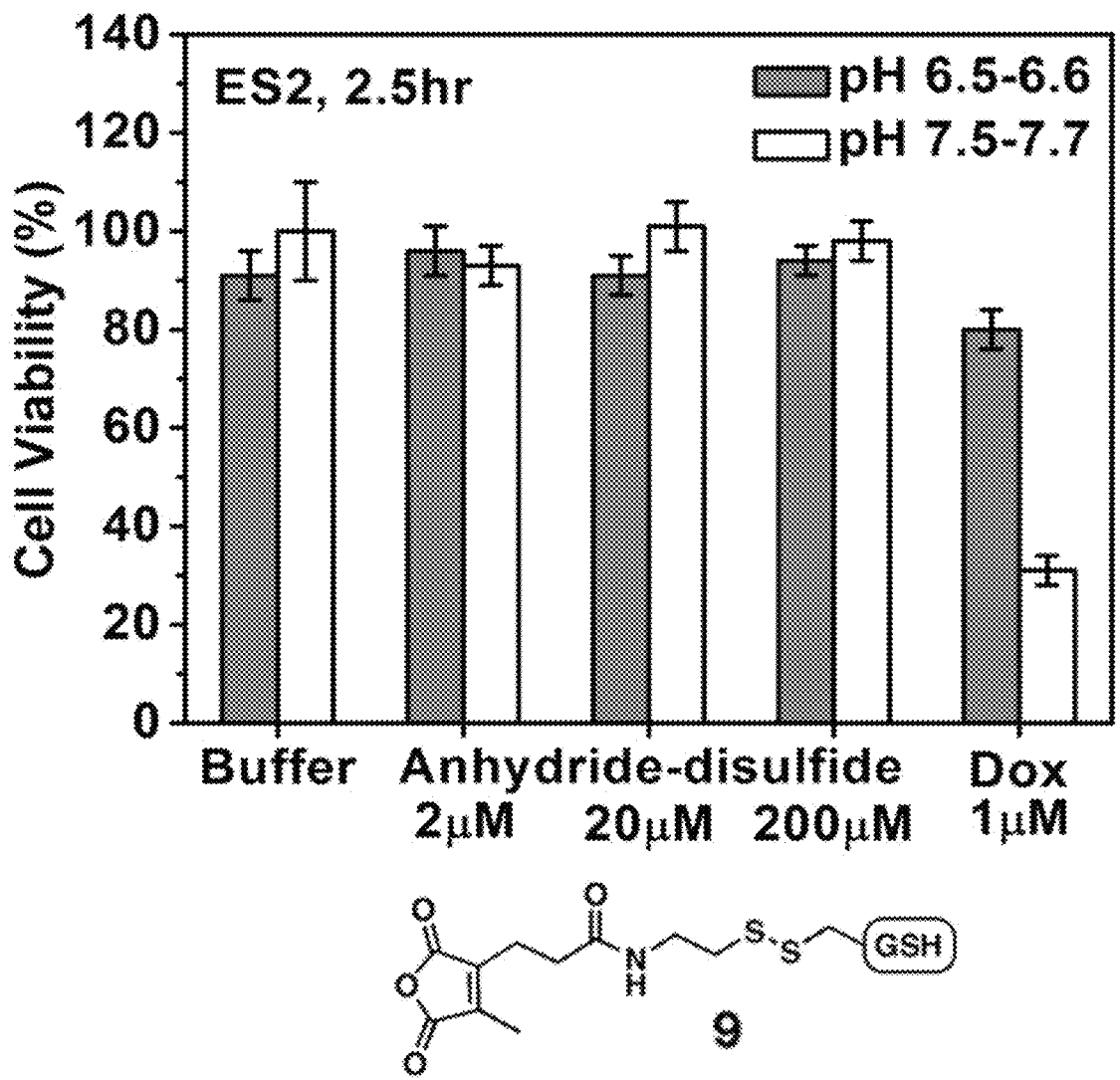
FIG. 12 shows drug release byproduct 9, anhydride-disulfide of GSH, is not toxic to cells. Byproduct 9 was independently synthesized by facile disulfide exchange from cross-linker 4: To a solution of cross-linker 4 (18 mg, 50 μmol, 1 eq.) in 500 μL of DMSO-d6 was added glutathione (GSH) free acid (18 mg, 60 μmol, 1.2 eq.) and 500 μL of D2O (reaction mixture pH: 2-3). The reaction mixture was vortexed until all components dissolved. The reaction mixture turned yellow immediately, signaling the release of 2-mercaptopyridine/thiopyridone (confirmed with 1H-NMR). Color change stopped after a few minutes (i.e., disulfide exchange mostly finished). The reaction was kept at rt in the dark for 1 h, then at 4° C. overnight to ensure reaction reached completion (confirmed with 1H-NMR). Subsequently, potential cytotoxic effect of byproduct 9 was evaluated in antiproliferation assays. The reaction mixture was used in cell experiments without purification: 2 μL of this stock of 50 mM of byproduct 9 (along with 10 mM free GSH, and 50 mM of 2-mercaptopyridine/thiopyridone) was diluted with DMEM F12 media of appropriate pH to final concentrations shown in FIG. S8 in ESI. ES-2 cells were treated with Dox (positive control), byproduct 9, or buffer vehicle (negative control) at the given concentration (all had 1% DMSO) and pH for 2.5 hrs, then grown under normal conditions for 3 days before counted in MTS assays. Cell viability percentages shown are normalized to the buffer negative controls at pH 7.4. The pH values of treatment solutions were measured before and after each experiment to give the pH ranges reported. Error bar is ±standard deviation (SD) (n=6). These data confirmed that byproduct 9 has no cytotoxic effect on cells up to 200 μM concentration (which is at least 20-fold higher than concentration of 9 in prodrug experiments).

| | pH 6.6-6.7 Avg | pH 6.6-6.7 SD | pH 7.4-7.6 Avg | pH 7.4-7.6 SD | P value |
|---|---|---|---|---|---|
| FIG. 10B ES2, 12 hr (n = 5) | | | | | |
| Buffer (8% 25 mM Pi) | 106 | 11 | 100 | 8 | |
| Dox-DMA-GSH 0.3 μM | 100 | 5 | 73 | 6 | pH 6.6-6.7 vs. pH 7.4-7.6: 0.0000537 |
| Dox-DMA-GSH 1 μM | 50 | 5 | 23 | 2 | pH 6.6-6.7 vs. pH 7.4-7.6: 0.0000638 |
| Dox 0.5 μM | 47 | 2 | 13 | 1 | pH 6.6-6.7 vs. pH 7.4-7.6: 0.0000000211 |
| P value | | | Dox-DMA-GSH 1 μM vs. Dox 0.5 μM: 0.0000235 | | |

What is claimed is:

1. A pharmaceutically acceptable formulation consisting essentially of a pre-prodrug comprising:
    an anthracycline drug having a membrane permeable therapeutic or diagnostic compound having an amine functionality,
    the drug being condensed to form a cyclized 2,3-dialkyl-substituted maleimide (DMI) comprising the amine functionality,
    a non-redox sensitive linker comprising an alkyl chain having at least two carbons, lacking a disulfide bond comprising one of the alkyl substitutions of the cyclized 2,3-dialkyl-substituted maleimide, and
    a polar modulator comprising at least one amino acid having a formal negative charge at pH 6.8, linked through the non-redox sensitive linker lacking the disulfide bond to the cyclized 2,3-dialkyl-substituted maleimide (DMI) comprising the amine functionality,
    wherein the pre-prodrug is adapted to decyclize by hydrolysis with a yield of at least 90% at pH 10 in an aqueous phosphate buffer solution for one hour at 37° C. to form a prodrug consisting of the amine functionality of the anthracycline drug forming an amide with a 2,3-dialkyl-substituted maleamic acid (DMA) and linked to the polar modulator through the non-redox sensitive linker substantially without side products, the prodrug being adapted to release the anthracycline drug in an aqueous medium at least three times faster at pH 6.5 than at pH 7.4 at 37° C.

2. The pharmaceutically acceptable formulation according to claim 1, wherein:
    the anthracycline drug,
    the cyclized 2,3-dialkyl-substituted maleimide, and
    the amino acid or peptide polar modulator,
    are selected such that upon the decyclization in pH 10 aqueous solution for 1 hour, the product comprises at least 95% of the pre-prodrug and the prodrug.

3. The pharmaceutically acceptable formulation according to claim 1, wherein the anthracycline drug is selected from the group consisting of doxorubicin, daunorubicin; epirubicin; idarubicin; sabarubicin; amrubicin; berubicin; pirarubicin; zorubicin; camsirubicin; pixantrone; and eribulin.

4. The pharmaceutically acceptable formulation according to claim 1, wherein the anthracycline drug comprises doxorubicin.

5. The composition according to claim 1, wherein the prodrug, after three hours in the aqueous medium at 37° C. releases the anthracycline drug at least 66% below pH 6.8 and at most 33% above pH 7.4.

6. The composition according to claim 1, wherein the polar modulator is selected from the group consisting of an amino acid; a dipeptide; a tripeptide; a polypeptide; a carboxylic acid; a sulfonic acid; a sulfuric acid; a phosphonic acid; a phosphoric acid; a boronic acid; a polyprotic acid; and a zwitterion.

7. A pre-prodrug pharmaceutically acceptable formulation comprising:
  a drug comprising an anthracycline having a primary amine; and
  a 2,3-dialkyl-substituted maleimide moiety cyclized with the primary amine, linked to a polar modulator comprising at least one amino acid having a moiety charged in aqueous solution at pH 6.8 though a linker, comprising an alkyl chain having at least two carbons, lacking a disulfide bond comprising an alkyl substitution of the 2,3dialkyl-substituted maleimide moiety,
  the polar modulator linked to the 2,3-dialkyl-substituted maleimide moiety being non-reactive with the drug, such that after an hour at in an aqueous phosphate buffer solution at pH 10 at 37° C., at least 90% of the pre-prodrug is decyclized to produce a prodrug, substantially without side products, consisting of the drug forming an amide with the primary amine with a 2,3-dialkyl-substituted maleamic acid linked to the polar modulator through the linker.

8. The pre-prodrug according to claim 7, wherein the prodrug is acid labile in an aqueous medium at a pH less than 6.8 to release at least 50% of the drug in three hours at 37° C. in aqueous medium, and being stable in an aqueous medium at a pH greater than 7.4 to release no more than 40% of the drug in three hours at 37° C.

9. The pre-prodrug according to claim 7, wherein the drug is doxorubicin.

10. The pre-prodrug according to claim 7, wherein the polar modulator having a moiety charged in aqueous solution at pH 6.8 comprises an amino acid or dipeptide.

11. The pre-prodrug according to claim 7, wherein the polar modulator comprises cysteine.

12. The pre-prodrug according to claim 7, wherein the polar modulator comprises glutamic acid linked via an amide bond.

13. A pharmaceutically acceptable formulation comprising a pre-prodrug comprising a non-self reacting membrane permeable therapeutic or diagnostic anthracycline drug having a free amine condensed to form a cyclized 2,3-dialkyl-substituted maleimide compound, linked through a non-redox sensitive linker comprising an alkyl chain having at least two carbons, lacking a disulfide bond comprising an alkyl substituent of the 2,3-dialkyl-substituted maleimide compound to a targeting or detargeting functionality comprising at least one amino acid which is ionized at pH 6.0-7.4 in aqueous media;
  the pre-prodrug in the pharmaceutically-acceptable formulation being convertible through in vitro ring opening to a substantially pure pH labile prodrug without side products, comprising the anthracycline drug having the free amine forming an amide with the 2,3-dialkyl-substituted maleamic acid compound, linked through the linker lacking the disulfide bond to the targeting or detargeting functionality; and
  the substantially pure pH labile prodrug being adapted for administration to a subject to selectively release the anthracycline drug proximate to a tumor, wherein the prodrug is non-membrane permeable and the anthracycline drug is membrane permeable,
  the pre-prodrug being stable at a pH greater than 7.4 to release no more than 20% of the anthracycline drug having the free amine in three hours at 37° C. in aqueous medium.

14. The pharmaceutically-acceptable formulation according to claim 13, wherein the pre-prodrug is convertible to the prodrug by treatment of the pre-prodrug with a pH 10 aqueous buffer for about 1 hour to convert the pro-prodrug to the substantially pure pH labile prodrug.

15. The pharmaceutically-acceptable formulation according to claim 13, wherein the anthracycline drug having the free amine is selected from the group consisting of doxorubicin, daunorubicin; epirubicin; idarubicin; sabarubicin; amrubicin; berubicin; pirarubicin; zorubicin; camsirubicin; pixantrone; and eribulin.

16. The pharmaceutically-acceptable formulation according to claim 13, wherein the substantially pure pH labile prodrug is adapted, after two hours in aqueous medium at 37° C., to release at least 40% of the anthracycline drug having a free amine at pH 6.5.

17. The pharmaceutically-acceptable formulation according to claim 13, wherein the substantially pure pH labile prodrug comprises at least 95% of the pre-prodrug and the pH labile prodrug.

18. The pharmaceutically-acceptable formulation according to claim 13, wherein the targeting or detargeting agent is selected from the group consisting of an amino acid; a dipeptide; a tripeptide; and a polypeptide.

19. The pharmaceutically-acceptable formulation according to claim 13, wherein the targeting or detargeting agent comprises a polypeptide polymer.

20. The pharmaceutically-acceptable formulation according to claim 13, wherein the prodrug after in vitro ring opening is present without side products resulting from attack of the 2,3-dialkyl-substituted maleimide via Michael addition.

21. The pharmaceutically-acceptable formulation according to claim 13, wherein the targeting or detargeting functionality comprises glutamic acid.

* * * * *